(12) United States Patent
Green et al.

(10) Patent No.: US 11,802,318 B2
(45) Date of Patent: Oct. 31, 2023

(54) LOOP-MEDIATED SYNTHETIC RIBOREGULATORS

(71) Applicant: Arizona Board of Regents on behalf of Arizona State University, Scottsdale, AZ (US)

(72) Inventors: Alexander Green, Scottsdale, AZ (US); Duo Ma, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 155 days.

(21) Appl. No.: 16/323,103

(22) PCT Filed: Aug. 4, 2017

(86) PCT No.: PCT/US2017/045585
§ 371 (c)(1),
(2) Date: Feb. 4, 2019

(87) PCT Pub. No.: WO2018/027177
PCT Pub. Date: Feb. 8, 2018

(65) Prior Publication Data
US 2019/0218624 A1 Jul. 18, 2019

Related U.S. Application Data

(60) Provisional application No. 62/371,094, filed on Aug. 4, 2016.

(51) Int. Cl.
*C12Q 1/6897* (2018.01)
*C12Q 1/70* (2006.01)
(Continued)

(52) U.S. Cl.
CPC .......... *C12Q 1/6897* (2013.01); *C12N 15/113* (2013.01); *C12N 15/63* (2013.01);
(Continued)

(58) Field of Classification Search
CPC ...... C12N 15/113; C12N 15/63; C12N 15/67; C12N 2310/531; C12Q 1/68; C12Q 1/6897
See application file for complete search history.

(56) References Cited

U.S. PATENT DOCUMENTS

| 2005/0153282 A1 | 7/2005 | Linnen et al. |
| 2019/0071737 A1 | 3/2019 | Green |

(Continued)

FOREIGN PATENT DOCUMENTS

| WO | 2012/058488 | 5/2012 |
| WO | 2014/074648 | 5/2014 |

(Continued)

OTHER PUBLICATIONS

Ma et al. (Nature Biomedical Engineering, 2022 vol. 6:298-309).*
(Continued)

*Primary Examiner* — Terra C Gibbs
(74) *Attorney, Agent, or Firm* — Quarles & Brady, LLP

(57) ABSTRACT

Provided herein are synthetic nucleic acid molecules known as loop-mediated riboregulators that have single-nucleotide polymorphism (SNP) sensitivity and ultralow OFF state signal levels. Loop-mediated riboregulators can activate or repress gene expression in response to trigger RNAs bearing completely arbitrary sequences. Also provided herein are methods of using such synthetic nucleic acid molecules for detecting the presence or absence of a particular target RNA in, for example, a biological sample.

11 Claims, 31 Drawing Sheets
(21 of 31 Drawing Sheet(s) Filed in Color)
Specification includes a Sequence Listing.

(51) Int. Cl.
| | |
|---|---|
| C12N 15/113 | (2010.01) |
| C12Q 1/68 | (2018.01) |
| C12N 15/67 | (2006.01) |
| C12N 15/63 | (2006.01) |
| C12Q 1/6809 | (2018.01) |
| C12Q 1/6816 | (2018.01) |
| C12Q 1/689 | (2018.01) |

(52) U.S. Cl.
CPC .............. *C12N 15/67* (2013.01); *C12Q 1/68* (2013.01); *C12Q 1/6809* (2013.01); *C12Q 1/689* (2013.01); *C12Q 1/6816* (2013.01); *C12Q 1/70* (2013.01); *C12N 2310/531* (2013.01)

(56) References Cited

U.S. PATENT DOCUMENTS

| | | |
|---|---|---|
| 2019/0185856 A1 | 6/2019 | Green |
| 2019/0256898 A1 | 8/2019 | Green |
| 2019/0276901 A1 | 9/2019 | Green |
| 2019/0285620 A1 | 9/2019 | Green |

FOREIGN PATENT DOCUMENTS

| | | |
|---|---|---|
| WO | 2016/011089 | 1/2016 |
| WO | 2017147585 A1 | 8/2017 |
| WO | 2017205668 A1 | 11/2017 |
| WO | 2018026762 A1 | 2/2018 |
| WO | 2018026765 A1 | 2/2018 |
| WO | 2018075502 A1 | 4/2018 |
| WO | 2018093898 A1 | 5/2018 |
| WO | 2018112350 A1 | 6/2018 |
| WO | 2018187687 A1 | 10/2018 |

OTHER PUBLICATIONS

International Search Report and Written Opinion for International Patent Application No. PCT/US2017/045585 dated Oct. 25, 2017.
Green et al., "Toehold Swtiches: De-Novo-Designed Regulators of Gene Expression," Cell, Oct. 23, 2014 (23.10.214), vol. 159. No. 4, pp. 925-939, entire document.
Green et al., "Complex cellular logic computation using ribocomputing devices." Nature, Jul. 26, 2017 (Jul. 26, 2017), vol. 548, No. 7665, pp. 117-121, entire document.
Auslander S., et al, "Programmable single-cell mammalian biocomputers," Nature 487, 123-+ (2012).
Barczak A. K., et al, "RNA signatures allow rapid identification of pathogens and antibiotic susceptibilities," Proceedings of the National Academy of Sciences 109, 6217-6222 (2012).
Brantl, S. et al., "Antisense RNA-mediated transcriptional attenuation: an in vitro study of plasmid pT181," Molecular Microbiology 35, 1469-1482 (2000).
Callura, J. M. et al, "Genetic switchboard for synthetic biology applications," P Natl Acad Sci USA 109, 5850-5855 (2012).
Callura, J. M. et al, "Tracking, tuning, and terminating microbial physiology using synthetic riboregulators," P Natl Acad Sci USA 107, 15898-15903 (2010).
Chappell J., et al., "Creating small transcription activating RNAs," Nat. Chem. Biol. 11, 214-220 (2015).
Daniel R., et al, "Synthetic analog computation in living cells," Nature 497, 619-+ (2013).
Elowitz M. B. et al "A synthetic oscillatory network of transcriptional regulators," Nature 403, 335-338 (2000).
Figueiredo P., et al, "Prevalence of pfmdrl, pfcrt, pfdhfr and pfdhps mutations associated with drug resistance, in Luanda, Angola," Malaria journal 7, 236 (2008).
Friedland A. E., et al, "Synthetic Gene Networks That Count," Science 324, 1199-1202 (2009).

Gardner, T.S., et al, "Construction of a genetic toggle switch in *Escherichia coli*," Nature 403, 339-342 (2000).
Green A. A., et al, "Toehold Switches: De-Novo-Designed Regulators of Gene Expression," Cell 159, 925-939 (2014).
Gultyaev A. P., et al, "Programmed cell death by hok/sok of plasmid R1: Coupled nucleotide covariations reveal a phylogenetically conserved folding pathway in the hok family of mRNAs," J. Mol. Biol. 273, 26-37 (1997).
Saacs F. J. et al, "Engineered riboregulators enable post-transcriptional control of gene expression," Nat. Biotechnol. 22, 841-847 (2004).
Jansson M. D. et al, "MicroRNA and cancer," Molecular Oncology 6, 590-610 (2012).
Karachaliou N., et al, "Real-time liquid biopsies become a reality in cancer treatment," Annals of Translational Medicine 3 (2015).
Khalil A. S., et al, "Synthetic biology: applications come of age," Nat Rev Genet 11, 367-379 (2010).
Lucks J.B., et al, "Versatile RNA-sensing transcriptional regulators for engineering genetic networks," Proc. Natl. Acad. Sci. U.S.A. 108, 8617-8622 (2011).
McArthur A. G., et al, "The Comprehensive Antibiotic Resistance Database," Antimicrobial Agents and Chemotherapy 57, 3348-3357 (2013).
McDonald, M. et al, "Use of a Single- Nucleotide Polymorphism Genotyping System to Demonstrate the Unique Epidemiology of Methicillin-Resistant *Staphylococcus aureus* in Remote Aboriginal Communities," Journal of Clinical Microbiology 44, 3720-3727 (2006).
Moon, T.S., et al, "Genetic programs constructed from layered logic gates in single cells," Nature 491, 249-253 (2012).
Mutalik, V. K., et al, "Rationally designed families of orthogonal RNA regulators of translation," Nat. Chem. Biol. 8, 447-454 (2012).
Pardee K. et al, "Paper-Based Synthetic Gene Networks," Cell 159, 940-954 (2014).
Pardee K., et al, "Rapid, Low-Cost Detection of Zika Virus Using Programmable Biomolecular Components," Cell 165, 1255-1266 (2016).
Purnick P. E. M., et al, "The second wave of synthetic biology: from modules to systems," Nat Rev Mol Cell Bio 10, 410-422 (2009).
Rodrigo G., et al, "De novo automated design of small RNA circuits for engineering synthetic riboregulation in living cells," P Natl Acad Sci USA 109, 15271-15276 (2012).
Siuti P., et al, "Synthetic circuits integrating logic and memory in living cells," Nat Biotechnol 31, 448-+ (2013).
Stephens A. J., et al, "Methicillin-resistant *Staphylococcus aureus* genotyping using a small set of polymorphisms," Journal of medical microbiology 55, 43-51 (2006).
Takahashi M. K., et al, "A modular strategy for engineering orthogonal chimeric RNA transcription regulators," Nucleic Acids Res. 41, 7577-7588 (2013).
Tyagi S, et al, "Molecular beacons: Probes that fluoresce upon hybridization," Nat Biotechnol 14, 303-308 (1996).
Wang Z., et al, "Prevalence of K13-propeller polymorphisms in Plasmodium falciparum from China- Myanmar border in 2007-2012," Malaria journal 14, 168 (2015).
Win M. N., et al, "Higher-order cellular information processing with synthetic RNA devices," Science 322, 456-460 (2008).
Winkler W., et al, "Thiamine derivatives bind messenger RNAs directly to regulate bacterial gene expression," Nature 419, 952-956 (2002).
Xie Z, et al, "Multi-Input RNAi-Based Logic Circuit for Identification of Specific Cancer Cells," Science 333, 1307-1311 (2011).
Yao C, et al, "Detection of rpoB, katG and inhA gene mutations in *Mycobacterium tuberculosis* clinical isolates from Chongqing as determined by microarray," Clin Microbiol Infec 16, 1639-1643 (2010).
Zadeh J. N., et al, "NUPACK: Analysis and Design of Nucleic Acid Systems," J Comput Chem 32, 170-173 (2011).
Zhang D. Y., et al, "Optimizing the specificity of nucleic acid hybridization," Nat Chem 4, 208-214 (2012).
U.S. Appl. No. 16/303,937.
U.S. Appl. No. 16/322,719.
U.S. Appl. No. 16/349,752.

(56) References Cited

OTHER PUBLICATIONS

U.S. Appl. No. 16/468,846.
U.S. Appl. No. 16/603,338.
U.S. Appl. No. 16/245,984.

* cited by examiner

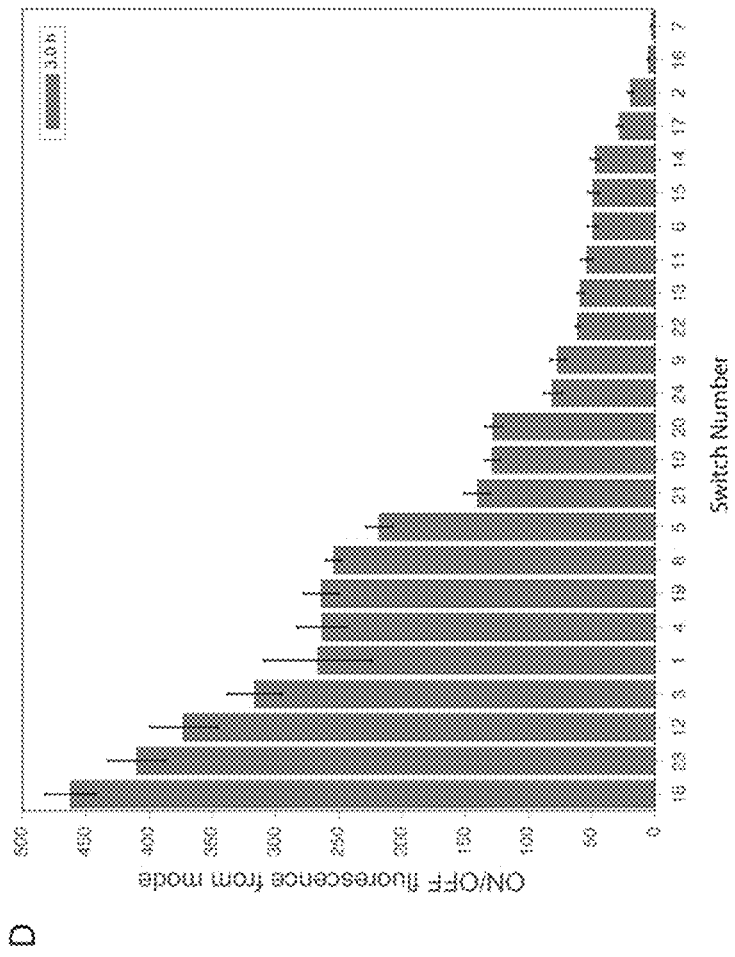
FIGS. 2A-2D, CONTINUED

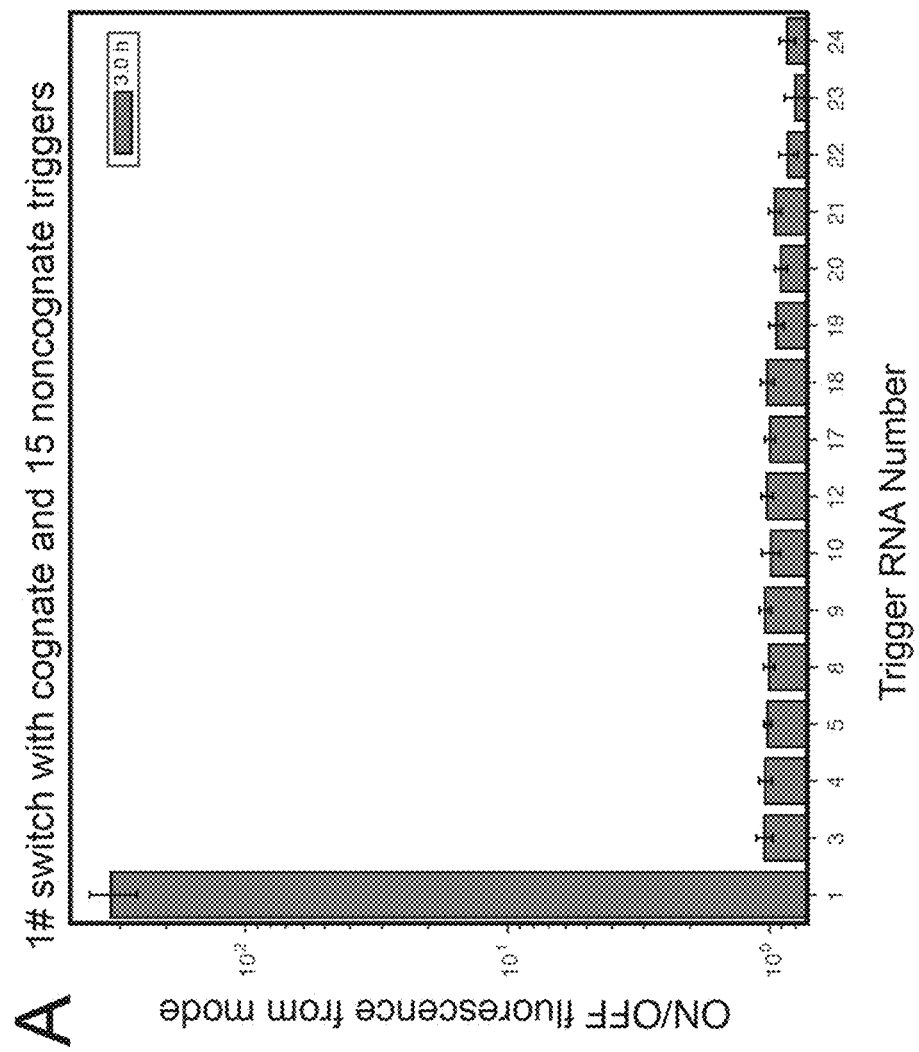

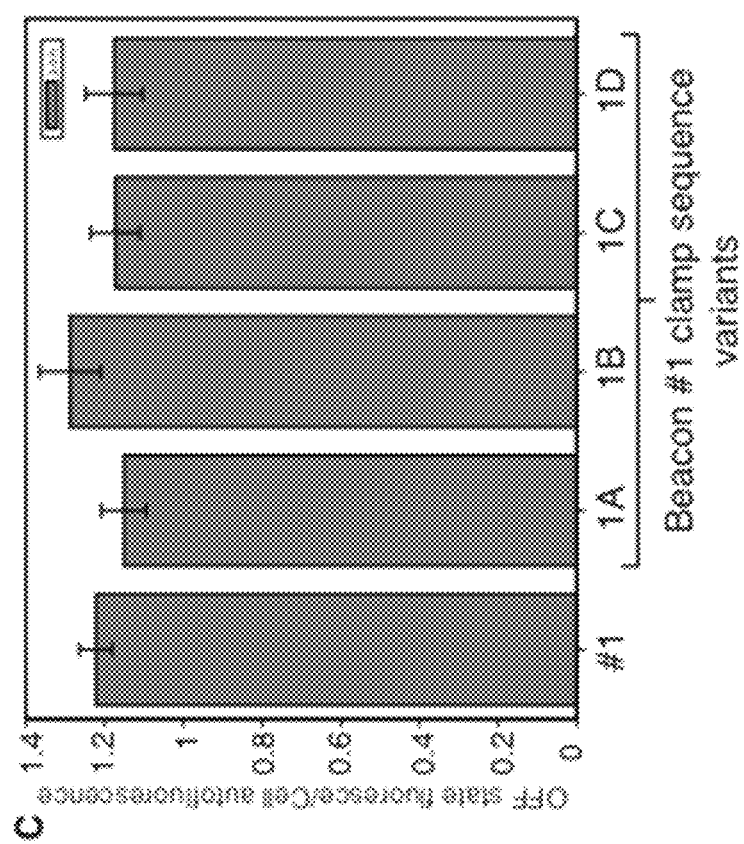
FIGS. 5A-5C, CONTINUED

FIGS. 12A-12G, CONTINUED
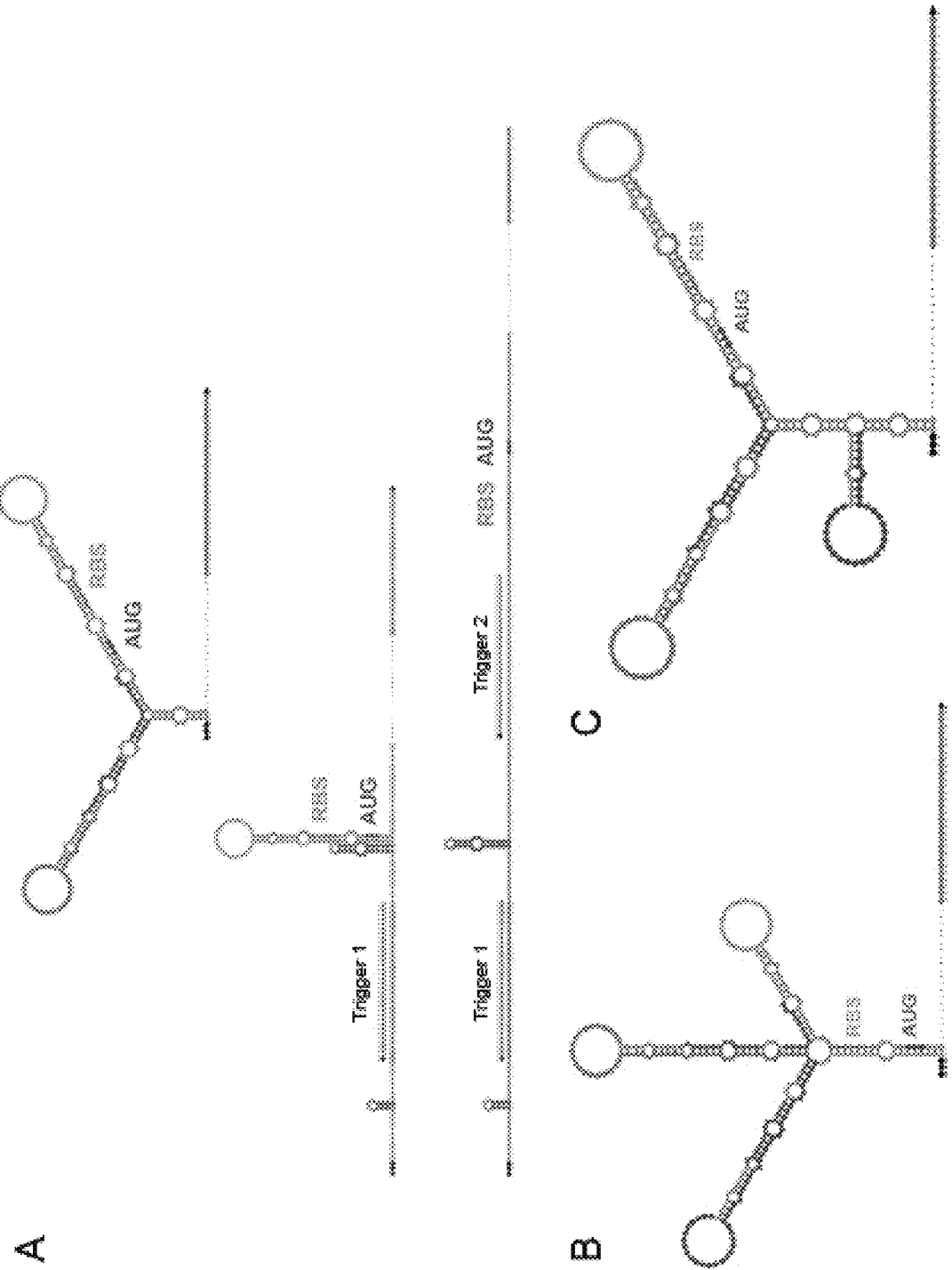

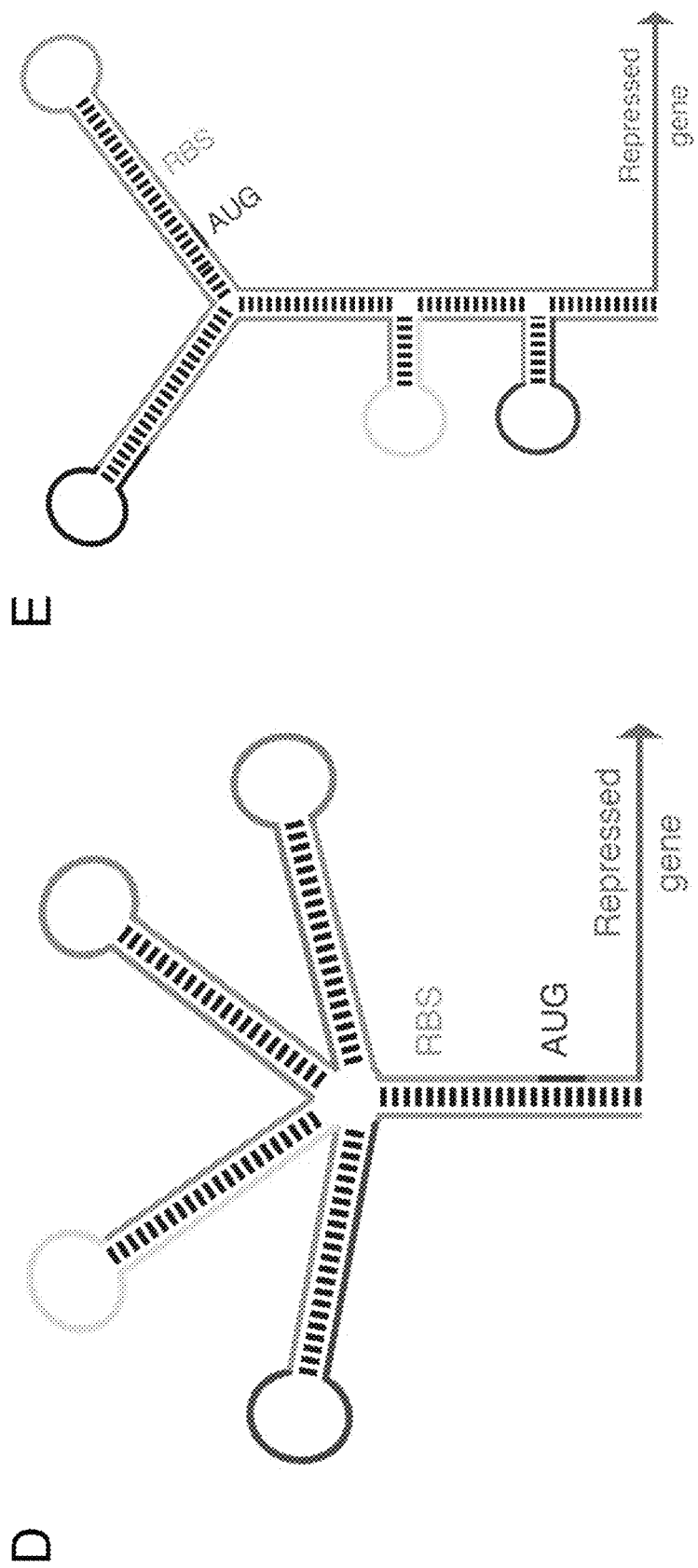
FIGS. 12A-12G, CONTINUED

FIGS. 12A-12G, CONTINUED
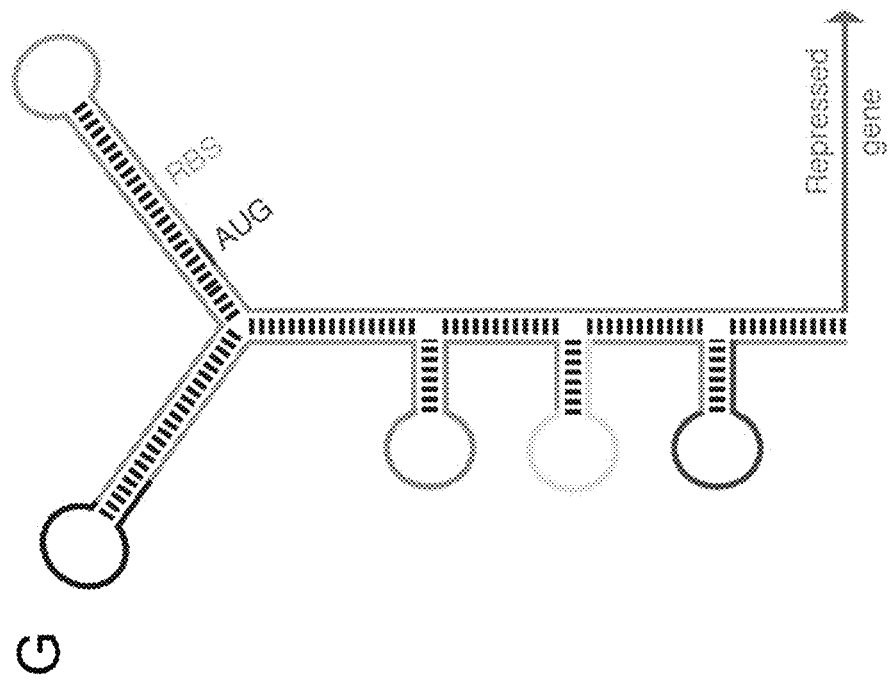
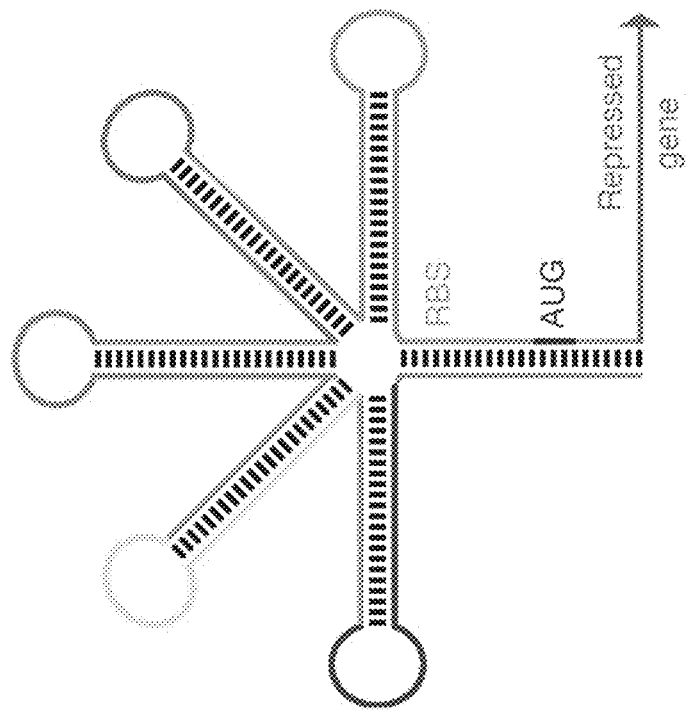

A 2-input AND gate RNA

B 3-input AND gate RNA

C 4-input AND gate RNA

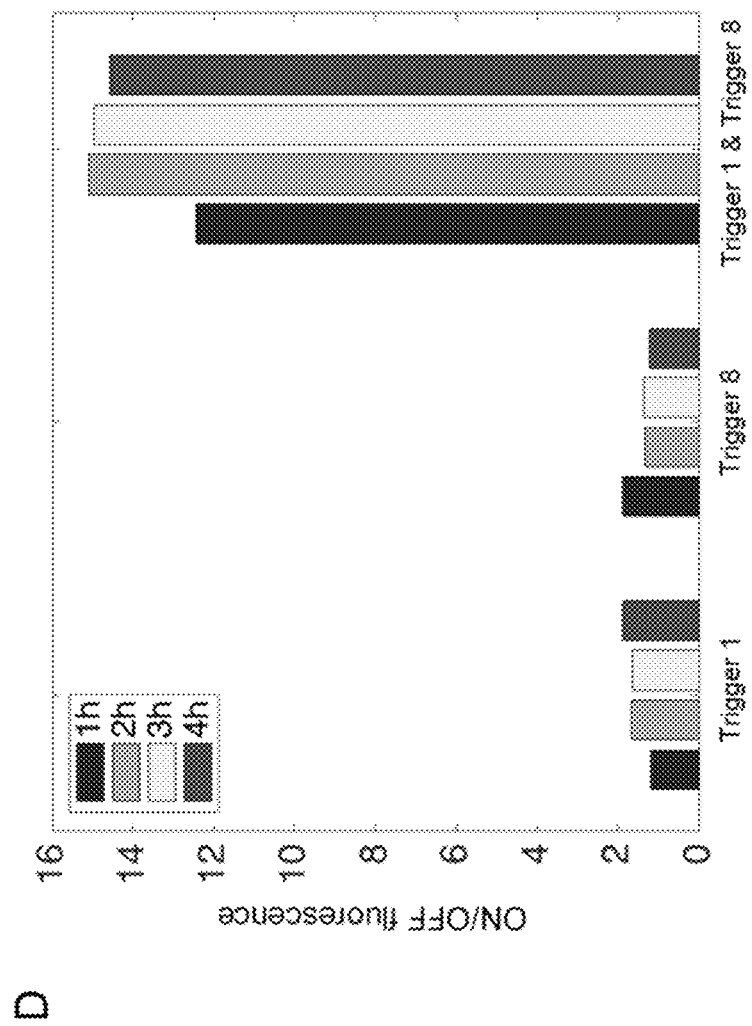
FIGS. 15A-15D, CONTINUED

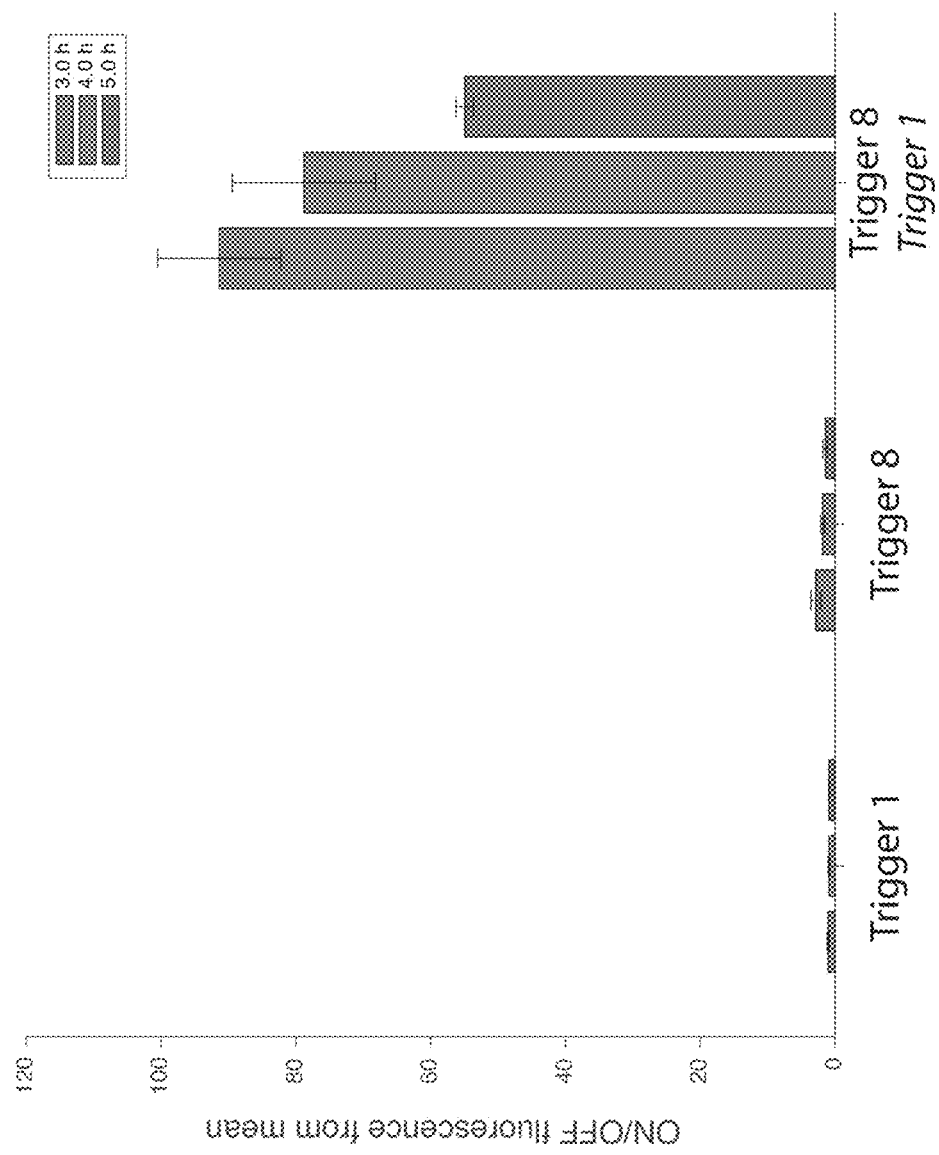

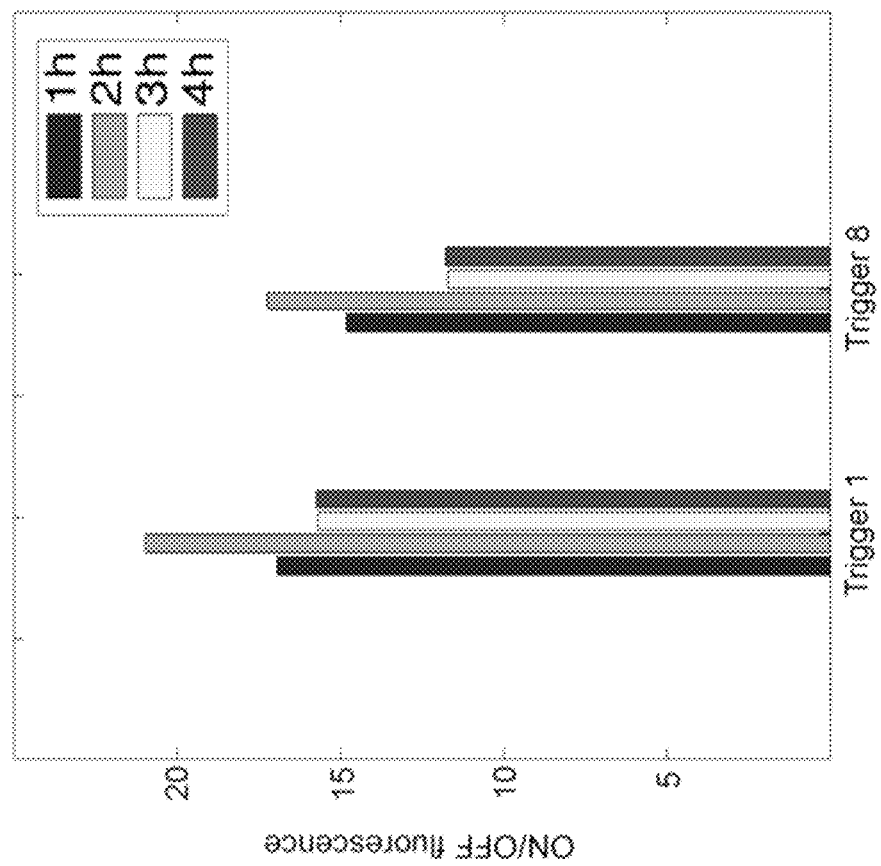

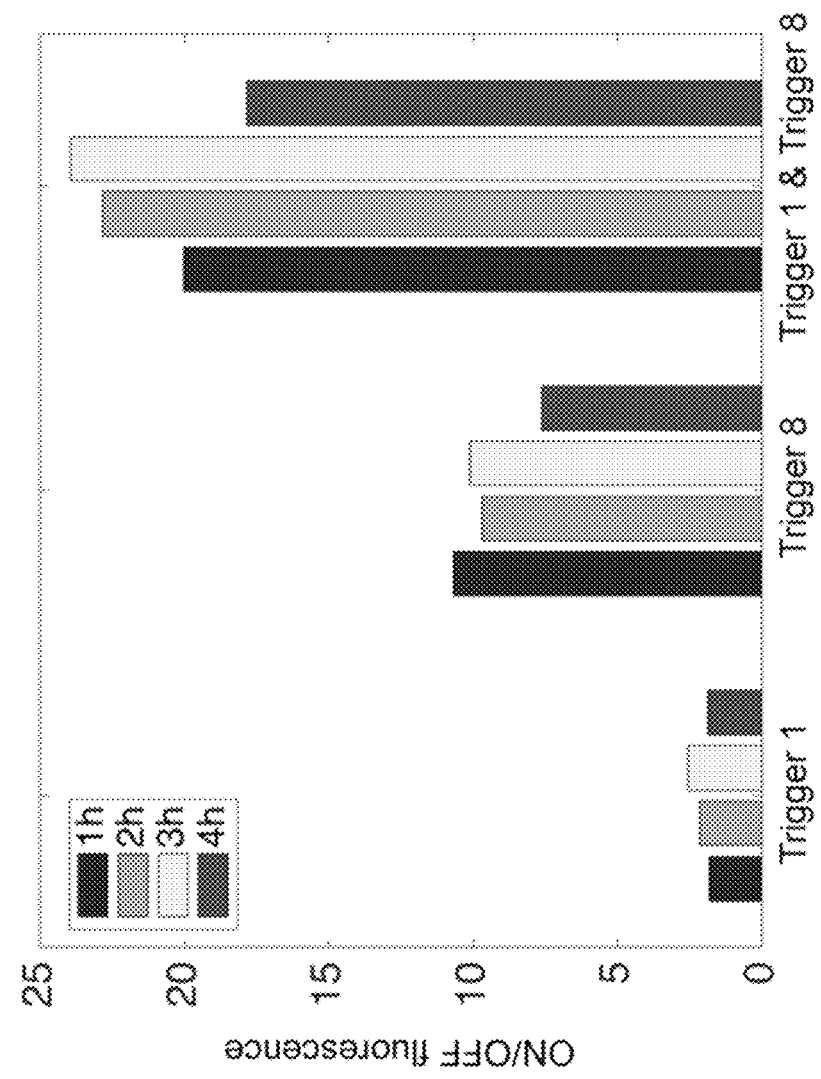
FIGS. 18A-18D, CONTINUED

LOOP-MEDIATED SYNTHETIC RIBOREGULATORS

CROSS-REFERENCE TO RELATED APPLICATIONS

This application represents the national stage entry of PCT International Application No. PCT/US2017/045585, filed on Aug. 4, 2017, and, claims priority to U.S. Provisional Application No. 62/371,094, filed Aug. 4, 2016, each of which is incorporated herein by reference as if set forth in its entirety.

STATEMENT REGARDING FEDERALLY SPONSORED RESEARCH

Not applicable.

BACKGROUND

Synthetic biology unites biology and engineering with a focus on constructing novel biomolecular components, complex synthetic networks, and unnatural metabolic pathways in living cells.

RNA based components are an attractive means to construct more complex circuits since they can take advantage of predictable Watson-Crick base pairing and exploit the numerous RNA based gene regulation systems that have been found in nature. Indeed, researchers have created many engineered RNA riboregulators based on natural systems that regulate transcription or translation upon detection of a target RNA. However, these systems have been limited in their dynamic range and their orthogonality. More recently, de-novo-designed riboregulators called toehold switches and small trans-activating RNAs have been developed that offer markedly improved performance compared to riboregulators inspired by natural systems. In particular, synthetic riboregulators can be activated by a wider range of RNA sequences, enabling improved device orthogonality, and they provide much larger dynamic range, which can lead to ON/OFF ratios above 100-fold. Despite these advantages, toehold switches do suffer from a number of important limitations. First, they exhibit noticeable signal leakage, which limits their use in applications requiring very stringent regulation of gene expression. Second, they have limited sequence discrimination capabilities precluding single nucleotide polymorphism (SNP) detection. Third, they impose restrictions on the sequence of the target RNA to be detected and the residues incorporated into the output gene. Accordingly, there remains a need in the art for improved synthetic riboregulators able to detect truly arbitrary RNAs without affecting the sequence of the output gene.

BRIEF SUMMARY

In a first aspect, provided herein is a loop-mediated riboregulator comprising a synthetic nucleic acid molecule, the synthetic nucleic acid molecule comprising
    a fully or partially double-stranded stem-forming domain;
    a start codon; a loop-forming domain comprising a trigger recognition sequence;
    a ribosomal binding site (RBS); and
    a coding domain.
The start codon can be located between the stem-forming domain and the coding domain or can be within the stem-forming domain. The loop-forming domain can have a length of 21 nucleotides. The stem-forming domain can have a length of 33 nucleotides. The trigger recognition sequence can be fully or partially complementary to a target nucleic acid molecule. The target nucleic acid molecule can be selected from the group consisting of an RNA molecule, a DNA molecule, a messenger RNA (mRNA) molecule, microRNA, small interfering RNA (siRNA), antisense RNA, non-coding RNA, and mRNA splice variant.

In another aspect, provided herein is a method of detecting presence of an RNA in a sample, the method comprising contacting to a sample a loop-mediated riboregulator as provided herein comprising a trigger recognition sequence that is fully or partially complementary to an endogenous RNA and a coding domain that encodes a reporter protein, wherein contacting occurs under conditions that allow translation of the reporter protein in the presence of the endogenous RNA but not in the absence of the endogenous RNA; and detecting the reporter protein as an indicator of the endogenous RNA in the sample. The sample can be a biological sample. Detecting the endogenous RNA molecule can be a positive indicator of a presence of a microorganism, pathogen, or gene in said sample. The microorganism or pathogen can be selected from the group consisting of HIV, Zika virus, norovirus, Yellow fever virus, and *Plasmodium falciparum*. Detecting the endogenous RNA molecule can be a negative indicator of a presence of a microorganism, pathogen, or gene in said sample. The microorganism or pathogen is selected from the group consisting of HIV, Zika virus, norovirus, Yellow fever virus, and *Plasmodium falciparum*.

In a further aspect, provided herein is a method of detecting presence of an RNA in a cell, the method comprising introducing into a cell a loop-mediated riboregulator as provided herein comprising a trigger recognition sequence that is fully or partially complementary to an endogenous RNA in the cell and a coding domain that encodes a reporter protein; culturing the cell under conditions that allow translation of the reporter protein in the presence of the endogenous RNA but not in the absence of the endogenous RNA; and detecting the reporter protein as an indicator of the endogenous RNA in the cell.

In another aspect, provided herein is a method for altering expression of a gene product in a cell, the method comprising introducing into a cell a sequence encoding a target gene product operably linked to a loop-mediated riboregulator, wherein the riboregulator comprises a trigger recognition sequence that is fully or partially complementary to a cognate trigger RNA; and wherein, in the presence of the cognate trigger RNA is present in the cell, expression of the gene product is altered. The fold-change in expression of the target gene product can be at least 25 fold. The fold-change in expression of the target gene product can be at least 50 fold. In the absence of the cognate trigger RNA, OFF state expression levels of the target gene product can be unchanged relative to a cell into which the loop-mediated riboregulator is not introduced. The loop-mediated riboregulator can be a loop-mediated repressor and expression of the target gene product is reduced relative to a cell into which the loop-mediated repressor is not introduced. The reduction can be at least 50-fold. The reduction can be at least 80-fold. Detecting the endogenous RNA molecule can be a positive indicator of a presence of a microorganism, pathogen, or gene in said sample. The microorganism or pathogen can be selected from the group consisting of HIV, Zika virus, norovirus, Yellow fever virus, and *Plasmodium falciparum*. Detecting the endogenous RNA molecule can be a negative indicator of a presence of a microorganism, pathogen, or gene in said sample. The microorganism or pathogen is selected from the group consisting of HIV, Zika virus, norovirus, Yellow fever virus, and *Plasmodium falciparum*.

In another aspect, provided herein is a synthetic nucleic acid logic circuit comprising a branched secondary structure comprising a stem-domain, a ribosomal binding site, a start codon and two or more loop-domains, wherein each loop-domain comprise a unique input RNA recognition site. The stem-domain can comprise the ribosomal binding site and the start codon. All of the loop mediated riboregulators described herein comprise a RBS and start codon located within a stem domain. Accordingly, the term "loop domain" as used herein encompasses a domain comprising a stem region plus a loop region. The 3' most loop-domain of the branched secondary structure can comprise the ribosomal binding site and the start codon. The logic circuit can comprise three loop-domains and three unique input RNA recognition sites. The logic circuit can comprise four loop-domains and four input RNA recognition sites. The logic circuit can comprise five or more loop-domains and four or more unique input RNA recognition sites.

In another aspect, provided herein is a synthetic nucleic acid logic circuit comprising a branch secondary structure comprising two or more groups of loop-domains, wherein each group of loop-domains comprises two or more loop-domains, wherein each loop-domain comprises an input RNA recognition site, and wherein the 3' most loop-domain of the branched secondary structure comprises a ribosomal binding site and a start codon. The logic circuit can be configured such that for translation to occur, one or more input RNA must be bound to the RNA recognition sites within each of the two or more groups of loop-domains. The logic circuit can comprise 2, 3, 4, 5, or more groups of loop-domains. Each group of loop-domains can comprise 2, 3, 4, 5, or more loop-domains.

The foregoing and other advantages of the invention will appear from the following description. In the description, reference is made to the accompanying drawings, which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF DRAWINGS

This patent or application file contains at least one drawing executed in color. Copies of this patent or patent application publication with color drawing(s) will be provided by the Office upon request and payment of the necessary fee.

The present invention will be better understood and features, aspects, and advantages other than those set forth above will become apparent when consideration is given to the following detailed description thereof. Such detailed description makes reference to the following drawings, wherein:

FIGS. 3A-3B present data from an orthogonal test of a loop-mediated riboregulator. (A) ON/OFF ratios from mode fluorescence value of switch #1 with different trigger pairs, all ON/OFF ratios are calculated by dividing the cell auto-fluorescence by the GFP fluorescence obtained from all switch-trigger combinations. Cell fluorescence was measured after induction for 3 hours. Error bars are the SD from at least three biological replicates; (B) Crosstalk matrix measured by flow cytometry for all switch-trigger combinations.

FIGS. 12A-12G illustrate exemplary logic gate designs. (A) Detailed design of 2-input 'AND' logic gate. (B, C) 3-input OR (B) and AND (C) logic gate RNAs. (D, E) 4-input OR (D) and AND (E) logic gate RNAs. (F, G) 5-input OR (F) and AND (G) logic gate RNAs.

FIGS. 16A-16D illustrate exemplary in vivo 2-input 'AND' logic gate designs. (A) Detailed structures of the 2-input 'AND' gate RNA design. (B) Complex of the gate RNA and trigger 1 RNA. (C) Complex of gate RNA with trigger 1 RNA and trigger 8 RNA. (D) ON/OFF ratios of the in vivo 2-input 'AND' logic gate design for different combinations of input trigger RNAs. The gate RNA was used to regulate GFP expression in E. coli cells. The OFF-state fluorescence was obtained from cells expressing two non-cognate trigger RNAs along with the gate RNA.

Figure 1A:
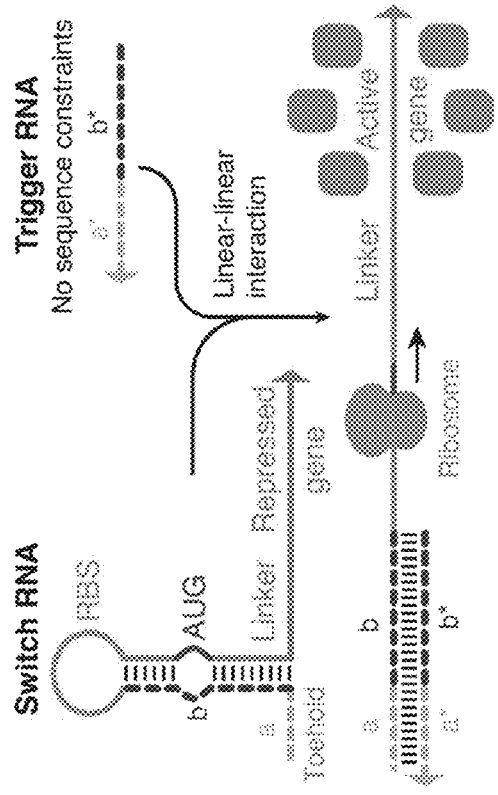
FIGS. 1A-1B present schematic illustrating exemplary loop-mediated riboregulator and toehold switch designs. (A) Toehold switch design: The target RNA binds to the toehold region of the mRNA to disrupt the repressing stem-loop and activate translation of the downstream gene. (B) Loop-mediated riboregulator design: The target RNA binds to the loop region of the mRNA to disrupt the repressing stem-loop and activate translation of the downstream gene.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION

All publications, including but not limited to patents and patent applications, cited in this specification are herein incorporated by reference as though set forth in their entirety in the present application.

The methods provided herein are based at least in part on the inventors' discovery of a new class of synthetic riboregulators known as "loop-mediated riboregulators" that can provide single-nucleotide polymorphism (SNP) sensitivity and ultralow OFF state signal levels. This new interaction mechanism enables loop-mediated riboregulators to detect truly arbitrary RNAs without affecting the sequence of the output gene. Furthermore, it enables them to regulate gene expression at both the transcriptional and translational level under certain conditions, which leads to devices with extremely low OFF state signal. As described in the paragraphs that follow and in the Examples section, testing of novel loop-mediated riboregulators in *E. coli* demonstrated that they provide a dynamic range of gene expression well over 100-fold and exhibit leakage levels nearly indistinguishable from cell auto-fluorescence. This disclosure, therefore, provides loop-mediated riboregulators and "devices" derived therefrom that offer greatly improved diversity, orthogonality, and functionality compared to previously described riboregulators.

Without being bound to any particular theory or mechanism of action, it is believed that the inventors addressed limitations associated with toehold switches using a novel loop-mediated interaction mechanism. Expression from the switch RNA is turned off initially because the ribosomal binding site (RBS) and start codons of the output gene are strongly concealed with the duplex of a stem-loop structure. When a target RNA binds to the large loop region of the mRNA, the repressing stem-loop structure is disrupted, exposing the ribosome binding site and initial codons of the output gene and enabling translation of the downstream gene. As described in the following paragraphs and the Examples section, the loop-mediated riboregulators provided herein have the capacity to resolve target RNAs down to the single-nucleotide level in vivo and can be adapted to repress translation in response to a trigger RNA. Furthermore, the loop-mediated riboregulators retain their activity in cell-free systems compatible with paper-based diagnostics, and novel computing schemes that employ loop-mediated riboregulators are useful for evaluating arbitrary Boolean logic expressions.

Accordingly, in a first aspect, provided herein is a synthetic RNA regulator having single-nucleotide polymorphism (SNP) sensitivity. Such synthetic RNA regulators are interchangeably referred to herein as "loop-mediated riboregulators" and "beacon riboregulators." As used herein, the term "loop-mediated" refers to the presence of a large loop in the synthetic RNA regulator that, upon binding of a target RNA molecule to the loop, exposes a RBS and start codon and, thus, permits translation of the downstream gene. Furthermore, the loop-mediated mechanism is sensitive to trigger RNA interactions that perturb its original secondary structure by a small number of base pairs. It is to be understood that the invention contemplates riboregulators in their final form (e.g., comprising a coding sequence for a gene of interest) or riboregulator components (e.g., a loop-mediated cis-repressing RNA not operably linked to gene of interest).

As used herein, the terms "synthetic," "engineered," and "genetically engineered" are used interchangeably and refer to the aspect of having been manipulated by the hand of man. The terms encompass a non-naturally occurring nucleic acid molecule that has been created or modified by the hand of man (e.g., using recombinant DNA technology) to differ from the sequence of the nuclease as it exists in nature, or is derived from such a molecule (e.g., by transcription, translation, etc.). A nucleic acid molecule may be similar in sequence to a naturally occurring nucleic acid but typically contains at least one artificially created insertion, deletion, inversion, or substitution relative to the sequence found in its naturally occurring counterpart. A cell that contains a synthetic or engineered nucleic acid is considered to be an engineered cell. As is common practice and is understood by those in the art, progeny and copies of an engineered polynucleotide and/or polypeptide are typically still referred to as "engineered" even though the actual manipulation was performed on a prior entity.

Figure 1B:
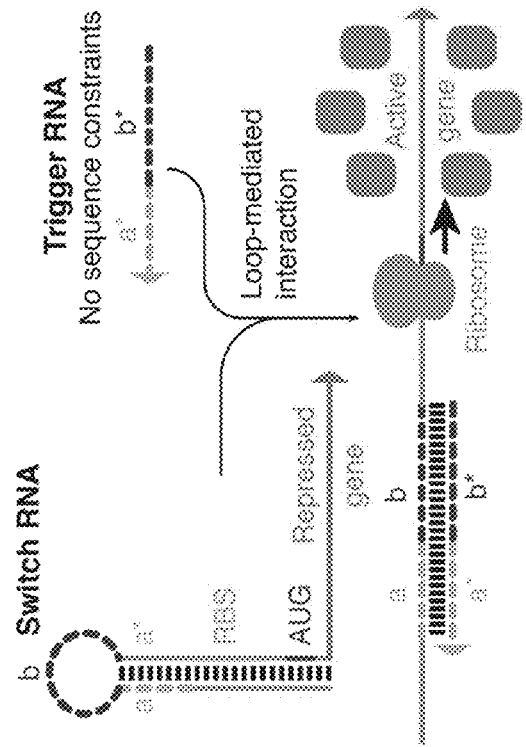

Referring to FIG. 1B, loop-mediated riboregulators can comprise a fully or partially double-stranded stem-forming domain comprising a start (initiation) codon; a large (about 21-nt) loop-forming domain comprising a ribosomal binding site (RB S) and a trigger RNA docking site; and a coding sequence ("coding domain"). Preferably, the start codon is present between the stem-forming domain and the coding domain. The loop-forming domain can be complementary to a naturally occurring RNA sequence or complementary to a non-naturally occurring RNA sequence. In general, therefore, the length of the loop-forming domain depends on the positioning of the cis-repressive sequence with respect to downstream complementary sequences. In some cases, the loop-forming domain has a length of 21 nucleotides, but in other cases will be shorter or longer than 21 nucleotides.

As used herein, the term "trigger RNA docking site" refers to a region of the loop-mediated riboregulator that is configured to bind a target or "trigger" RNA, the binding of which initiates a conformational change in the riboregulator. In some cases, the trigger RNA is an activating RNA (i.e., its presence, at a sufficient level, activates protein expression (or translation) of the coding sequence of interest). In other cases, the trigger RNA is a repressing RNA (i.e., its presence, at a sufficient level, represses protein expression or translation of the gene of interest, while expression is turned ON in the absence of the repressing trigger RNA).

In some embodiments, the stem domain comprises sequence upstream (5') and/or downstream (3') of the start codon. In some cases, the stem-forming domain has a length of 33 nucleotides, but in other cases will be shorter or longer than 33 nucleotides. The length of a stem-forming domain may be measured from the first pair of complementary nucleotides to the last pair of complementary bases and includes mismatched nucleotides (e.g., pairs other than AT, AU, GC), nucleotides that form a bulge, or nucleotides that form an inner loop.

In some cases, the stem-forming domain comprises nucleotides that form a bulge. Referring now to FIG. 1B, loop-mediated riboregulators can comprise a total of 5 bulges within the stem-forming domain: a single bulge 6 bases from the bottom base pair of the stem, a pair of bulges 12-13 bases from the bottom base pair of the stem, and a final pair of bulges 22-23 bases from the bottom base pair of the stem. As also shown in FIG. 1B, a loop-mediated riboregulator can comprise a start codon (AUG sequence) positioned on the 3' arm of the stem with the G base, situated 7 bases above the bottom base pair of the stem, and a 6 nucleotide spacer sequence separating the start codon from the RBS sequence AGAGGAGA. However, loop-mediated riboregulators of the invention need not have this particular design. It will be understood that the lengths of different domains (e.g., loop-forming domain, stem-forming domain, spacer between RBS and start codon, clamp between the start codon and the bottom base pair of the stem, and trigger binding site); number and locations of bulges; relative positions of the trigger binding site, RBS, and start codon can be modified to change the properties of the resulting loop-mediated riboregulator. For example, modifications to the number of bulges can change the degree of transcriptional regulation observed for the loop-mediated riboregulators.

As used herein, the term "non-complementarity" refers to refers to an entity in a double stranded region of an RNA composition (wherein the double strand nature of the RNA composition may arise from intramolecular hybridization within one RNA molecule and/or arise from intermolecular hybridization between two RNA molecules) that comprises non-complementary nucleotides between the two strands of the double stranded region. Thus, the region may be defined as a region of non-complementary nucleotides flanked by regions of double stranded RNA. In specific embodiments, the length of non-complementation is at least about 5 nucleotides. In other specific embodiments, the junction between the bubble and double stranded region comprises at least two T's. The terms "bubble" or "bulge" may also be used for the term "region of non-complementarity." It will be understood that the terms "bubble" and "bulge" imply no specific shape of said region, although in some embodiments it is shaped as a bubble. Complementarity of two sequences is generally determined by dividing the total number of nucleotides that participate in complementary base pairs (GC, AU, AT) when the sequences are aligned to produce the maximum number of complementary base pairs, counting all nucleotides in the two sequences (including those in bulges, mismatches, or inner loops) by the total number of nucleotides contained in both sequences. For example, consider two sequences of 19 and 20 nucleotides in length in which alignment to produce the maximum number of complementary base pairs results in 16 base pairs, 1 inner loop of 2 nucleotides, 1 mismatch, and 1 bulge (in the sequence with 20 nucleotides). The percent complementarity of the two sequences is [(16+17)/39]100. It will be appreciated that complementarity may be determined with respect to the entire length of the two sequences or with respect to portions of the sequences. As used herein, two sequences are considered "substantially complementary" herein if their complementarity is at least 50%.

Figures 2A, 2B, 2C, 2D:
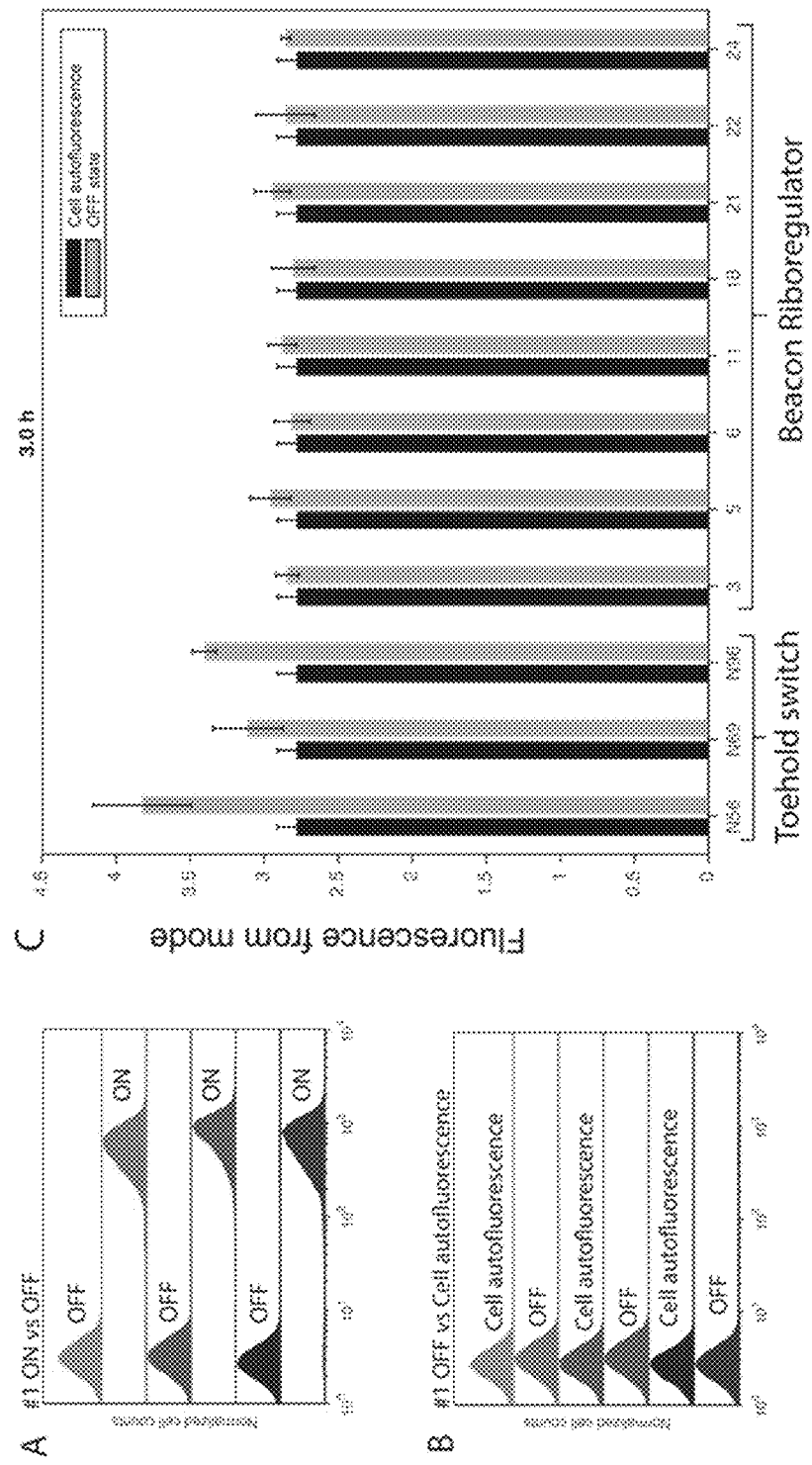
FIGS. 2A-2D demonstrate in vivo performance of loop-mediated riboregulators. (A) Flow cytometry data for loop-mediated riboregulator #1. ON measurements were obtained from *E. coli* transformed with cognate switch and trigger plasmids; OFF measurements from *E. coli* transformed with non-cognate switch and trigger plasmids. Blue peak shows the ON state signal of cells inoculated from three different colonies, green peak shows the OFF state signal cell inoculated from three different colonies. (B) Flow cytometry data of the OFF state signal of loop-mediated riboregulator #1 and bacterial autofluorescence: light blue bars show the OFF states signal of #1 and dark blue bars show the bacterial autofluorescence. Three different colonies each were inoculated to generate the data for the OFF state and autofluorescence histograms. (C) Comparison of OFF state and cell autofluorescence from mode fluorescence value for 8 loop-mediated riboregulators and 3 toehold switches. (D) ON/OFF ratios from mode fluorescence value for 24 loop-mediated riboregulators: Cell fluorescence were measured after a 3-hour induction period. Error bars are the SD from at least three biological replicates. All ON/OFF ratios were calculated by dividing the GFP fluorescence obtained from cells transformed with non-cognate switch and trigger by the fluorescence of cognate switch and trigger.

FIGS. 2A-2D show the ON/OFF median fluorescence intensity ratios obtained for twenty-four (24) loop-mediated riboregulators. Sequences for these 24 loop-mediated riboregulators are provided in Table 1. Of these 24 loop-mediated riboregulators, fifteen (15) riboregulators exhibited ON/OFF ratios exceeding 50, with twelve (12) exhibiting ON/OFF ratios exceeding 100. As shown in FIG. 2C, the OFF states of eight (8) loop-mediated riboregulators were nearly the same as cell autofluorescence and were noticeably lower than that of toehold switches.

TABLE 1

Loop-Mediated Riboregulators

| Riboregulator Name | Switch RNA or Hairpin RNA Sequence | Trigger RNA Sequence |
|---|---|---|
| BR_6clamp_act_N001 | GGGUCUAUCUAUUUCACAUCUCCUAAGUUUCCGUAUUCUGUGAAGCCCUAGGGUCCGAUACAGAAACAGAGGAGAUGACAAAUGAAUAGAAACCUGGCGGCAGCGCAAAAGAUG (SEQ ID NO: 1) | GGGCCAGUGACUUGUCACUGGGAACGGACCCUAGGGCUUCACAGAAUACGGAAACGAC (SEQ ID NO: 25) |
| BR_6clamp_act_N002 | GGGUCCAUUCAUAUACUAUCUCCUAAGUUCUCGUUCCAAUUCGCUCUCGUCCUGUCCGAACAAGAACAGAGGAGAUAAGAUAUGAAUGGAAACCUGGCGGCAGCGCAAAAGAUG (SEQ ID NO: 2) | GGGAGUGGCACGCGUGCCACUAAUGGACAGGACGAGAGCGAAUUGGAACGAGAACGAC (SEQ ID NO: 26) |
| BR_6clamp_act_N003 | GGGCUUAUCAAUAUCACAUCUCCUACGUCUUUAGUCGCUUCGGGACAGUGUGCAUCCGACUAAAGACAGAGGAGAUGACAUAUGAAUAAGAACCUGGCGGCAGCGCAAAAGAUG (SEQ ID NO: 3) | GGGUCUCCACGGAAGUGGAGAUAAGGAUGCACACUGUCCCGAAGCGACUAAAGACAAA (SEQ ID NO: 27) |
| BR_6clamp_act_N004 | GGGCGUUGAAAUCUGCUAUCUCCUACGUAUUAGUUUAUGCUACCGUAAGCCUGUCUCAAACGAAUACAGAGGAGAUACAAGAUGACAACGAACCUGGCGGCAGCGCAAAAGAUG (SEQ ID NO: 4) | GGGCACGGACUCCUGUCCGUGGGCGAGACAGGCUUACGGUAGCAUAAACUAAUACAAC (SEQ ID NO: 28) |
| BR_6clamp_act_N005 | GGGUAGUGCCAUAUCUUAUCUCCUGAGUUUCAUCUUAAAGUCCUUGUAACAGUCGUCAAGACGAAACAGAGGAGAUAACAUAUGACACUAAACCUGGCGGCAGCGCAAAAGAUG (SEQ ID NO: 5) | GGGCUCACCUGCCAAGGUGAGAGCGACGACUGUUACAAGGACUUUAAGAUGAAACGAC (SEQ ID NO: 29) |
| BR_6clamp_act_N006 | GGGAUGUCCAAUUACCUGUCUCCUGAGUCUACUCUACCUCGCUCGUUCUCAUGACUCUAGAAUAGACAGAGGAGACAUAAUGGGACAUAACCUGGCGGCAGCGCAAAAGAUG (SEQ ID NO: 6) | GGGCUGGAGCAUACGCUCCAGAAUGAGUCAUGAGAACGAGCGAGGUAGAGUAGACGAA (SEQ ID NO: 30) |
| BR_6clamp_act_N007 | GGGCAUUGGAAUCGAGUAUCUCCUACGUUUAACUUAACCCUAUACCCUCAUAACCCUUAAGAUAAACAGAGGAGAUAUACGAUGGCAAUGAACCUGGCGGCAGCGCAAAAGAUG (SEQ ID NO: 7) | GGGACAAUGUAAGAACAUUGUACGAGGGUUAUGAGGGUAUAGGGUUAAGUUAAACAGC (SEQ ID NO: 31) |
| BR_6clamp_act_N008 | GGGAUGUACAAUCCAUUAUCUCCUAAGUCUUAUUCUACUGCCUUGUUCCACUCCCGUAGAACAAGACAGAGGAGAUAACGGAUGAUACAUAACCUGGCGGCAGCGCAAAAGAUG (SEQ ID NO: 8) | GGGAUCCUGAAUACUCAGGAUGAAACGGGAGUGGAACAAGGCAGUAGAAUAAGACAAC (SEQ ID NO: 32) |

TABLE 1-continued

Loop-Mediated Riboregulators

| Riboregulator Name | Switch RNA or Hairpin RNA Sequence | Trigger RNA Sequence |
|---|---|---|
| BR_6clamp_act_N009 | GGGCAUUACAAUUACCUAUCUCCUACAUUCUAGUGCCACGAGUUAGUAUCUUCGCCUGCACAAGAAUAGAGGAGAUAGAUAAUGGUAAUGAACCUGGCGGCAGCGCAAAAGAUG (SEQ ID NO:9) | GGGUCCGAUCUAGAGAUCGGAUAAAGGCGAAGAUACUAACUCGUGGCACUAGAAUACA (SEQ ID NO: 33) |
| BR_6clamp_act_N010 | GGGCAUAUGAAUCGGAAGUCUCCUACAGUCAUUUCGUCUUCGAGGCCGUCUCAUCUGCGAACUGACUAGAGGAGACUAACGAUGAAUAUGAACCUGGCGGCAGCGCAAAAGAUG (SEQ ID NO: 10) | GGGAUCCAGCCGAUGCUGGAUGAACAGAUGAGACGGCCUCGAAGACGAAAUGACUAGA (SEQ ID NO: 34) |
| BR_6clamp_act_N011 | GGGCAUCACAAUUACAUAUCUCCUGAAUCUUCAUUCCAUUCCAUUGUCUCCAGACCGGAAUGAAGAUAGGGAGAUAGAUAAUGAUGAUGAACCUGGCGGCAGCGCAAAAGAUG (SEQ ID NO: 11) | GGGAGCCAUCGCAUGAUGGCUGGACGGUCUGGAGACAAUGGAAUGGAAUGAAGAUACU (SEQ ID NO: 35) |
| BR_6clamp_act_N012 | GGGAUCAUAGAUGCAGUAUCUCCUAAACUUCCACUUCGAUCGCAGGUUUCACACUACAAGUAGAAGUAGAGGAGAUAACGCAUGAUGAUAACCUGGCGGCAGCGCAAAAGAUG (SEQ ID NO: 12) | GGGCAGCUACUCAAGUAGCUGGAGGUAGUGUGAAACCUGCGAUCGAAGUGGAAGUACG (SEQ ID NO: 36) |
| BR_6clamp_act_N013 | GGGUCGUUCAAUGUAGUAUCUCCUAAGUCGUUUCUAGUACGAGAUCGCCUGUUCCCAUAGAUACGACAGAGGAGAUAAGACAUGAAACGAAACCUGGCGGCAGCGCAAAAGAUG (SEQ ID NO: 13) | GGGAGUCAGCUGAUGCUGACUAAGUGGGAACAGGCGAUCUCUACUAGAAACGACAAU (SEQ ID NO: 37) |
| BR_6clamp_act_N014 | GGGCAUUUGCAUAUACCAUCUCCUAAGUCUUAUUCGUGACGCUUAAGUCCCGCAGAGCGAAUAAGACAGAGGAGAUGAGAUAUGGAAAUGAACCUGGCGGCAGCGCAAAAGAUG (SEQ ID NO: 14) | GGGCGUCACCUUUAGGUGACGGAACUCUGCGGGACUUAAGCGUCACGAAUAAGACACA (SEQ ID NO: 38) |
| BR_6clamp_act_N015 | GGGCCAUACAAUCAACCGUCUCCUAAGUAUUCCAAUACCGUGUCAAUCUCUAUAAGCAUUGAAAUACAGAGGAGACGGAUGAUGAUAUGGAACCUGGCGGCAGCGCAAAAGAUG (SEQ ID NO: 15) | GGGCAGACCCUGCUGGGUCUGGACGCUUAUAGAGAUUGACACGGUAUUGGAAUACAAA (SEQ ID NO: 39) |
| BR_6clamp_act_N016 | GGGCAAUUACAUGCAACGUCUCCUACAUUCUUAUCUAUCAAAGUUCACGCACUACGCAGAUAAGAAUAGAGGAGACGAAGCAUGAAAUUGAACCUGGCGGCAGCGCAAAAGAUG (SEQ ID NO: 16) | GGGACGUUACUUAGGUAACGUGGAGCGUAGUGCGUGAACUUUGAUAGAUAAGAAUGAA (SEQ ID NO: 40) |
| BR_6clamp_act_N017 | GGGACUCUACAUGUACUAUCUCCUACGUUUAUCUAUGCUCCUAUAUCGUGACGUCUGAUAGAUAAACAGAGGAGAUAAGACAUGCAGAGUAACCUGGCGGCAGCGCAA (SEQ ID NO: 17) | GGGAGCUCGCAACCGCGAGCUAGACAGACGUGACGAUAUAGGAGCAUAGAUAAACUCA (SEQ ID NO: 41) |
| BR_6clamp_act_N018 | GGGAUCUACCAUUCAUUAUCUCCUAGGUUUCAGUUCUAUUAGGGCUACGAAGACCGUGAACAGAAACAGAGGAGAUACGGAAUGAUAGAUAACCUGGCGGCAGCGCAA (SEQ ID NO: 18) | GGGAGCAUGCCGUGGCAUGCUAGGACGGUCUUCGUAGCCCUAAUAGAACUGAAACAUG (SEQ ID NO: 42) |
| BR_6clamp_act_N019 | GGGCUUAUACAUUUACCGUCUCCUAAGCUUAGUCGUGAAACCUAUACAAUCCUGUGCACGAAUAAGCAGAGGAGACGACAAAUGAAUAAGAACCUGGCGGCAGCGCAA (SEQ ID NO: 19) | GGGCACAGACGUACGUCUGUGGAAGCACAGGAUUGUAUAGGUUUCACGACUAAGCGAA (SEQ ID NO: 43) |
| BR_6clamp_act_N020 | GGGCUUAGCAAUGUAGAAUCUCCUGAGUUAGUUCCCAUUGUUACUUUCACAUCUCACGGGAACUAACAGAGGAGAUUGAACAUGACUAAGAACCUGGCGGCAGCGCAA (SEQ ID NO: 20) | GGGCCUACGCACUCGCGUAGGAUUGUGAGAUGUGAAAGUAACAAUGGGAACUAACGAA (SEQ ID NO: 44) |

TABLE 1-continued

Loop-Mediated Riboregulators

| Riboregulator Name | Switch RNA or Hairpin RNA Sequence | Trigger RNA Sequence |
|---|---|---|
| BR_6clamp_act_N021 | GGGCCUAACAAUGUACCGUCUCCUAAGUC UCGAUCCCGGUAUCUUAUGGCCUGGUCGG GAUAGAGACAGAGGAGACGAAACAUGAU UAGGAACCUGGCGGCAGCGCAA (SEQ ID NO: 21) | GGGCCAGACCAUCGGGUCU GGAGGCGACCAGGCCAUA AGAUACCGGGAUCGAGAC AAC (SEQ ID NO: 45) |
| BR_6clamp_act_N022 | GGGCUUAUCCAUUUCACGUCUCCUACGCC UUCAUCGUCGUCUUGCACCGUCCUACUCC GAUAAAGGCAGAGGAGACGACAAAUGAA UAAGAACCUGGCGGCAGCGCAA (SEQ ID NO: 22) | GGGACCGUACUCCCGUACG GUGAUGAGUAGGACGGUG CAAGACGACGAUGAAGGC UAC (SEQ ID NO: 46) |
| BR_6clamp_act_N023 | GGGCCUAACAAUUCUAUAUCUCCUAAGUG UCAGUUCUUAGGCUACACAUGUGAGUGUG AACAGACACAGAGGAGAUAACGAAUGAU UAGGAACCUGGCGGCAGCGCAA (SEQ ID NO: 23) | GGGAUGAUCGACACCGAU CAUAGAACACUCACAUGU GUAGCCUAAGAACUGACA CAGC (SEQ ID NO: 47) |
| BR_6clamp_act_N024 | GGGCUUAUCAAUUGCACAUCUCCUAGGUC AUCUCGUCCAAAUCGAUCAUCACUGUCCA CGAGAUGACAGAGGAGAUGAACAAUGGA UAAGAACCUGGCGGCAGCGCAA (SEQ ID NO: 24) | GGGCUGCUCCCGUGGGAGC AGGACGGACAGUGAUGAU CGAUUUGGACGAGAUGAC AUA (SEQ ID NO: 48) |

The advantages of the loop-mediated riboregulators described herein are multifold. First, since the trigger RNA does not interact with the bottom of the switch RNA stem, loop-mediated riboregulators can accept completely arbitrary trigger RNAs (target RNAs) without affecting the output protein sequence. Second, the loop-mediated interaction mechanism results in a system in which a similar number of base pairs exist before and after formation of the trigger/switch complex. This balance in base pairing between these two states results in very sensitive thermodynamics that can be exploited for improved device to device orthogonality and sequence discrimination down to the single-nucleotide level. Third, loop-mediated riboregulators employ a very long stem that provides transcriptional regulation with certain RNA polymerases as a result of its intrinsic termination capacity. Coupling of transcriptional and post-transcriptional regulation leads to ultralow leakage levels for loop-mediated riboregulators when used with appropriate RNA polymerases.

Nucleic acids generally refer to polymers comprising nucleotides or nucleotide analogs joined together through backbone linkages such as but not limited to phosphodiester bonds. Nucleic acids include deoxyribonucleic acids (DNA) and ribonucleic acids (RNA) such as messenger RNA (mRNA), transfer RNA (tRNA), etc. Other target nucleotide sequences include, without limitation, DNA or RNA sequences that can identify a species (e.g., ribosomal RNAs or DNAs); DNA or RNA sequences that are associated with a particular genetic condition (e.g., where the target comprises a single nucleotide polymorphism (SNP) for which PAM identification is advantageous, including, without limitation, BRCA1/BRCA2 mutations, cystic fibrosis, Duchenne muscular dystrophy, hemochromatosis); DNA or RNA sequences for identifying a particular person with high certainty (e.g., identifying a suspect in a criminal investigation; identifying a "high value target" in a military operation).

Nucleic acids may be single-stranded, double-stranded, and also tripled-stranded. The nucleic acids of the invention, including the loop-mediated riboregulator, may be provided or present in a larger nucleic acid. The larger nucleic acid may be responsible for the transcription and thus production of the loop-mediated riboregulator, as described in Example 1, for example. The larger nucleic acid may comprise a nucleotide sequence that is transcribed to produce the loop-mediated riboregulator. For convenience, the invention may refer to the larger nucleic acid as comprising the loop-mediated riboregulator although it is to be understood that in practice this intends that the larger nucleic acid comprises a sequence that encodes the loop-mediated riboregulator. Such encoding sequences may be operably linked to other sequences in the larger nucleic acid such as but not limited to origins of replication. As used herein, "operably linked" refers to a relationship between two nucleic acid sequences wherein the production or expression of one of the nucleic acid sequences is controlled by, regulated by, modulated by, etc., the other nucleic acid sequence. For example, the transcription of a nucleic acid sequence is directed by an operably linked promoter sequence; post-transcriptional processing of a nucleic acid is directed by an operably linked processing sequence; the translation of a nucleic acid sequence is directed by an operably linked translational regulatory sequence; the transport or localization of a nucleic acid or polypeptide is directed by an operably linked transport or localization sequence; and the post-translational processing of a polypeptide is directed by an operably linked processing sequence. Preferably a nucleic acid sequence that is operably linked to a second nucleic acid sequence is covalently linked, either directly or indirectly, to such a sequence, although any effective association is acceptable.

As used herein, the terms "regulatory sequence" and "regulatory element" are used interchangeably and refer to a region of nucleic acid sequence that directs, enhances, or inhibits the expression (e.g., transcription, translation, processing, etc.) of sequence(s) with which it is operatively linked. The term includes promoters, enhancers and other transcriptional and/or translational control elements. The loop-mediated riboregulator moiety may be considered to be a regulatory sequence or element to the extent it controls translation of a gene of interest that is operably linked to the loop-mediated riboregulator. The invention contemplates that the loop-mediated riboregulator may direct constitutive or inducible protein expression. Inducible protein expression may be controlled in a temporal or developmental manner.

In some cases, the loop-mediated riboregulator is operably linked to a reporter element (e.g., an *E. coli* lacZ reporter element encoding β-galactosidase) that is 3' to the hairpin structure (i.e., the loop and stem domains). Reporter proteins appropriate for the methods provided herein include, without limitation, enzymatic reporters (e.g., β-galactosidase, alkaline phosphatase, DHFR, CAT), fluorescent or chemiluminescent reporters (e.g., GFP variants, mCherry, luciferase, e.g., luciferase derived from the firefly (*Photinus pyralis*) or the sea pansy (*Renilla reniformis*) and mutants thereof), etc.

Biological samples appropriate for use according to the methods provided herein include, without limitation, blood, serum, urine, saliva, tissues, cells, and organs, or portions thereof.

The nucleic acid molecule can be, e.g., an RNA, a DNA, an mRNA, and/or a genomic nucleic acid. In some embodiments of any of the aspects, the nucleic acid molecule can be human, animal, prokaryotic, eukaryotic, or pathogenic in origin. In some embodiments of any of the aspects, the nucleic acid molecule can be of viral origin. Nucleic acids and/or other moieties of the invention may be isolated. As used herein, "isolated" means separate from at least some of the components with which it is usually associated whether it is derived from a naturally occurring source or made synthetically, in whole or in part.

Nucleic acids and/or other moieties of the invention may be purified. As used herein, purified means separate from the majority of other compounds or entities. A compound or moiety may be partially purified or substantially purified. Purity may be denoted by a weight by weight measure and may be determined using a variety of analytical techniques such as but not limited to mass spectrometry, HPLC, etc.

In another aspect, provided herein are methods of altering gene expression using the synthetic nucleic acid molecules described herein. In some cases, the method alters expression of an enzyme (or other protein) in a cell and comprises introducing into a cell an enzyme coding sequence operably linked to a loop-mediated riboregulator having a trigger recognition sequence that is fully or partially complementary to an endogenous trigger RNA, whereby expression of the enzyme is altered according to the level of repressing trigger RNA introduced to the cell.

In some cases, loop-mediated riboregulators can be used to regulate expression of one or more enzymes, including entire metabolic pathways. In such cases, the method includes placing the method includes placing one or more enzymes (e.g., each enzyme in a metabolic pathway) under control of loop-mediated riboregulators that respond to the same trigger RNA. The inventors have demonstrated that the loop-mediated riboregulators provided herein yield unexpectedly high fold-change values, often in the 100-fold range. As used herein, the terms "expressing," "expression," or "express" refer to the production of a gene product (e.g., an mRNA transcript from a nucleic acid sequence encoding thereof). As used herein, the terms "gene product" and "expression product" generally refer to an RNA transcribed from the gene or a polypeptide encoded by an RNA transcribed from the gene. Thus a regulatory element, environmental condition, stimulus, etc., that alters the level of transcription or the stability of an RNA transcribed from a gene or alters its ability to serve as a template for translation will be said to alter expression of the gene. Similarly, a regulatory element, environmental condition, stimulus, etc., that alters the level of translation or stability of a polypeptide translated from an RNA transcribed from the gene will be said to alter expression of the gene.

In some cases, loop-mediated riboregulators are incorporated into complex, multi-input logic circuits. It is envisioned that the loop-mediated riboregulators can be incorporated into these multi-input circuits designed into computational systems for evaluating OR, AND, and conjunctive normal form (CNF) logic. For diagnostics purposes, multi-input logic circuits can be used to increase assay specificity or sensitivity. For instance, an AND or NOT-AND ("NAND") expression can reduce false positives by ensuring that more than one pathogen-associated RNA is present in a sample. An OR or NOT-OR ("NOR") expression can reduce false negatives by sensing more than one RNA in the same sample. In vivo, a multi-input logic circuit can be used to sense the set of RNAs produced by a prokaryote in response to environment stresses. This RNA signature can be used to modulate production of enzymes or identify cells that are susceptible to antibiotics or screen for new antibiotic compounds. In addition, the circuits that sense a set of RNAs expressed by the host could be used to generate whole-cell biosensors that detect toxic chemicals in the environment. It is envisioned that any logic circuit described herein can be used in application and methods designed to detect RNA's within a cell, either endogenous or synthetic, and that the logic circuit may be used to detect specific combination of RNAs within a cell or other biological sample.

As described herein, "AND" logic circuits are synthetic nucleic acid logic circuits comprising multiple input RNA recognition sites configured such that all input RNAs must be bound to their complementary input RNA recognition sites for expression of the target gene to occur. AND logic circuits comprise a branched secondary structure comprising two or more arms wherein a ribosomal binding site and a start codon for a target gene are located within the 3' most arm of the branched secondary structure. Each arm of the branched secondary structure comprises a loop-domain comprising an input RNA recognition site and the separate input RNA recognition sites of the separate arms recognize unique input RNA sequences. For example, a 2-input AND circuit comprises two arms, a first 5' arm comprising a first input RNA recognition site and a second 3' arm comprising a second input RNA recognition site, a ribosomal binding domain and a start codon. It is envisioned that the AND logic circuit can be designed to accommodate binding of 2, 3, 4, 5, or more input RNA sequences at 2, 3, 4, 5 or more input RNA recognition sites, respectively, on 2, 3, 4, 5, or more arms, respectively. For these circuits, the input species can be RNA trigger molecules. In some embodiments, the AND circuit comprises 3 arms of a branched secondary structure and comprises 3 separate input RNA binding domains. In some embodiments, the AND circuit comprises 4 arms of a branched secondary structure and comprises 4 separate input RNA binding domains.

For all loop-mediated riboregulators described herein, the RBS and start codon are located within a stem domain. Accordingly, the term "loop domain" as used herein encompasses a stem region plus a loop region.

Figures 10A, 10B, 10C, 10D, 10E:
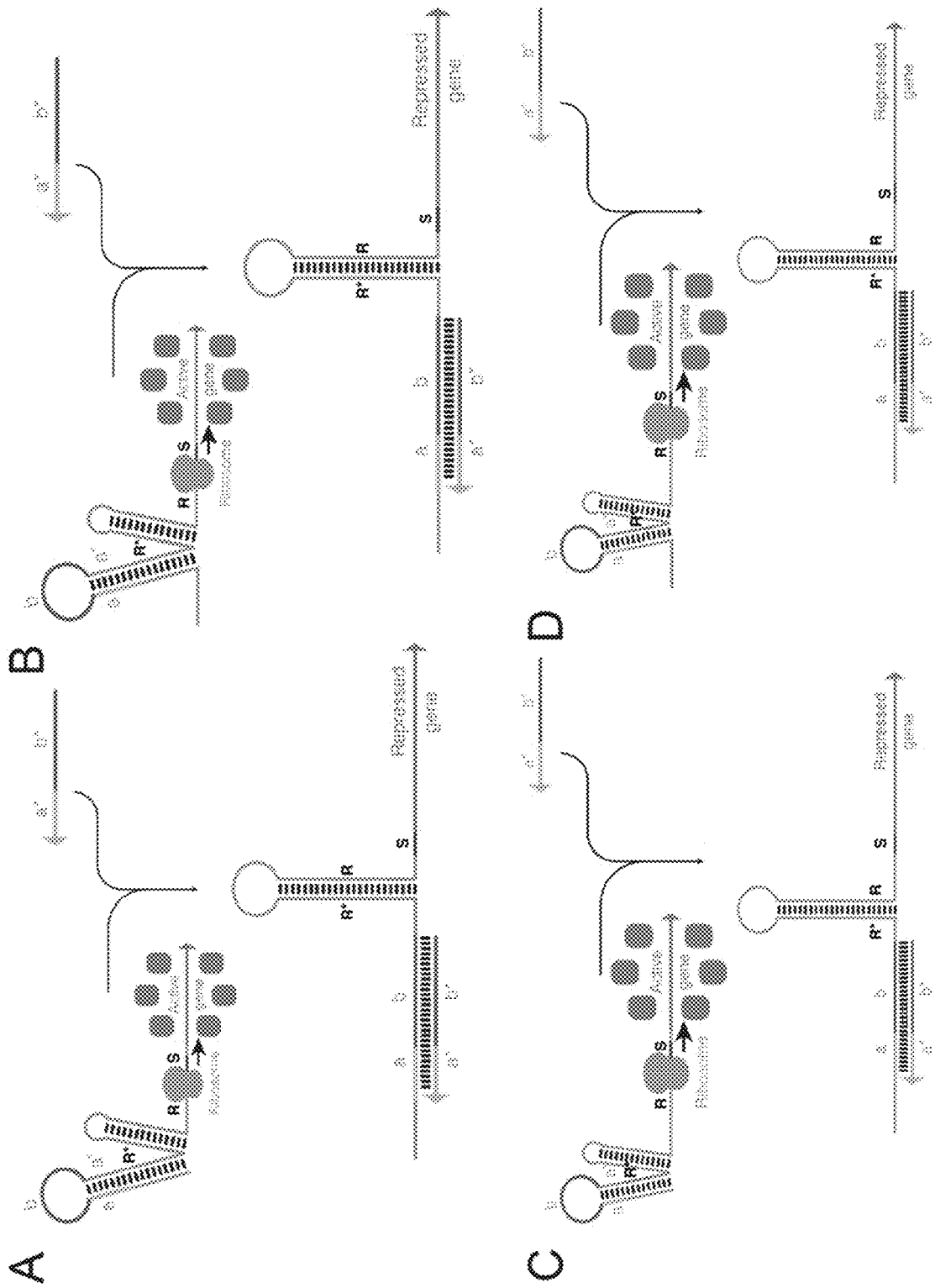
FIGS. 10A-10E illustrate different loop-mediated repressor designs. (A-D) Four different rationally designed loop-mediated repressors. RBS and RBS-complementary sites are shown in blue and labelled R and R*, respectively. Start codons are shown in purple and labelled S. (E) The data of best devices from each of those four designs. Design types are labeled A to D according to the panel above with their design.
Figures 10A, 10B, 10C, 10D, 10E:
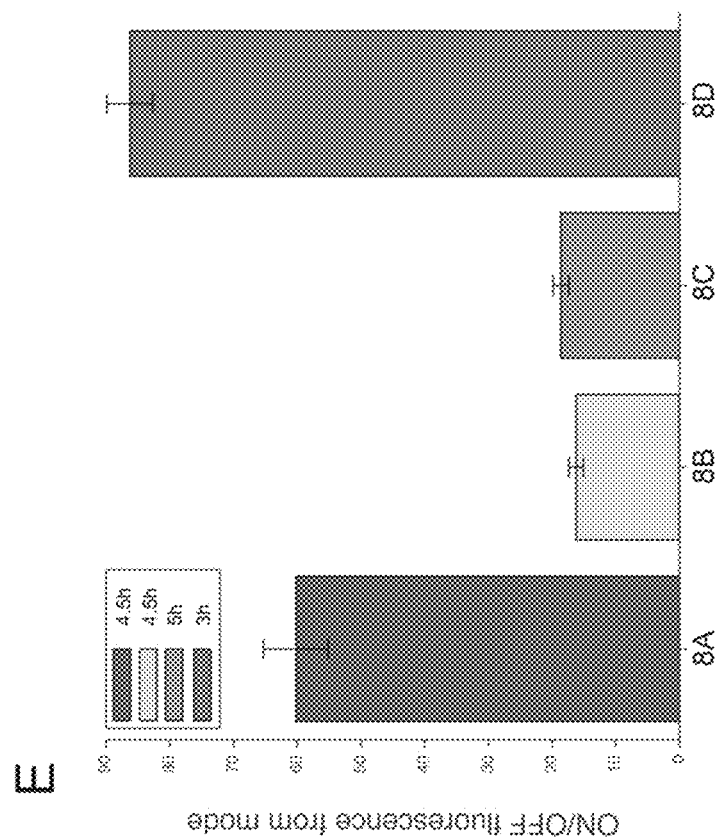

As described herein, "OR" logic circuits are synthetic nucleic acid logic circuits comprising multiple input RNA recognition sites configured such that only one input RNA needs to be bound to an input RNA recognition site for expression of the target gene to occur. OR logic circuits comprise a branched secondary structure wherein the stem-domain of the branched secondary structure comprises a ribosomal binding site and a start codon. The stem-domain is formed by the 5' and 3' ends of the branched secondary structure, and two or more arms of the branched secondary structure are located between the 5' portion and 3' portions which form the stem-domain. Each of the arms of the branched secondary structure comprises a loop domain which comprises an input RNA recognition site and the separate input RNA recognition sites of the separate arms recognize unique input RNA sequences. For example, for a 2-input OR circuit comprises a stem-domain and two arms, a first arm comprising first input RNA recognition site and a second arm comprising a second recognition site. In a 2-input OR expression, translation of the output gene is activated when either or both of two input species is expressed within the cell. When neither or none of the input RNA triggers is present, gene expression is turned off. It is envisioned that the OR logic circuit can be designed to accommodate binding of 2, 3, 4, 5, or more unique input RNA sequences at 2, 3, 4, 5, or more input RNA recognition sites, respectively, on 2, 3, 4, 5, or more arms, respectively. Some embodiments of the OR logic circuit are shown in FIG. 10A. FIG. 10A displays an RNA designed to evaluate a 2-input OR logic expression using two loop-mediated riboregulator RNA detection elements. For these circuits, the input species can be RNA trigger molecules.

Figure 13A:
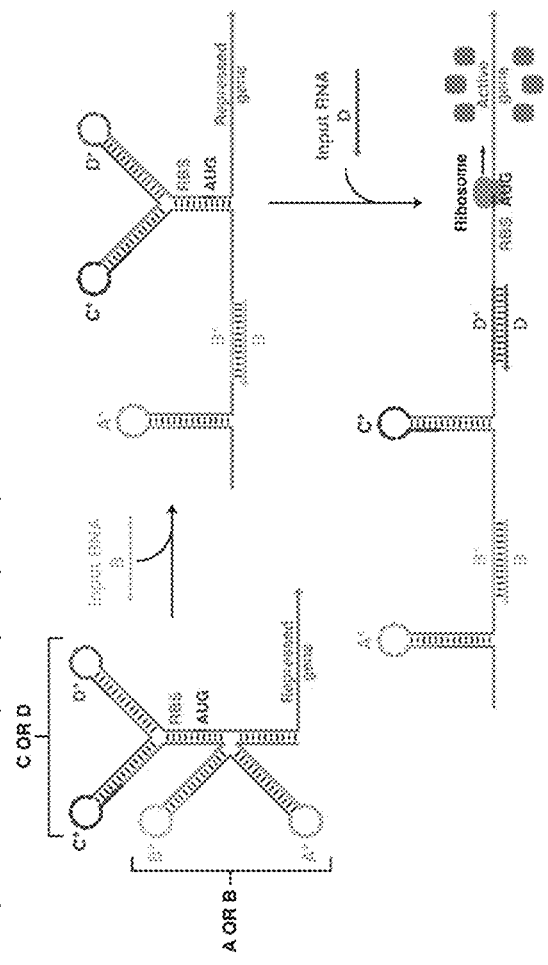
FIGS. 13A-13B illustrate exemplary conjunctive normal form (CNF) designs. (A) Detailed 2×2 (A OR B) AND (C OR D) CNF design. (B) 3×3 (A OR B OR C) AND (D OR E OR F) AND (G OR H OR I)—CNF gate RNA design.
Figure 13B:
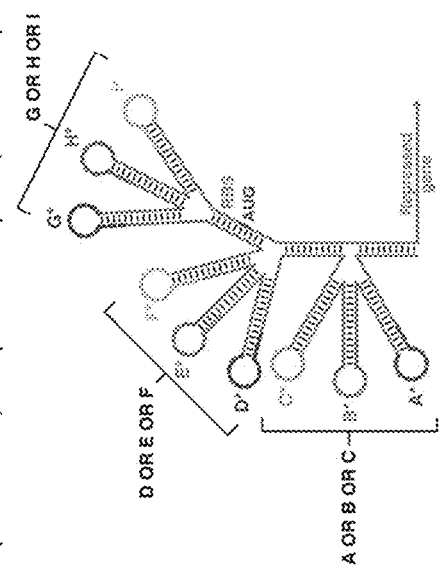

As described herein, "conjunctive normal form (CNF)" logic circuits are synthetic nucleic acid logic circuits comprising multiple input RNA recognition sites arranged in a branched secondary structure comprising two or more groups of stem-loop-domains wherein each group of stem-loop-domains comprises of two or more stem-loop-domains, wherein each stem-loop-domain comprises an input RNA recognition site. The CNF logic circuit comprises a ribosomal binding site and a start codon within the 3' most arm of the CNF logic circuit or within the '3 most group of loop-domains. The loop-domain closes to the 3' end of the branched secondary structure comprises the ribosomal binding site and the start codon. The branched secondary structure of the CNF circuit is configured such that for translation to occur, one or more input RNA must be bound to the RNA recognition sites within each of the two or more groups of loop-domains. For example, a 4-input CNF logic circuit comprises two groups of loop-domains and each group of loop-domains comprises two loop-domains. In the exemplary 4-input CNF logic circuit, one or more input RNA must be bound to the input RNA recognition site within each of the groups loop-domains. The CNF logic circuit is configured such that if any group of loop-domains does not have one or more input RNA bound to the input RNA recognition site, the translation of the repressed gene will remain OFF. In some embodiments, the CNF logic circuit comprises 2, 3, 4, 5, 6, or more groups of loop-domains. In some embodiments, the CNF logic circuit comprise groups of loop-domains comprising 2, 3, 4, 5, 6, or more loop-domains. Some embodiments of CNF logic circuits are shown in FIGS. 13A-13B. For these circuits, the input species can be RNA trigger molecules. In the exemplary embodiment shown in FIG. 13A, the CNF logic circuit comprises two groups of loop-domains, each group of loop-domains comprises two loop-domains, and the ribosomal binding site and the start codon are located within the 3' most group of loop-domains. In the exemplary embodiment shown in FIG. 13B, the CNF logic circuit comprise three groups of loop-domains, each group of loop-domains comprises three loop-domains, and the ribosomal binding site and the start codon are located within the 3' most group of loop-domains.

Advantageously, loop-mediated riboregulators as provided herein can be designed to detect a variety of different nucleic acids such as those associated with various pathogens (e.g., viruses, parasites). In certain embodiments, the target nucleotide sequence is a nucleic acid from a pathogen, where the biological sample contains or is suspected of containing the pathogen. In some case, detecting the endogenous RNA molecule is a positive indicator of a presence of a microorganism, pathogen, or gene in a sample (e.g., a biological sample). In other cases, detecting the endogenous RNA molecule is a negative indicator of a presence of a microorganism, pathogen, or gene in a sample (e.g., a biological sample). Loop-mediated riboregulators can be designed for detection of nucleic acids from any number of microorganisms or pathogens, including those that cause or are associated with human diseases. Accordingly, the methods provided herein are useful to detect any pathogen or infectious agent. Pathogens and infectious agents may comprise viruses, (e.g., single stranded RNA viruses, single stranded DNA viruses, Zika virus, HIV, hepatitis A, B, and C virus, HSV, CMV EBV, HPV), parasites (e.g., protozoan and metazoan pathogens such as Plasmodia species, *Leishmania* species, *Schistosoma* species, *Trypanosoma* species), bacteria (e.g., Mycobacteria, in particular, *M. tuberculosis, Salmonella*, Streptococci, *E. coli*, Staphylococci), fungi (e.g., *Candida* species, *Aspergillus* species), *Pneumocystis carinii*, and prions. In certain embodiments, the pathogen is a virus, and the methods can be used to detect any virus. In other embodiments, the pathogens that are detected are bacteria, fungi, or parasites. An advantage of the methods and systems described herein is that they can be applied for the detection and identification of essentially any nucleic acid-containing organism. Accordingly, the pathogen or infectious agent can be virtually any pathogen or infectious agent for which genetic information (e.g., gene sequences) is available. In other cases, the target nucleic acid is human in origin. In such cases, the methods can be employed to detect one or more target nucleic acids in a biological sample such as a biological sample obtained for forensic analysis, for genotyping, and the like.

Microorganisms and pathogens can include, without limitation, viruses (e.g., HIV, Zika virus, norovirus, Yellow fever virus) and parasites such as the malaria parasite *Plasmodium falciparum*.

In some cases, it may be advantageous to adapt the methods described herein for high-throughput, reproducible, and rapid detection, for example in a clinical setting. When loop-mediated riboregulator output is coupled to a reporter element, such as a LacZ reporter element, the riboregulator acts as a genetically encoding sensor and/or imaging probe for endogenous DNA or RNA (e.g., endogenous pathogen DNA, endogenous pathogen RNA) in a sample. For example, such loop-mediated riboregulators can be provided in a device configured for rapid, reproducible detection in a clinical setting. In some cases, the device comprises a preserved paper test article, upon which any step(s) of the method provided herein can be performed. In preferred embodiments, the paper test article is preserved by freeze-drying. The reporter element can be a reporter protein, e.g., a polypeptide with an easily assayed enzymatic activity or detectable signal that is naturally absent from the host cell. Exemplary but non-limiting reporter proteins include lacZ, catalase, xylE, GFP, RFP, YFP, CFP, neomycin phosphotransferase, luciferase, mCherry, and derivatives or variants thereof. In some embodiments of any of the aspects, the reporter protein is suitable for use in a colorimetric assay. Examples of genes encoding fluorescent proteins that may be used in accordance with the invention include, without limitation, those proteins provided in U.S. Patent Application No. 2012/0003630 (see Table 59 therein), incorporated herein by reference.

In some cases, the device is used with a portable electronic reader. In this manner, the electronic reader serves as companion technology that provides robust and quantitative measurements of device outputs. An exemplary electronic reader comprises readily available consumer components, open-source code, and laser-cut acrylic housing, and is powered by a rechargeable lithium ion battery. The electronic reader can further comprise an onboard data storage unit. In some cases, to achieve sensitive detection of toehold switch signal output, an acrylic chip that holds the freeze-dried, paper-based reactions is placed into the reader between an LED light source (570 nm) and electronic sensors. Using onboard electronics, samples can be read at a rate of 29 reads per minute. Accordingly, the portable electronic reader provides low-noise measurements of changes associated with the reporter element including changes in light transmission due to LacZ-mediated color change.

As described in the Examples section, comprehensive measurements of device-to-device crosstalk have yielded a set of 15 orthogonal loop-mediated riboregulators with under 4% cross talk.

In some cases, loop-mediated riboregulators are useful in diagnostic methods. For example, repressor systems can be used in diagnostic systems for control reactions to determine if a technician is carrying out an assay properly. For instance, the loop-mediated riboregulator can be used to detect a control RNA or DNA that is amplified along with a sample from a patient. If repressor output is low, it means that the amplification reaction was successful (provided the cell-free reaction is active). If repressor output is high, it means that the amplification reaction failed but that the cell-free diagnostic stage was successful. Similarly, an activating loop-mediated riboregulator can also be used to detect a control RNA to determine if the cell-free reaction is functional when amplification is successful.

Articles of Manufacture

In another aspect, the present invention provides articles of manufacture useful for detecting a pathogen or identifying a particular strain or species of pathogen. In preferred embodiments, the article of manufacture is a kit for detecting a pathogen such as a virus, where the kit comprises a plurality of preserved paper test articles and an electronic optical reader. Optionally, a kit can further include instructions for performing the pathogen detection and/or strain or species identification methods provided herein.

Unless defined otherwise, all technical and scientific terms used herein have the same meaning as commonly understood by one of ordinary skill in the art to which the invention pertains. All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein, the terms "approximately" or "about" in reference to a number are generally taken to include numbers that fall within a range of 5% in either direction (greater than or less than) the number unless otherwise stated or otherwise evident from the context (except where such number would exceed 100% of a possible value). Where ranges are stated, the endpoints are included within the range unless otherwise stated or otherwise evident from the context.

The present invention has been described in terms of one or more preferred embodiments, and it should be appreciated that many equivalents, alternatives, variations, and modifications, aside from those expressly stated, are possible and within the scope of the invention. The invention will be more fully understood upon consideration of the following non-limiting Examples.

EXAMPLES

Reference is now made to the following examples, which together with the above descriptions illustrate the invention in a non-limiting fashion.

This example demonstrates that, through careful design of RNA-RNA interactions, loop-mediated riboregulators have the capacity to resolve target RNAs down to the single nucleotide level in vivo and can be adapted to repress translation in response to a trigger RNA. This example also demonstrates that loop-mediated riboregulators retain their activity in cell-free systems that are compatible with paper-based diagnostics, and describes a number of novel computing schemes that employ loop-mediated riboregulators for evaluating arbitrary Boolean logic expressions.

Methods

Plasmid Construction:

Switch and trigger RNAs were expressed from separate plasmids with backbones from two vectors, pCOLADuet and pET15b, respectively. A green fluorescent protein (GFP) with an ASV degradation tag having a half-life of about 110 minutes was used as the reporter. All DNA oligonucleotides were purchased from Integrated DNA Technologies, Inc. Plasmids were assembled using the Gibson method as described previously[21]. Constructs were then cloned into the *E. coli* strain DH5a and sequenced to ensure all loop-mediated riboregulators were synthesized correctly.

Flow Cytometry Measurement and Data Analysis:

To test the loop-mediated riboregulators, competent *E. coli* was transformed with the desired combination of switch and trigger plasmids, and plated onto LB/agar plates containing the appropriate antibiotics. Antibiotics were used at the following concentrations: ampicillin (50 µg/ml), kanamycin (30 µg/ml). For flow cytometry measurements, LB medium containing antibiotics was inoculated with cells picked from individual colonies and incubated overnight with shaking in 96 deep well plates at 250 rpm, 37° C. Cells were then diluted 100-fold into fresh selective LB medium and returned to shaking at 37° C. Cells were then induced with 0.1 mM IPTG after shaking for 80 minutes. Measurements were done after inducing by IPTG for 3, 4, and 5 hours. IPTG induction led to production of T7 RNA polymerase. T7 RNA polymerase was in turn used to drive transcription of the trigger and switch RNAs, which were positioned downstream of the T7 promoter sequence.

Flow cytometry data were analyzed using custom Matlab scripts. In instrument settings, the threshold of events was set according to particle size, signals from particles with sizes far smaller than that of *E. coli* (e.g., cell debris) were removed. The *E. coli* populations had unimodal distributions in both forward (FSC) and side (SSC) scatter, and thus provided a single peak in the two-dimensional FSC versus SSC histogram. All ON/OFF ratios were calculated from the mode GFP fluorescence value of each sample as determined from the unimodal GFP fluorescence histogram.

Results and Discussion

Figure 3B:
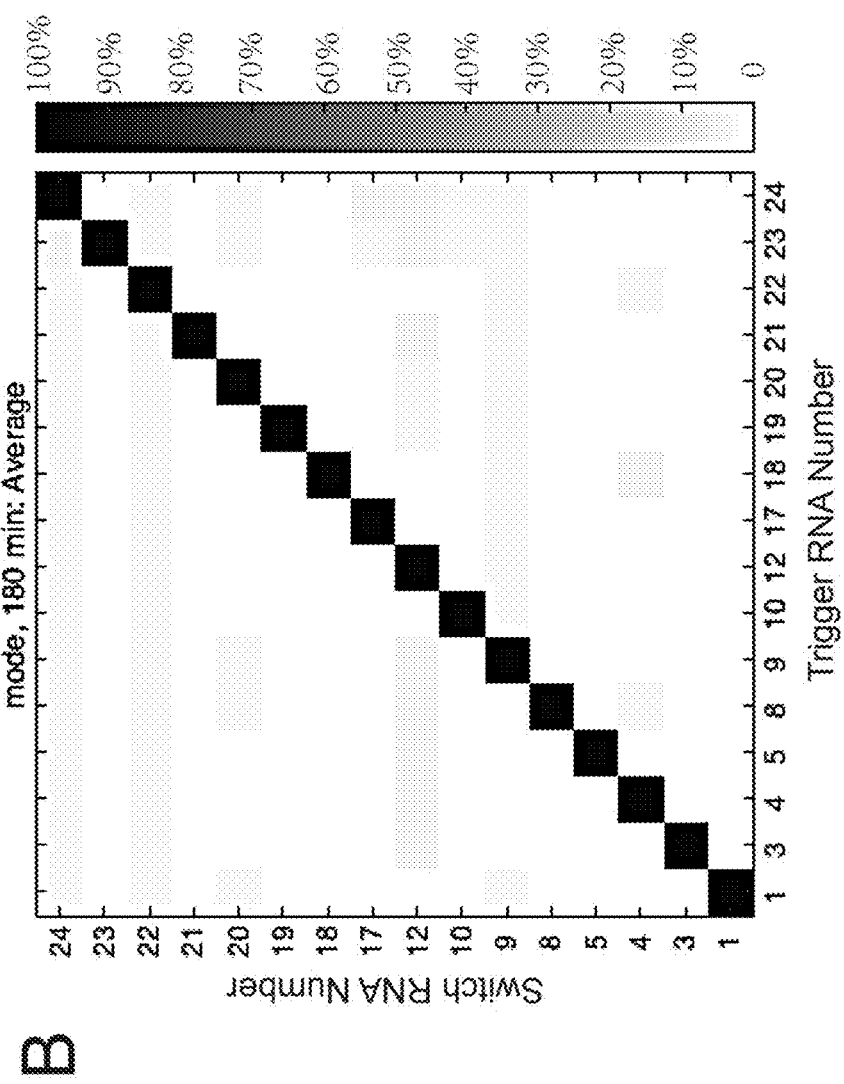

Evaluating the Orthogonality of Loop-Mediated Riboregulators:

To test the orthogonality of loop-mediated riboregulators, we selected 16 different devices having relatively high ON/OFF ratios and tested all 256 pairwise combinations of switch and trigger RNAs. We used flow cytometry to quantify GFP output from all switch-trigger combinations in triplicate measurements. FIG. 3A shows the ON/OFF ratios from the mode GFP fluorescence value of switch #1. These ON/OFF ratios were calculated by dividing the GFP fluorescence obtained from different switch-trigger combinations by the cell autofluorescence. The output GFP fluorescence from switch #1 with its cognate trigger is much stronger than with other triggers. Compared with cell autofluorescence, non-cognate pairs show virtually no difference in output GFP signal, which demonstrates that the loop-mediated riboregulator has almost no leakage. Crosstalk was calculated by dividing the GFP fluorescence obtained from a non-cognate trigger and a given switch RNA by the fluorescence of the switch in its triggered state (FIG. 3B).

The full set of 16 switches show less than 4% crosstalk, which makes them second largest set of orthogonal riboregulators reported to date[21]. Their crosstalk levels are slightly higher than the crosstalk of 18 toehold switches, which provided crosstalk below 2%. The higher crosstalk of loop-mediated riboregulator results from the lower average ON state expression levels for the 16 designs compared to the toehold switch library.

Figure 4:
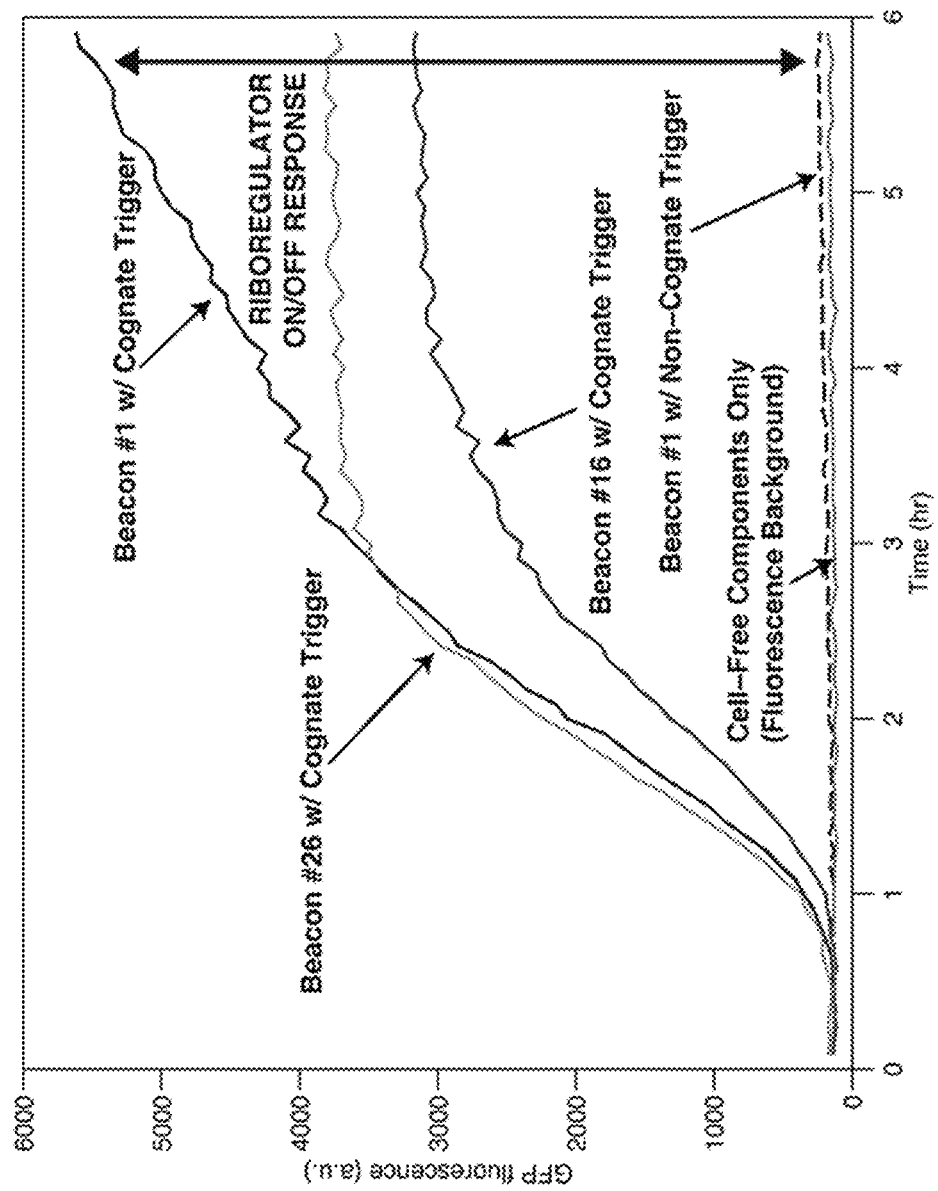
FIG. 4 demonstrates cell-free performance of loop-mediated riboregulators. Five different cell-free reactions were carried out using different combinations of transcribed RNAs. Loop-mediated #1 with a non-cognate trigger (blue dashed) displays fluorescence levels nearly the same as the cell-free components alone (gray solid). Three loop-mediated riboregulators, including #1 (blue solid), displayed strong GFP fluorescence in the presence of their cognate RNAs.

We evaluated the performance of loop-mediated riboregulators in cell-free, liquid-phase reactions (NEB Inc., PURExpress In vitro Protein Synthesis Kit). Plasmid DNA was used as the template for transcription of the trigger and switch RNAs and production of the output GFP reporter was monitored over time using a plate reader at a temperature of 37° C. FIG. 4 displays this time course fluorescence data from a set of five different samples. The intrinsic fluorescence of the cell-free system is shown as the gray curve and the reaction with loop-mediated #1 with a noncognate trigger displays a slight increase in fluorescence (dashed blue curve), demonstrating the low leakage for the loop-mediated riboregulators. When the loop-mediated #1 switch RNA is expressed along with its cognate RNA, fluorescence increases sharply (blue curve) and continues to build over the 6 hours of the experiment. Additional measurements with two other loop-mediated riboregulators with their cognate triggers also display strong GFP fluorescence output over time. We also tested the loop-mediated riboregulators in paper-based cell-free reactions[24]. We found that these riboregulators outputting lacZ as the reporter protein were able to generate clear color changes from yellow to purple through cleavage of a chlorophenol red-b-D-galactopyranoside substrate. As a result, it is expected that loop-mediated riboregulators will be fully compatible with paper-based diagnostics.

Stem Variants of Loop-Mediated Riboregulators:

Toehold switches add at least three amino acids between the start codon and the linker region of the regulated gene, which could have deleterious effects on the final output protein. Importantly, these extra three amino acids are encoded by the sequence of the trigger RNA that must directly replace these base pairs in the stem of the switch RNA. In contrast, for loop-mediated riboregulators, the early residues in the output gene do not directly interact with the trigger RNA and are disrupted through the crowbar-like interaction mechanism. As a result, the sequence of the trigger RNA can be completely decoupled from that output protein for loop-mediated riboregulators. However, there are 6 nucleotides located after the start codon in loop-mediated riboregulator to help maintain the system at OFF state when no cognate trigger RNA appears. We term this 6-nt a 'clamp' as it is designed to clamp down on leakage from the devices. We hypothesized that since the clamp does not interact directly with the trigger RNA, it should be possible to use the first 6 nucleotides of any gene as a successful clamp. To test this hypothesis, we designed four variant switches based on loop-mediated riboregulator #1. These four switches have the same sequence as #1 except inside the clamp region where the sequences are randomly designed. Then we transformed each switch with cognate trigger #1 and with one non-cognate trigger into *E. coli* and measured the GFP output after inducing by IPTG. The ON/OFF ratios from the mode GFP fluorescence value measured by flow cytometry are shown in FIG. 5A.

Figures 5A, 5B, 5C:
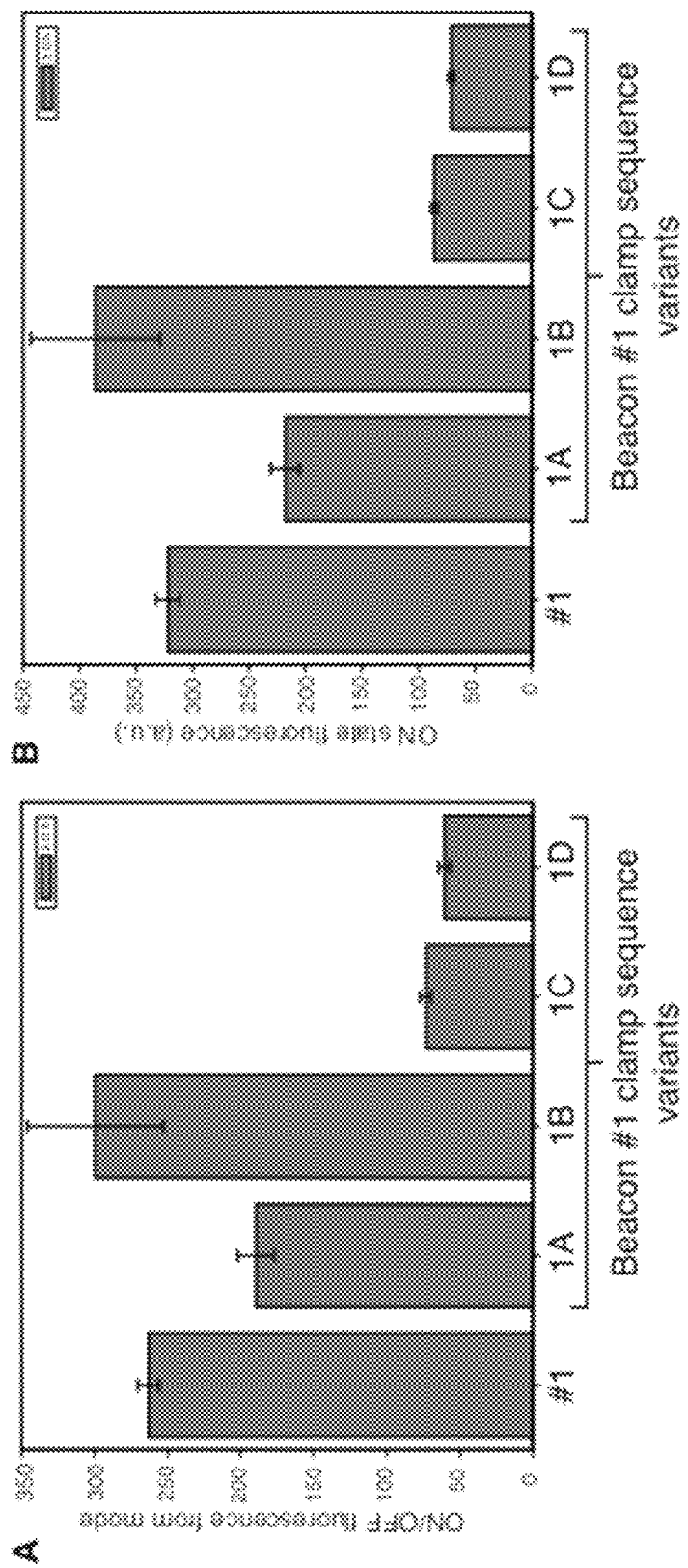
FIGS. 5A-5C are graphs demonstrating loop-mediated riboregulator clamp variants. (A) ON/OFF ratios for the four switches designed from loop-mediated riboregulator #1. All four switches have the same cognate trigger; ON states were measured from cognate pairs of switch and trigger; OFF states were measured from non-cognate pairs of switch and trigger. (B) ON state/Cell autofluorescence ratios for the four switches designed from loop-mediated riboregulator #1. ON states were measured from cognate pairs of switch and trigger. (C) OFF state/Cell autofluorescence ratios for the four switches designed from loop-mediated riboregulator #1. OFF state were measured from non-cognate pairs of switch and trigger.

As shown in FIG. 5A, although variance exists in the output signals of each switch-trigger combination, yet all systems are effectively turned on with ON/OFF >50. Based on FIGS. 5B and 5C, output variance results from ON state variations, since all OFF states are almost the same. The high ON/OFF ratios indicate that clamp sequences can be modified and still maintain good riboregulator performance. The capacity to change the clamp sequence demonstrates that the loop-mediated riboregulators are quite modular, which should enable them to be incorporated into more complex synthetic gene networks.

| | RNA Sequence |
|---|---|
| BR_6clamp_act_<br>N001_stem_bot_<br>variants_N001 | GGGUCGUGCUAUUUCACAUCUCCUAAGUUUCCGUAUUCUGUGAAGCCC<br>UAGGGUCCGAUACAGAAACAGAGGAGAUGACAAAUGACACGAAACCU<br>GGCGGCAGCGCAAAAGAUG (SEQ ID NO: 49) |
| BR_6clamp_act_<br>N001_stem_bot_<br>variants_N002 | GGGCUUAUGUAUUUCACAUCUCCUAAGUUUCCGUAUUCUGUGAAGCC<br>CUAGGGUCCGAUACAGAAACAGAGGAGAUGACAAAUGAAUAAGAACC<br>UGGCGGCAGCGCAAAAGAUG (SEQ ID NO: 50) |
| BR_6clamp_act_<br>N001_stem_bot_<br>variants_N003 | GGGUCGUUGUAUUUCACAUCUCCUAAGUUUCCGUAUUCUGUGAAGCC<br>CUAGGGUCCGAUACAGAAACAGAGGAGAUGACAAAUGGAACGAAACC<br>UGGCGGCAGCGCAAAAGAUG (SEQ ID NO: 51) |
| BR_6clamp_act_<br>N001_stem_bot_<br>variants_N004 | GGGCUUGUCUAUUUCACAUCUCCUAAGUUUCCGUAUUCUGUGAAGCCC<br>UAGGGUCCGAUACAGAAACAGAGGAGAUGACAAAUGAACAAGAACCU<br>GGCGGCAGCGCAAAAGAUG (SEQ ID NO: 52) |
| Trigger | GGGCCAGUGACUUGUCACUGGGAACGGACCCUAGGGCUUCACAGAAU<br>ACGGAAACGAC (SEQ ID NO: 53) | qRT-PCR Tests of Loop-Mediated Riboregulators:

Rho-independent transcriptional terminators in prokaryotes feature long stem-loop structures that interfere with the progress of the RNA polymerase to halt transcription. While toehold switches have relatively weak stems that are 18-bp long including a 3-nt bulge, loop-mediated riboregulators have far stronger stems up to 33-nts in length. Given the strength of this stem, we hypothesized that transcriptional regulation could be playing a role in the ultralow leakage we observed in the loop-mediated riboregulators. Thus, we performed qRT-PCR studies on both loop-mediated riboregulator #1 and toehold switch N56 to determine the concentrations of the switch RNAs in vivo. We used 16s rRNA as the internal marker for the measurements. At first, we induced the expression of both cognate and non-cognate pairs of switch and trigger for loop-mediated riboregulator #1 and toehold switch N56 using three colonies for each. After induction for 3 hours, we performed RNA minipreps to extract cellular RNAs and used reverse transcription to generate cDNA. The cellular RNAs in these experiments were generated using T7 RNA polymerase in *E. coli* BL21 Star DE3.

Figure 6:
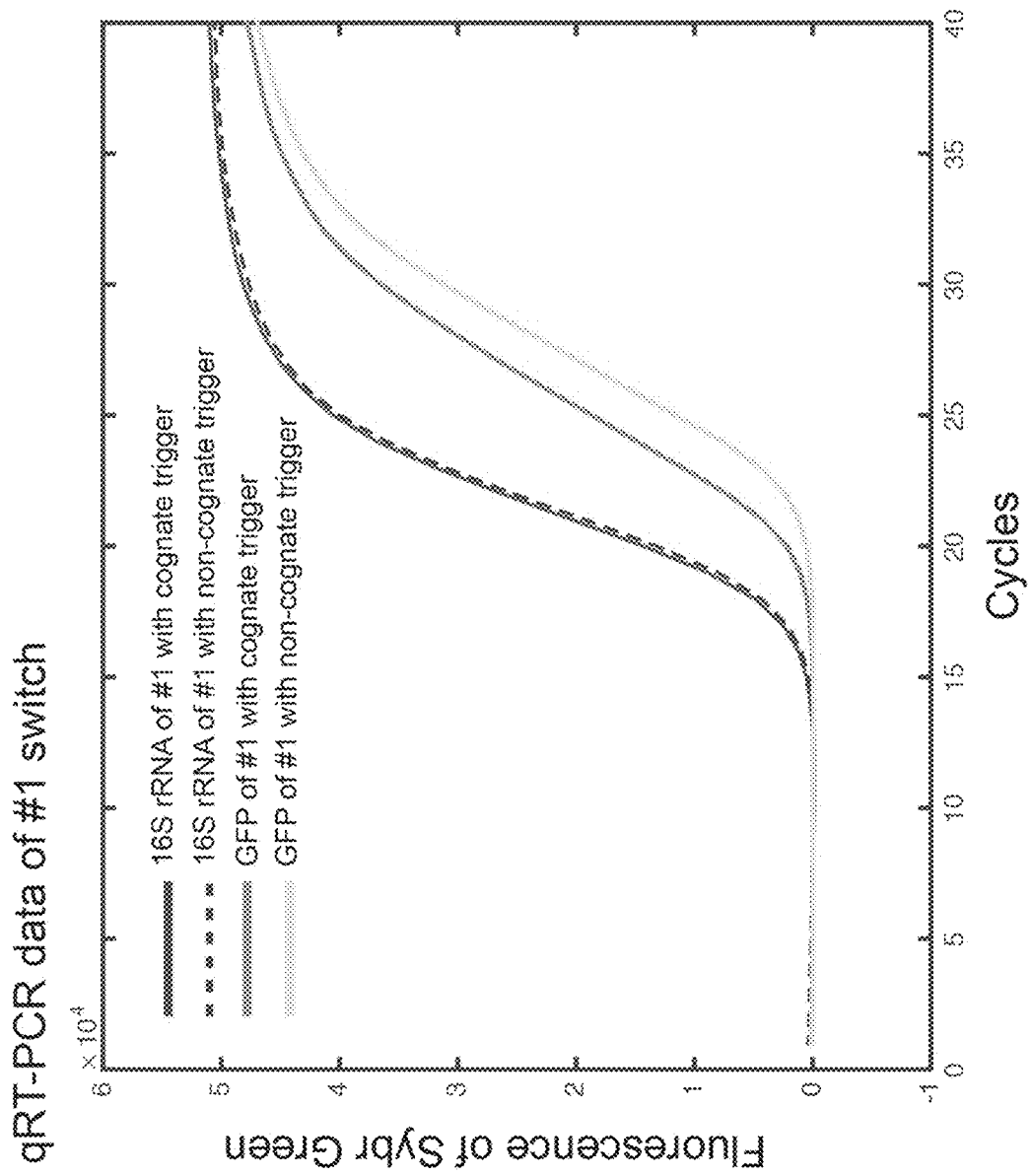
FIG. 6 presents quantitative RT-PCR (qRT-PCR) data of loop-mediated riboregulator #1. qPCR curves of SYBR Green signal for the housekeeping gene 16S rRNA and GFP transcripts are measured for the switch with both cognate and non-cognate triggers.

The signal curves of SYBR Green from loop-mediated riboregulator #1 are shown in FIG. 6. Expression levels of the housekeeping rRNA are stable for both cognate and non-cognate pairs, but GFP mRNA expression levels are significantly different. For the cognate RNAs, CT value of GFP cDNA is 18, but it is 20 for non-cognate pair (Table 2). For toehold switch N56, CT values for both cognate and non-cognate pairs are 18. The relative gene expressions of different qPCR templates are shown in Table 2. According to Table 3, toehold switch N56 does not exhibit regulation at the transcriptional level since the cognate and non-cognate pairs show the same expression levels of GFP transcripts. However, for loop-mediated riboregulator #1, cells expressing the cognate trigger/switch pair have 4 times more GFP transcripts than those expressing non-cognate RNA since the difference is CT values for both conditions ($-\Delta\Delta CT$) was $-2$ and corresponds to an overall transcript level difference of $2^{-2}$. The relative gene expression levels indicate that loop-mediated riboregulators employ regulation at the transcriptional level. As shown in Table 3, the CT values of GFP transcripts for the cognate pair of loop-mediated riboregulator #1 and toehold switch N56 are the same, indicating no regulation in transcriptional level occurs when cognate pair of switch and trigger appear.

TABLE 2

| | Average CT Values | | | |
|---|---|---|---|---|
| Average CT value | Beacon #1 with Cognate Trigger | Beacon #1 with Non-Cognate Trigger | Toehold N56 with Cognate Trigger | Toehold N56 With Non-Cognate Trigger |
| 16S rRNA | 17 | 17 | 17 | 17 |
| GFP mRNA | 18 | 20 | 18 | 18 |

TABLE 3

| | Relative Gene Expression | | |
|---|---|---|---|
| | ΔCT | -ΔΔCT | Relative Gene Expression |
| Beacon #1 With Cognate Trigger | 1 | 0 | 1 |
| Beacon #1 With Non-Cognate Trigger | 3 | -2 | 0.25 |
| Toehold N56 with Cognate Trigger | 1 | 0 | 1 |
| Toehold N56 with Non-Cognate Trigger | 1 | 0 | 1 |

These data demonstrate that a fraction of the trigger RNAs are able to bind to the newly transcribed switch RNA before the formation of the complete stem-loop structure. This binding will facilitate the transcription of the whole switch RNA including the downstream GFP gene. However, for non-cognate switch and trigger RNAs, the trigger RNA cannot bind to the newly transcribed switch RNA and a fraction of the active RNA polymerases will be displaced from the DNA due to the formation of the stable stem-loop structure. This finding demonstrates that loop-mediated riboregulators can exhibit both transcriptional and translational level regulation. To our knowledge, this is the first riboregulator reported that exploits regulation at both the transcriptional and translational levels. It is important to note that this transcriptional regulation was observed using T7 RNA polymerase, a highly active phage-derived polymerase. The behavior of the loop-mediated riboregulator may change depending on the polymerase used, the promoter driving transcription, and the RNA sequences surrounding the switch RNA module. Nevertheless, combined post-transcriptional and transcriptional regulation should be possible using similar mechanisms for other RNA polymerases using similar loop-mediated riboregulator designs.

SNP Detection with Loop-Mediated Riboregulators:

As mentioned above, loop-mediated riboregulators should be more sensitive to trigger RNA sequence changes than toehold switches, even down to the single-nucleotide level in vivo or in vitro. To test this hypothesis, we simulated computationally the interaction between switch and trigger RNAs when there is a SNP site at different positions of the trigger RNA. We also shortened the trigger length to 24-nts (down from 31-nts) and reduced the complementary region between the trigger RNA from 21-nts to 14-nts. Both these modifications helped increase the specificity of the sensor by reducing the free energy difference between the switch RNA and switch/trigger complex. The overall reaction between the trigger and switch during SNP detection disrupts 18 base pairs at the bottom of the stem while forming 14 new base pairs through binding to the loop region, yielding a net loss of 4 base pairs upon trigger binding. The extra energy driving the cognate interaction arises from the increase in entropy that occurs when the 5' and 3' are driven apart during trigger RNA binding. Binding of a trigger that differs by a single nucleotide will yield a net loss of 5 base pairs, an increase of 20%. In contrast, toehold switches require at least 6 new base pairs to form to provide readily detectable gene expression[21] and thus exhibit much less sensitive thermodynamics. We used the NUPACK nucleic acid sequence design package to generate the binding probability of each SNP mismatch, and then selected designs with the highest sensitivity to SNP site of the trigger RNA as shown in FIG. 7A.

Figures 7A, 7B:
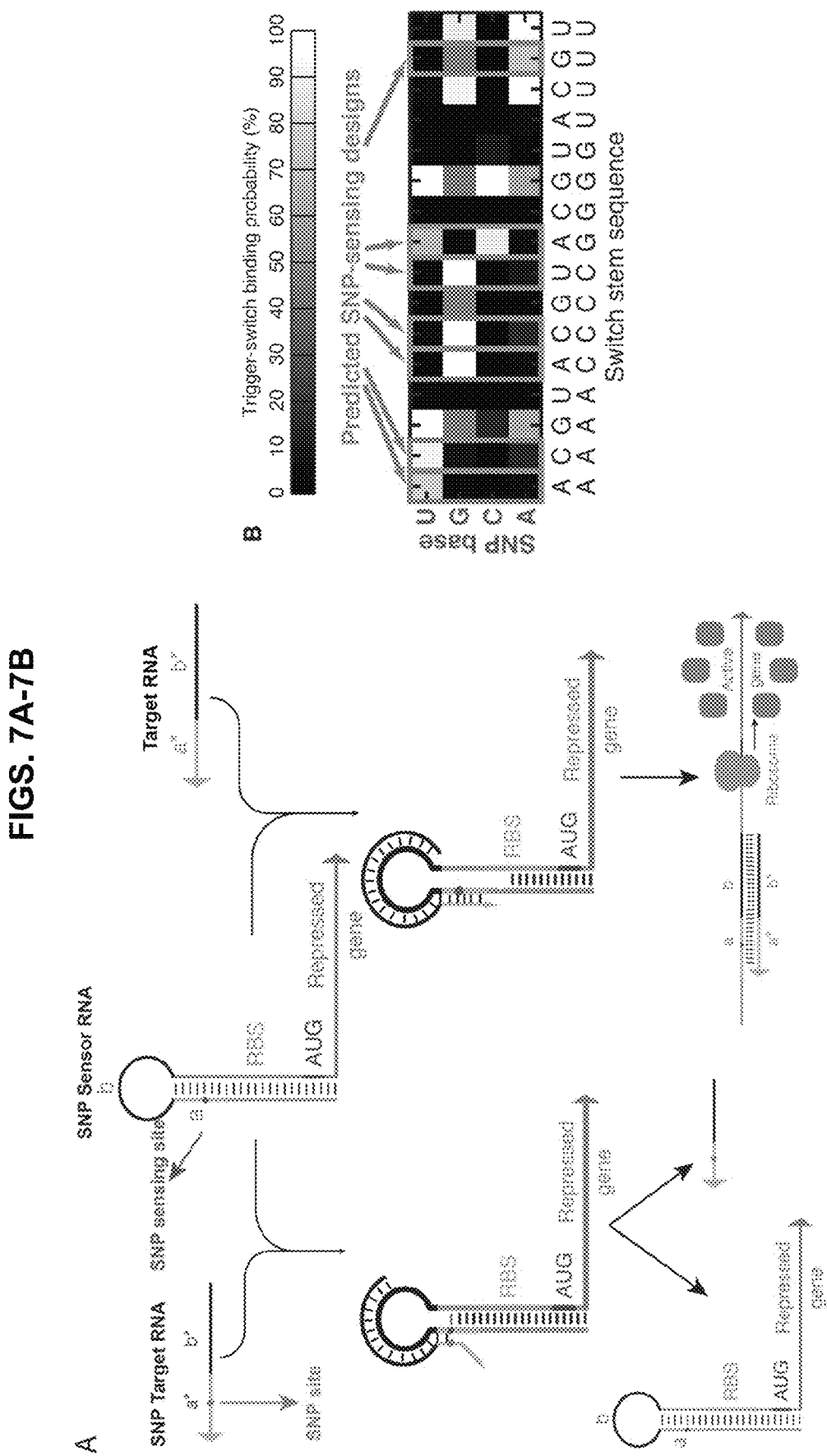
FIGS. 7A-7B illustrate SNP design of loop-mediated riboregulators. (A) Schematic of SNP-sensing design. (B) Predicted SNP-sensing designs and binding probability.

In the design shown in FIG. 7A, the SNP sensing site is located in the middle of the 10-bp binding domain on the stem. When a mismatch between trigger and switch RNA occurs at this location, the output signal is predicted to be significantly depressed. Then, we used NUPACK to generate the trigger-switch binding probability with different bases at the SNP site and the site opposite in the stem. The result of these simulations for the 16 potential combinations of bases is shown in FIG. 7B.

To validate the design shown in FIG. 7A, we constructed separate plasmids for expressing four SNP triggers that differed at only a single location in sequence with the bases A, C, G, and U. We then designed four different SNP sensors derived from loop-mediated riboregulator #1 optimized for detecting each SNP trigger. We found that all four SNP sensors demonstrated increased GFP output response when interacting with their cognate SNP trigger compared to the other three non-cognate SNP triggers. We show the output response in terms of ON/OFF GFP fluorescence from the best two SNP sensors that detected the base G (FIG. 8A) and C (FIG. 8B) at the trigger SNP site.

Figures 8A, 8B:
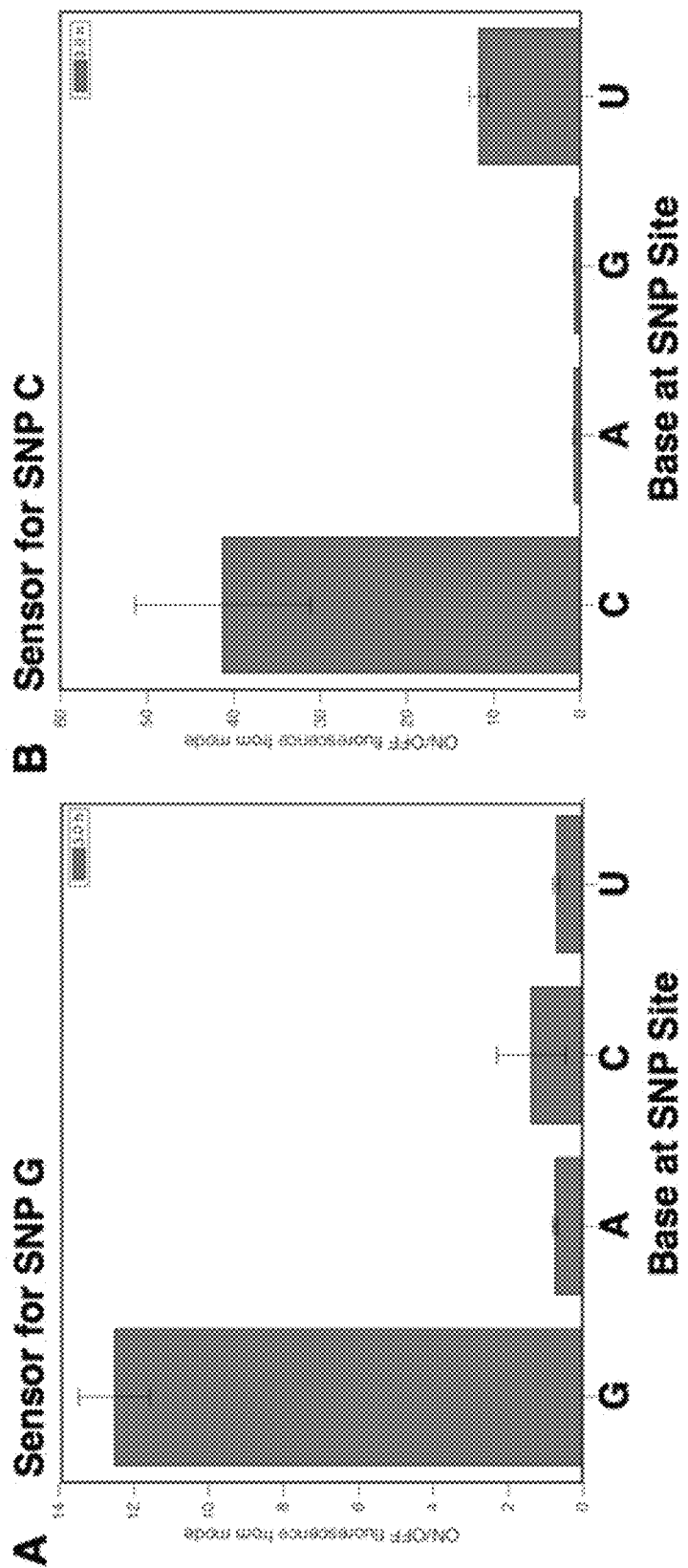
FIGS. 8A-8B demonstrate ON/OFF performance of SNP sensing loop-mediated riboregulators. (A) SNP sensor from switch #1 for sensing TC: The base G is located at the SNP sensing site and its cognate trigger TC has C at the SNP site. The cognate pair of RNAs shows much stronger GFP output. Output for the TU is also substantial, as a result of G-U wobble pairing. (B) SNP sensor from switch #1 for sensing TG: The base C is located at the SNP sensing site and its cognate trigger TG has a G at the SNP site. TG provides approx. 10-fold increase in GFP output compared to the other three triggers differing by only one nucleotide.

In FIG. 8A, the SNP sensor for G shows the best discrimination toward the target with am approximately 10-fold increase in GFP output for the cognate SNP trigger (FIG. 8B). Non-cognate SNP triggers show almost no signal increase compared to levels obtained from a trigger with a completely unrelated RNA sequence (the OFF state of the ON/OFF ratio). In FIG. 8B, out the 4 SNP sensor and trigger combinations, two combinations have substantial ON/OFF ratios. The one with highest ON/OFF ratio is from cognate pair of trigger and switch. The other one with lower ON/OFF ratio results from G-U wobble pair, which has very similar binding energy compared to the canonical G-C base pair.

Additional studies are underway to further improve the sensitivity of these systems and reduce the signal leakage observed for devices such as those in FIG. 8B. In particular, we expect that gene expression from the non-cognate SNP triggers can be substantially reduced by increasing the stem length of the switch RNAs to make stem opening by the off target RNAs more thermodynamically unfavorable. Furthermore, we are systematically varying the location of the SNP and the sizes of the domains within the switch RNA in order to enhance the degree of SNP discrimination.

| | RNA Sequence |
|---|---|
| AC6N1_L24_N5_SNPvG_hpin (Sensor for G nucleotide) | GGGUCUAUCUAUUUCACAUCUCCUAAGUUUCCGUAUUCUGUGAAGCCCUAGGGUCCGAUACGGAAACAGAGGGAGAUGACAAAUGAAUAGAAACCUGGCGGCAGCGCAAAAGAUG (SEQ ID NO: 54) |
| AC6N1_L24_N5_SNPvC_hpin (Sensor for C nucleotide) | GGGUCUAUCUAUUUCACAUCUCCUAAGUUUCGGUAUUCUGUGAAGCCCUAGGGUCCGAUACCGAAACAGAGGGAGAUGACAAAUGAAUAGAAACCUGGCGGCAGCGCAAAAGAUG (SEQ ID NO: 55) |
| AC6N1_L24_N5_SNPvA_trig (Trigger with A nucleotide) | GGGCUUCACAGAAUACAGAAAC (SEQ ID NO: 56) |
| AC6N1_L24_N5_SNPvC_trig (Trigger with C nucleotide) | GGGCUUCACAGAAUACCGAAAC (SEQ ID NO: 57) |
| AC6N1_L24_N5_SNPvU_trig (Trigger with U nucleotide) | GGGCUUCACAGAAUACUGAAAC (SEQ ID NO: 58) |
| BR_6clamp_act_N001_trig (Trigger with G nucleotide) | GGGCCAGUGACUUGUCACUGGGAACGGACCCUAGGGCUUCACAGAAUACGGAAACGAC (SEQ ID NO: 59) |

Figures 9A, 9B, 9C, 9D:
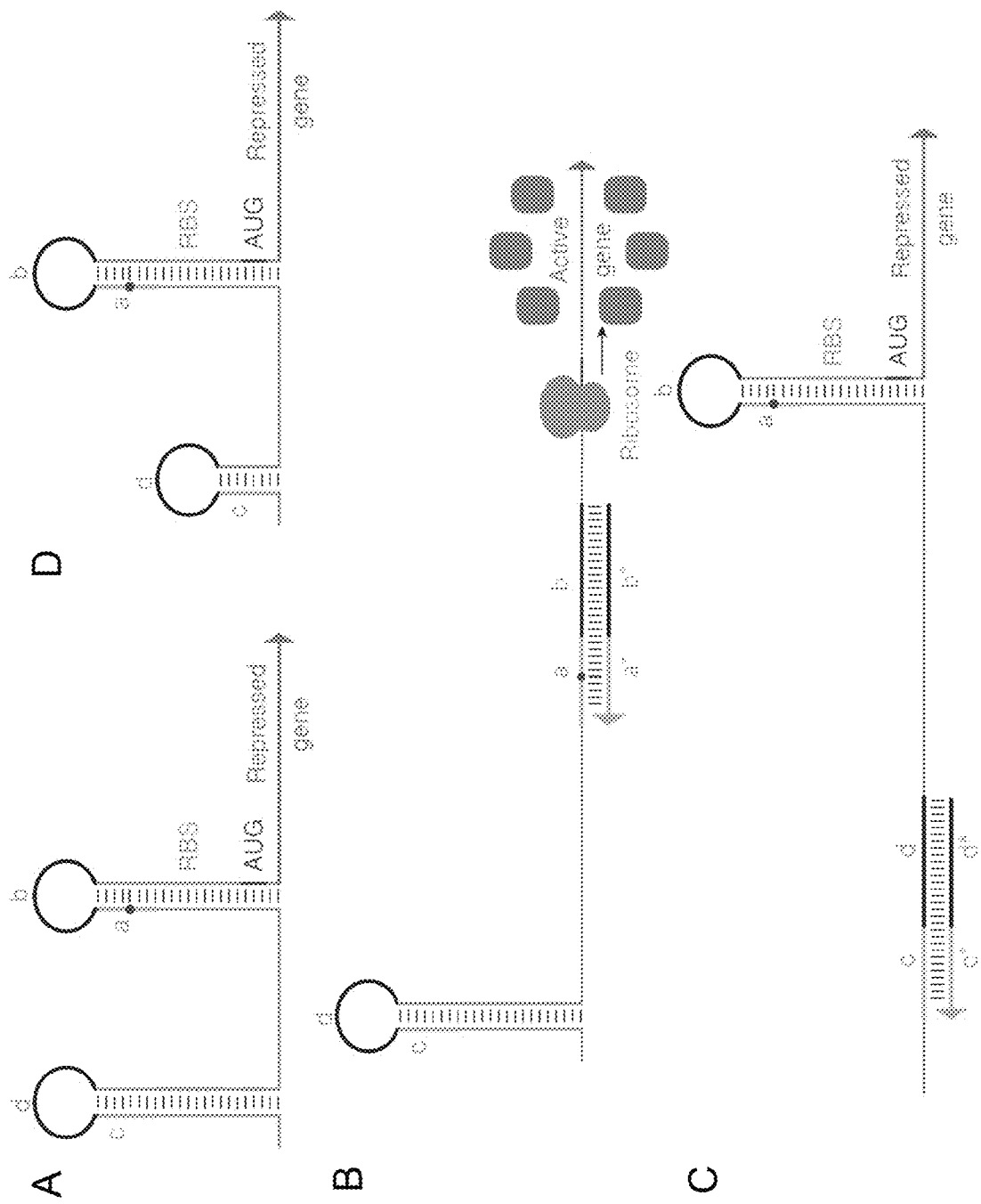
FIGS. 9A-9D are schematics illustrating two exemplary hairpin SNP sensor designs. (A) Two hairpin SNP sensor design. (B) Mutated trigger turns on the expression of reporter gene. (C) The wild-type trigger disrupts the first hairpin but the system is still in its OFF state. (D) Design with a shorter first hairpin to avoid premature transcriptional termination.

An Improved Design for SNP Detection Using Riboregulators:

To further improve the performance of the SNP-sensing riboregulators, we developed a novel riboregulator design that exploits competitive binding to decrease the likelihood of a non-cognate trigger RNA activating the riboregulator. As shown in FIG. 9A, these improved SNP-sensing designs consist of two (or more) hairpins upstream of the output gene that are both capable of binding trigger RNAs. The first hairpin, located closer to the 5' end of the switch RNA, is complementary to wild-type (WT) target, which is not intended to activate expression of the output gene. This first hairpin does not have an RBS sequence nor does it have a start codon, so it is incapable of initiating gene expression. The second hairpin is a loop-mediated riboregulator designed to activate in response to the desired SNP trigger RNA (FIG. 9B). The resulting two hairpin switch RNA thus constitutes a competitive binding system in which the WT target will preferentially bind to the first hairpin, since it is thermodynamically more favorable, and not elicit any output from the riboregulator as the second hairpin will remain intact (FIG. 9C). In contrast, the SNP target will preferentially bind to the second hairpin since it is more thermodynamically favorable to do so compared to the first hairpin. This binding event will in turn activate expression of the output gene (FIG. 9B). Considering the potential for regulation at the transcriptional level, it is also possible to design a shorter first hairpin as long as it provides the adequate competition for binding the target RNA compared to the second hairpin (FIG. 9D).

Importantly, this competitive binding system can be implemented using any riboregulator system, such as toehold switches and STARs. Improved sequence discrimination capabilities can be obtained by adding more "decoy" hairpins like the first hairpin upstream of the 3' most riboregulator. For example, in order to detect a trigger RNA that contains the nucleotide C at the target location, one could add three decoy hairpins upstream of the riboregulator for the SNP C trigger. These decoy hairpins would be optimized to preferentially bind the SNP A, SNP U, and SNP G triggers and reduce the probability that they would be able to activate the SNP C sensing riboregulator. In addition, the decoy hairpins need not necessarily be hairpins and could simply be single-stranded binding sites of off-target sequences, provided they have similar affinities for the target RNAs as the riboregulator module downstream.

Loop-Mediated Repressors:

The riboregulators described above are designed for turning on expression of regulated genes by binding with trigger RNA. We term riboregulators that have such function "activators". However, to precisely control gene expression and make more complex genetic circuits, riboregulators termed "repressors" has been studied by many researchers[18]. For repressors, gene expression in the absence of a cognate trigger RNA is initially activated and thus the repressor is in its ON state. However, when the cognate trigger RNA is expressed, binding to the riboregulator turns OFF gene expression. FIGS. 10A-10B display the designs and experimental results obtained for repressors employing the same loop-mediated interaction mechanism of the loop-mediated riboregulator activators. In these repressors, the RBS domain and AUG start codon are located in a linear, single-stranded structure upstream of regulated gene. Within the hairpin structure that binds to the trigger, we rationally designed a domain that is completely complementary to the RBS domain. Thus, in the absence of the trigger, the freely exposed RBS and start codon domains of the switch RNA enable active translation of the downstream gene. However, upon binding of the trigger RNA through the loop of the hairpin, disruption of the hairpin stem frees a domain that is complementary to the RBS and causes the switch RNA to refold into a configuration in which the RBS is no longer available for binding to the ribosome and translation can no longer occur.

To weaken the transcriptional regulation of loop-mediated riboregulator, we designed a structure containing two smaller hairpins unlikely to have rho-independent transcriptional termination activity. For the designs shown in FIGS. 10A and 10B, the first hairpin is 21 nts in length and the second one is 14 nts in length. The design in FIG. 10B has a 12-nt 5' toehold domain, which is designed for enhancing the transcription of the switch RNA. For the designs in FIGS. 10C and 10D, both the first and second hairpins have 20-nt stems. The design in FIG. 10D has a 12-nt 5' toehold domain. The ON/OFF ratios from repressors having each of the four designs are shown FIG. 10E. While repressors previously reported in the literature only reach ~10-fold ON/OFF ratio[18,19,27], the loop-mediated repressors can achieve up to 90-fold reduction in gene expression and can detect arbitrary trigger RNAs.

| Riboregulator Type | Riboregulator Name | Switch RNA Sequence | Trigger RNA Sequence |
| --- | --- | --- | --- |
| TypeA | BR_rep_gen2_N003 | GGGUGAAUAGUGGAGACC GGUUUCUAUCUAUUGUAU UCUUGUUCCGAAACCGAU CUCCACUAUUCAGCUUAA GCACAAUCAGCCUCGAUU GUACUUAAGCAGAAUAGA GGAGAUAGACAAUGAACC UGGCGGCAGCGCAAAAGA UG (SEQ ID NO: 60) | GGGACCAGCCACUG GGCUGGUAUAGGAA CAAGAAUACAAUAG AUAGAAACCGAAA (SEQ ID NO: 61) |
| TypeB | BR_rep_gen2_th_N002 | GGGAUAAACUACAAAGCG ACAAUGGAGACUCGCGCU CUAUUCCAUUAUCUUAUU CUUAGCGCGAGUCUCCACU GUCGCAGACAUGUUCCAC UCCUGCUAGUGGACCAUG UCUACGACAGAGGAGACA CGGAAUGAACCUGGCGGC AGCGCAAAAGAUG (SEQ ID NO: 62) | GGGCAGCGGUAUUG ACCGCUGAGUAAGA AUAAGAUAAUGGAA UAGAGCGCGAAGA (SEQ ID NO: 63) |

-continued

| Riboregulator Type | Riboregulator Name | Switch RNA Sequence | Trigger RNA Sequence |
|---|---|---|---|
| TypeC | BR_rep_gen2_type2_N002 | GGGCAGAUAUAGGAGAUC GGUGUAGUUUAUGUGCUU UAGGUUAUACACCGAUCU CCUGUAUCUGGCGUCACUC GAACUGUCUAAAGUAGGU UAGACUGUUCGAAUGACG CAAGAUAGAGGAGACAAC GAAUGAACCUGGCGGCAG CGCAAAAGAUG (SEQ ID NO: 64) | GGGCAAGGCCUAUU GGCCUUGAGAAUAA CCUAAAGCACAUAA ACUACACCGAAA (SEQ ID NO: 65) |
| TypeD | BR_rep_gen2_type2_th_N003 | GGGAAUAAGUAGACAUGA ACAUAGGAGACCGGUGUA GUGUAGUGUAUGUAUGUA AGACACCGAUCUCCUAUG UUCACGUUCCUGGAGUCG AACAUUACGACGAAUGUU AGACUCCUGGAACGAGAA CAGAGGAGACACAUAAUG AACCUGGCGGCAGCGCAA AAGAUG (SEQ ID NO: 66) | GGGCCAUGCACAGU UGCAUGGGAACUUA CAUACAUACACUAC ACUACACCGAAU (SEQ ID NO: 67) |

RNA-Only Biomolecular Logic Systems:

Synthetic biology seeks to program cellular behavior via in vivo biological circuits that are constructed from high performance orthogonal biological components. Considerable research has been focused on designing layered circuits in which the output of circuit element in one layer is fed forward into a subsequent circuit element in the next layer[19]. However, such layered circuit designs are limited by diffusive transport within the cytoplasm, can have hard-to-control signal propagation delays, and do not exploit the potential for parallel computation achieved by natural genetic circuits. Moreover, scale-up of layered circuit designs is difficult since the orthogonality of many circuits elements is limited, and many biological components have widely varying input and output characteristics, which can be difficult to balance within the same circuit.

One promising solution to overcome these problems is through the use of RNA-based logic gates. RNA-based logic gates take advantage of predictable Watson-Crick base pairing that is more specific and programmable than protein-DNA and protein-protein interactions, and can exhibit considerably lower crosstalk through purely in silico screening[21]. Moreover, RNA-based gates are easy to scale up as result of the sequence space afforded by RNA, and enable multi-input processing within a single computational layer and thus avoid the disadvantages of layered computation schemes.

To demonstrate the capacity of loop-mediated riboregulators for in vivo logic, we have devised a number of novel strategies to incorporate loop-mediated riboregulators into computational systems for evaluating OR, AND, and conjunctive normal form (CNF) logic. FIG. 10A displays an RNA designed to evaluate a 2-input OR logic expression using two loop-mediated riboregulator RNA detection elements. In a 2-input OR expression, translation of the output gene is activated when either or both of two input species is expressed within the cell. For these circuits, the input species are RNA trigger molecules previously used to activate loop-mediated riboregulators. When neither of the input RNA triggers is present, gene expression is turned off.

Figures 11A, 11B:
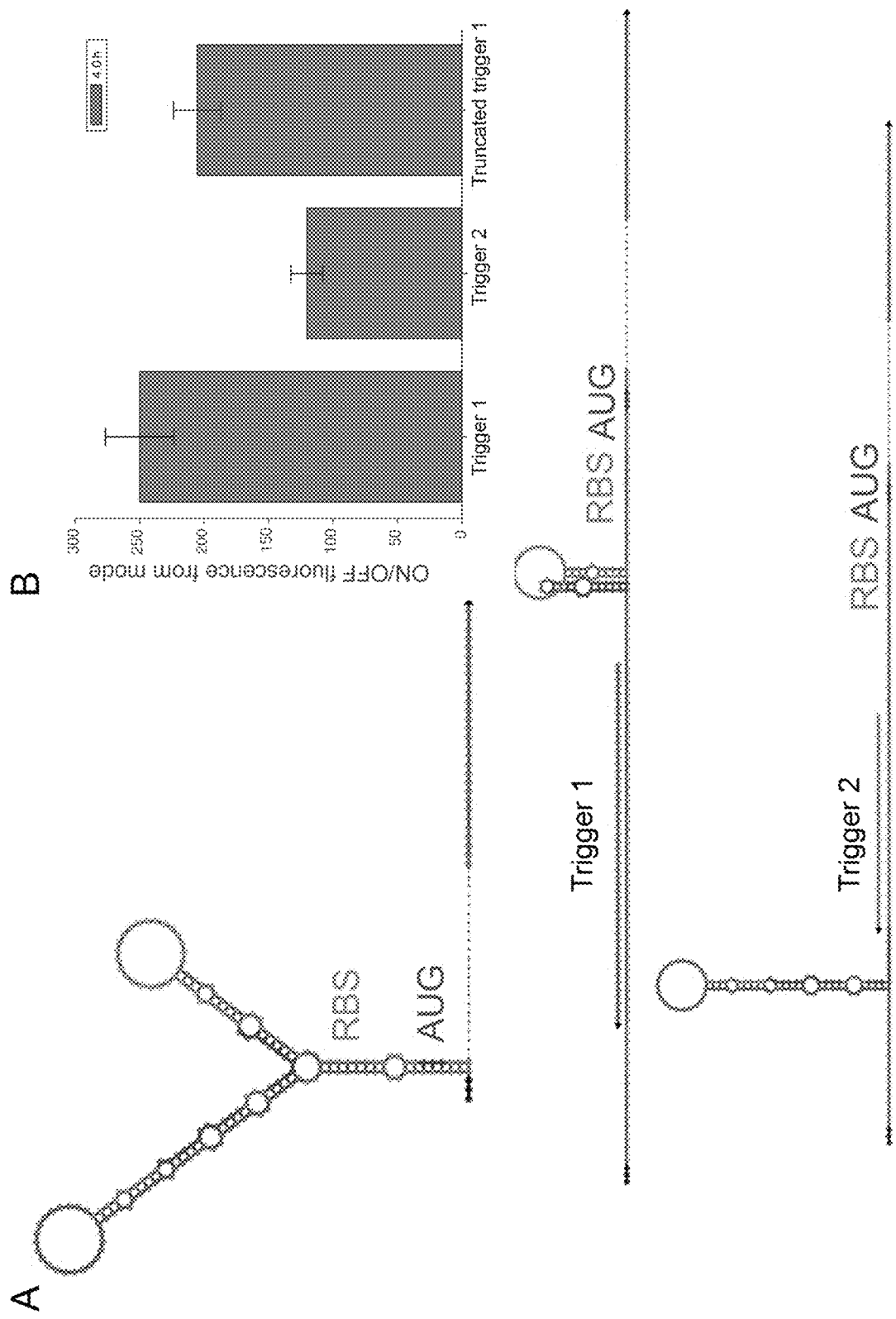
FIGS. 11A-11B illustrate exemplary 2-input 'OR' logic gate designs. (A) Detailed structures of 2-input 'OR' logic gate design. (B) ON/OFF ratio of the first 2-input 'OR' logic gate design.

We termed the RNA transcript depicted in FIG. 11A a "gate" RNA as it is designed to function as a logic gate. The logic processing element of the gate RNA consists of the Y-shaped secondary structure in which the base of the Y contains the RBS (blue) and start codon (purple) of the output gene. The left and right arms in the Y structure of the gate RNA are derived from validated loop-mediated riboregulators that can detect one of the two input RNAs. In the absence of either input RNA, the gate RNA retains its Y structure and the RBS and start codon are sequestered, preventing translation from occurring. When input RNA 1 is expressed, this RNA (red) is complementary to the left arm of the gate RNA. Consequently, binding to the left arm sequence unwinds both the left arm and the base of the Y structure (FIG. 11B). Disruption of the Y structure exposes the RBS and start codon turning on translation. When input RNA 2 is expressed, this RNA (orange) binds to the complementary right arm of the gate RNA Y structure. This binding event also causes the base of the Y to unwind and also exposes the RBS and start codon for translation (FIG. 11C). It is important to note that we have explicitly designed the base stem of the Y structure to be less thermodynamically stable than either of its arms. The decreased stability of the base stem means that it will be the second stem disrupted upon binding of the input RNA, while the opposite arm, which does not interact directly with the input RNA, will remain intact. In effect, the weak base stem ensures that the energy from input RNA binding is transmitted directly to freeing the RBS and start codon, and is not lost to unwinding either of the RNA sensing arms.

| | RNA Sequence |
|---|---|
| OrH1 Gate RNA | GGGAUUCAUUUCACAUCUCCUAAUCCAGUCGUGGAUGGGCUCUGUUUCCG UAUUCUGUGAAGCCCUAGGGUCCGAUACAGAAACAGAGCCCAUCCACGAC UGGAAUGGCUCUGUUUCAUCUUAAAGUCCUUGUAACAGUCGUCAAGACG |

| | RNA Sequence |
|---|---|
| | AAACUAAGCCAUAGAGGAGAUGACAAAUGAAUAACCUGGCGGCAGCGCA<br>AAAGAUGCGUAAAGGAGAAGAACUUUUCACUGG (SEQ ID NO: 68) |
| Trigger T1 | GGGCCAGUGACUUGUCACUGGGAACGGACCCUAGGGCUUCACAGAAUACG<br>GAAACAGAGCCCAUCCACGACUGGAGAC (SEQ ID NO: 69) |
| Trigger T8 | GGGCCAGUGACUUGUCACUGGAGCGACGACUGUUACAAGGACUUUAAGA<br>UGAAACGAC (SEQ ID NO: 70) |
| Trigger tT1 | GGGCCAGUGACUUGUCACUGGGAACGGACCCUAGGGCUUCACAGAAUACG<br>GAAACAGAGCCCAUCCACGAC (SEQ ID NO: 71) |

In order to increase the output expression from the input 1 RNA, we have also designed an RNA refolding motif shown in dark blue in FIG. 11A. This refolding motif is initially prevented from forming as it is trapped within the two arms of the Y structure of the gate RNA. However, upon binding of input RNA 1, the 5' portion of the refolding motif is exposed and is able to bind to a newly exposed toehold in the 3' portion of the refolding motif. The ensuing branch migration causes a hairpin to form between the complementary domains and in turn disrupts several base pairs originally present in the right arm of the Y structure of the gate RNA. The net effect of the refolding motif is to increase the distance between the RBS sequence and the upstream stem (orange) used for detecting input RNA 2. Previous studies have shown that increasing this distance between the RBS sequence and an upstream RNA duplex can yield substantial increases in the translational efficiency of an mRNA[21].

We tested the gate RNA shown in FIG. 11A in *E. coli*. As shown in FIG. 11B, the ON/OFF ratios for the 2-input gate where the OFF state expression level was obtained with a non-cognate input RNA. Expression of either of the cognate input RNAs yielded at least 100-fold increases in GFP expression. We also measured output using a truncated input RNA 1, which binds only partially to the stem of the left stem of the Y structure. We found that the shortened input RNA 1 led to a ~20% reduction in GFP output likely as a result of its reduced thermodynamic free energy for binding to the left arm.

We have also designed gates for evaluating AND logic. A 2-input AND gate design is shown in FIG. 12A. For 2-input AND logic, the logic expression evaluates as TRUE or ON only when both input species are expressed in the cell. The absence of one or both of the inputs corresponds to a logical FALSE or OFF state. The operation of the AND gates revolves around the fact that, as we increase the length of the stem of a stem-loop structure, we will eventually reach a stem length where the input trigger RNA is simply unable to disrupt the stem. 2-input AND gate RNAs also include Y-shaped secondary structure; however, in this case, the RBS and start codon domains are now located in the right arm of the Y structure. Like the 2-input OR gate, the left and right arms of the gate RNA are both derived from loop-mediated riboregulators and are used to detect one of the input RNAs. In the absence of any input RNAs, the RBS and start codon are strongly sequestered within the Y-structure and thus no translation occurs. When input RNA 2 (orange) is expressed alone, the corresponding right arm of the gate RNA contains such a long stem that it is unable to hybridize with the input RNA and translation remains off. When input RNA 1 (red) is expressed alone, it can bind to and unwind the left arm of the gate RNA and further disrupt the base of the Y stem. However, the RBS and start codon remain concealed within the right arm of the gate RNA and translation remains repressed. When input RNAs 1 and 2 are co-expressed, binding of input RNA 1 disrupts the base stem and thus weakens the overall strength of the right arm stem-loop. The newly weakened right stem-loop is now available for binding to input RNA 2, which in turn unwinds the complete right arm structure. Unwinding of the final stem-loop exposes the RBS and start codon thereby allowing translation occur.

The base 2-input OR and AND gate designs can be extended to multi-input (>2 input) gates as shown in FIGS. 12B-12G. Three-input expressions require three stem-loop structures (FIGS. 12B-12C); 4-input expressions require four stem-loop structures (FIGS. 12D-12E); 5-input expressions require five stem-loop structures (FIGS. 12F-12G); and so forth. The principal distinguishing feature of the OR gate RNAs compared to the AND gate RNAs is that the OR gate systems contain the RBS and start codons in the base stem (FIGS. 12B, 12D, 12F) such that binding of any input RNA releases the RBS and start codon. For AND gate RNAs, the RBS and start codon are concealed within the 3'-most stem-loop and are only released after all the input RNAs have bound to the gate (FIGS. 12C, 12E, 12G).

Combinations of OR and AND operations in conjunctive normal form (CNF) can also be evaluated using gate RNAs. A CNF expression can be described as an AND of ORs. An example of a CNF gate RNA for evaluating (A OR B) AND (C OR D) is shown in FIGS. 13A-13B. The gate RNA features two Y-shaped secondary structures that feed into a central stem. Each Y-shaped module corresponds to a 2-input OR expression and the 3' Y module is only accessible to the C and D input RNAs after the 5' Y module has been disrupted by binding to either input A or B. The 4-input CNF gate shown in FIGS. 13A-13B can be generalized to CNF gates of arbitrary complexity following the same approaches used for generating the multi-input OR and AND gates. An example of a 9-input CNF gate for evaluating (A OR B OR C) AND (D OR E OR F) AND (G OR H OR I) is shown in FIG. 13B. In addition, NOT logic can be accomplished with the CNF gate system by using a deactivating input RNA that is perfectly complementary to another input RNA. This deactivating RNA will bind preferentially to its corresponding input RNA and prevent it from interacting with a stem loop in the gate RNA. Implementation of such deactivating RNAs along with the CNF gate RNA concept means that loop-mediated riboregulators can be used to evaluate arbitrary Boolean logic expressions using only RNA information processing components.

Figure 14A:
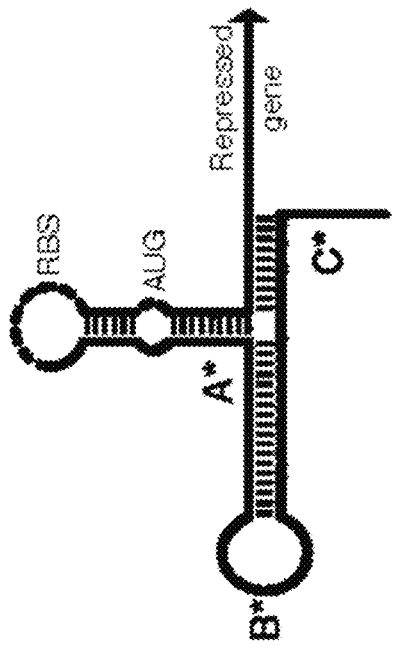
FIGS. 14A-14C show exemplary hybrid AND gate designs employing the loop-mediated mechanism. (A) 2-input hybrid AND gate design that detects input RNAs with sequences A and B. (B) 3-input hybrid AND gate design that detects input RNAs with sequences A, B, and C. (C) 4-input hybrid AND gate design that detects input RNAs with sequences A, B, C, and D.
Figure 14B:
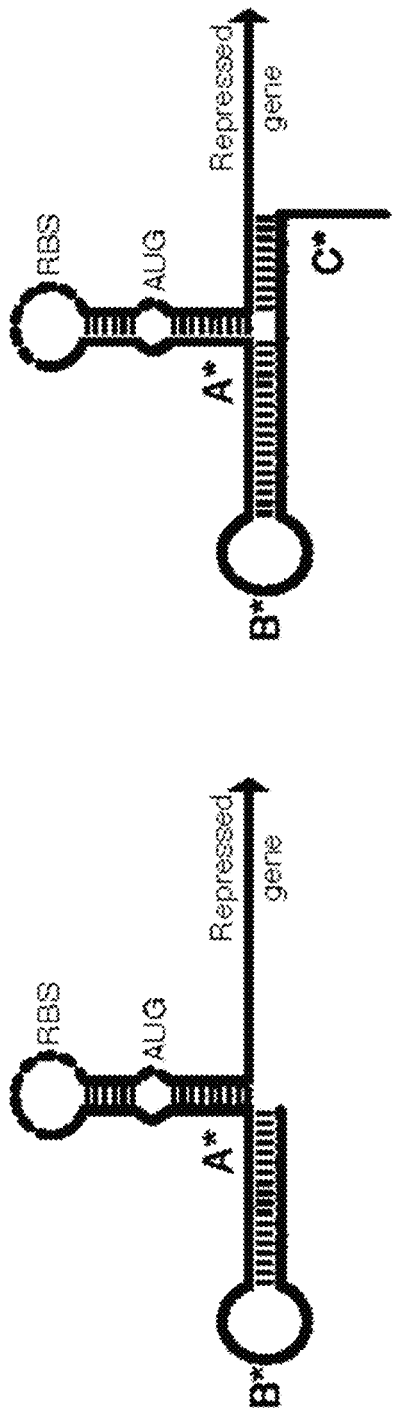
Figure 14C:
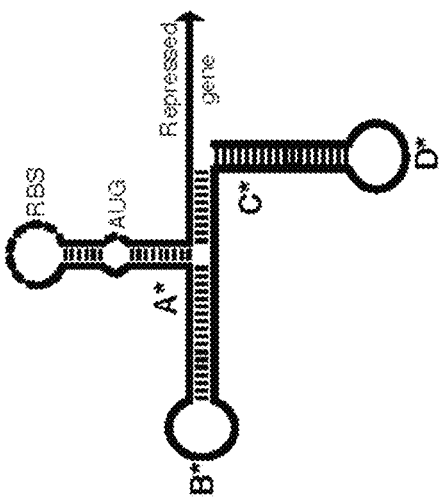

In addition, combinations of loop-mediated riboregulators and toehold switches can be incorporated in nested fashion into gate RNAs to evaluate multi-input AND logic as shown in FIGS. 14A-14C. The secondary structure of such a 2-input hybrid AND gate RNA is shown in FIG. 14A. In this gate, a toehold switch is used to regulate the output gene, however, the toehold region of the riboregulator has been incorporated into the stem of an upstream loop-mediated riboregulator. The presence of the toehold in an RNA duplex prevents its cognate input RNA from activating gene expression. The loop-mediated riboregulator, on the other hand, has an exposed loop domain and a stem of standard length. Consequently, the cognate input RNA of the beacon module can be opened through the loop-mediated interaction and disrupt the stem of the riboregulator. Once the repressing stem is removed, the toehold region of the toehold switch is fully exposed enabling its input RNA to bind and activate the gate RNA. Since both input RNAs are required for gate activation, an AND operation is evaluated. It is important to note that the sequence of the exposed toehold domain does not have any sequence correlation with the input RNA for the loop-mediated riboregulator since the toehold can be placed outside the trigger binding site of the beacon module.

This hybrid AND gate concept can be extended to arbitrary numbers of input RNA species. The secondary structure of a 3-input hybrid AND gate RNA is shown in FIG. 14B. Activation of the internal loop-mediated riboregulator module with sequence B* is inhibited by extending the stem of the riboregulator through an additional toehold switch module with sequence C*. When a cognate trigger RNA with sequence C is expressed, the toehold switch module is displaced and its inhibition of the loop-mediated riboregulator relieved. Similarly, a hybrid gate RNA with 4-input detection capability can be constructed by concealing the toehold of the toehold switch module with C* within the stem an additional loop-mediated riboregulator with sequence D* (FIG. 14C). For this 4-input hybrid AND gate, four trigger RNAs with sequences A, B, C, and D need to be present in the cell or the sample in order to activate gene expression from the AND gate RNA. In addition, the order of the riboregulator modules in the hybrid gate RNAs can be swapped (e.g., a loop-mediated riboregulator can directly regulate gene expression). Through careful selection of the order of input RNAs to be used in the gate RNA and use of bulges, arbitrary input RNAs can be used for the hybrid AND gate systems.

Compared to our previous work on RNA-only systems called ribocomputing devices (Green et al., Nature 2017, nature 23271), the loop-mediated riboregulator based logic systems and hybrid logic systems offer a number of compelling advantages. First, they have the ability to accept input RNAs for OR and AND operations with arbitrary sequences. These input RNAs can be synthetic RNAs, or endogenous or pathogenic RNAs expressed by the cells or sampled as part of an in vitro diagnostic test. Ribocomputing systems require complementarity between input RNAs involved in AND logic operations, which makes them much harder to implement for operations that require input RNAs with well-defined sequences (i.e., endogenous or pathogenic cellular RNAs, or pathogen-associated RNAs in a diagnostic).

Second, OR gates based on loop-mediated riboregulators do not require any nonsense residues to be added on to the N-terminal of the output protein. Ribocomputer OR gates and loop-mediated riboregulator AND gates add increasing numbers of nonsense residues as the number of input species increases. Third, loop-mediated riboregulator logic gates should offer improved performance for AND logic compared to ribocomputers. In ribocomputer AND logic, each input RNA is programmed to hybridize directly to the other input RNAs to form an N-molecule RNA complex for an N-input AND gate. As the number of inputs increases, an increasing fraction of incomplete reaction products are formed (e.g. 2-, 3-, . . . , and N–1-molecule RNA complexes), which leads to sharp decreases in gate performance. In contrast, for loop-mediated riboregulator AND gates, binding between the input RNAs and the gate RNA occurs in a step-by-step fashion that avoids the formation of partial products. For the expression A AND B AND C, input B can be programmed to interact with gate RNA only once input A has bound; similarly, input C only binds after the three-RNA complex A-B-gate has formed. It should be noted that input RNAs are expressed at an approximately 5- to 10-fold higher concentration than the gate RNA for the logic systems, so there is always an excess of input RNAs available to enable reactions with the gate RNA to go to completion.

Implementation of AND Gates

Figures 15A, 15B, 15C, 15D:
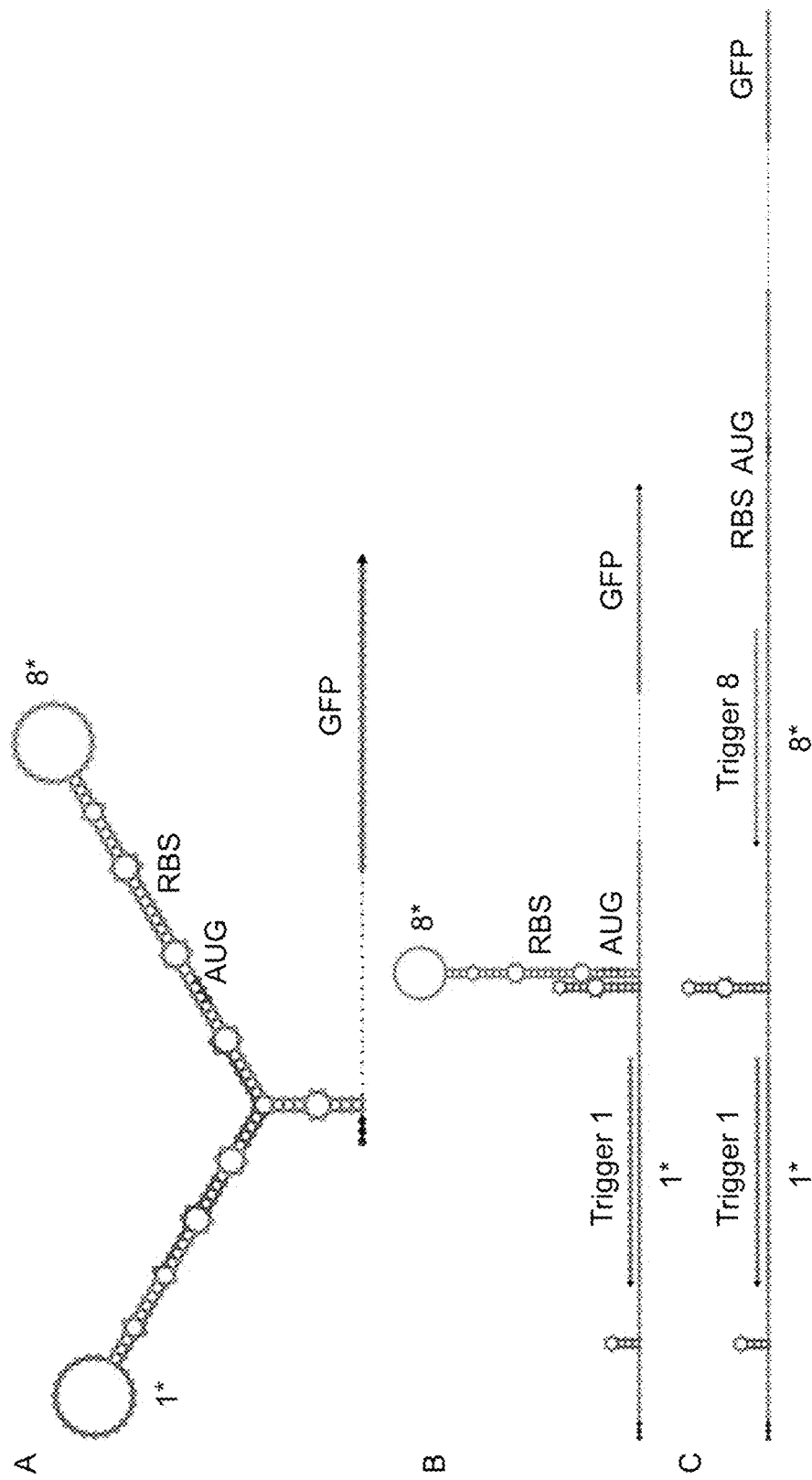
FIGS. 15A-15D illustrate exemplary in vitro 2-input 'AND' logic gate designs. (A) Detailed structure of in vitro 2-input 'AND' gate RNA design. (B) Complex of the gate RNA and trigger RNA 1. (C) Complex of gate RNA with trigger 1 RNA and trigger 8 RNA. (D) ON/OFF ratio of the in vitro 2-input 'AND' logic gate design for different combinations of input trigger RNAs. The gate RNA was used to regulate GFP expression in the cell-free reaction. The OFF-state fluorescence was obtained from a cell-free reaction where only the gate RNA was expressed.

We have successfully implemented AND gate RNA logic devices based on loop-mediated riboregulators using in vitro cell-free reactions and in living *E. coli* cells. The design of an exemplary 2-input AND logic circuit tested in vitro is shown in FIG. 15. The AND gate RNA is designed to activate translation only when two cognate inputs, named trigger 1 and trigger 8, are both present. When the gate RNA is expressed with trigger RNA 1, the trigger is able to bind through a loop-mediated interaction to the left branch of the gate RNA. Binding of trigger 1 disrupts the lower stem of the gate RNA and a further intermolecular refolding reaction reduces the length of the right branch of the gate RNA (FIG. 15B). The newly weakened stem-loop containing the binding site for trigger RNA 8 can now interact with this input RNA to reveal the ribosomal binding site (RBS) and start codon and enable production of the output gene (FIG. 15C). In the absence of trigger RNA 1, trigger RNA 8 is unable to expose the RBS and start codon for translation since the right branch of the gate RNA upper stem is too strong to be unwound. As a result, both trigger RNA 1 and 8 must be present for protein translation to occur and the gate RNA evaluates 2-input AND logic.

The 2-input AND gate RNA regulating GFP was tested in cell-free reactions in the presence of different combinations of the input RNAs (FIG. 15D). GFP fluorescence was measured for each input combination and divided by the fluorescence obtained for a reaction with the gate RNA expressed alone. These measurements confirm strong GFP activation only in the presence of both inputs and low GFP levels with one of the two inputs present. Thus, successful 2-input AND behavior was observed.

| | RNA Sequence |
|---|---|
| AndH2 Gate RNA | GGGACUCAAAUCUUCGCUACAGCGACAUCUACAGUUUCCGUAUUCUGU GAAGCCCUAGGGUCCGAUACAGAAACGGUAGAACUCGCUAAAGCGAUG UCUACCUGCCAUAUCUUAUCUCCUGAGUUUCAUCUUAAAGUCCUUGUA ACAGUCGUCAAGACGAAACAGAGGAGAUACAAUAUGGCAAUUAGACAA GAUACGAGUAACCUGGCGGCAGCGCAAAAGAUGCGUAAAGGAGAAGAA CUUUUCACUGG (SEQ ID NO: 72) |

| | RNA Sequence |
|---|---|
| Trigger T1 (BR_6clamp_act_ N001_trig) | GGGCCAGUGACUUGUCACUGGGAACGGACCCUAGGGCUUCACAGAAUA CGGAAACGAC (SEQ ID NO: 73) |
| Trigger T8 (BR_6clamp_act_ N005_trig) | GGGCUCACCUGCCAAGGUGAGAGCGACGACUGUUACAAGGACUUUAAG AUGAAACGAC (SEQ ID NO: 74) |

Figures 16A, 16B, 16C:
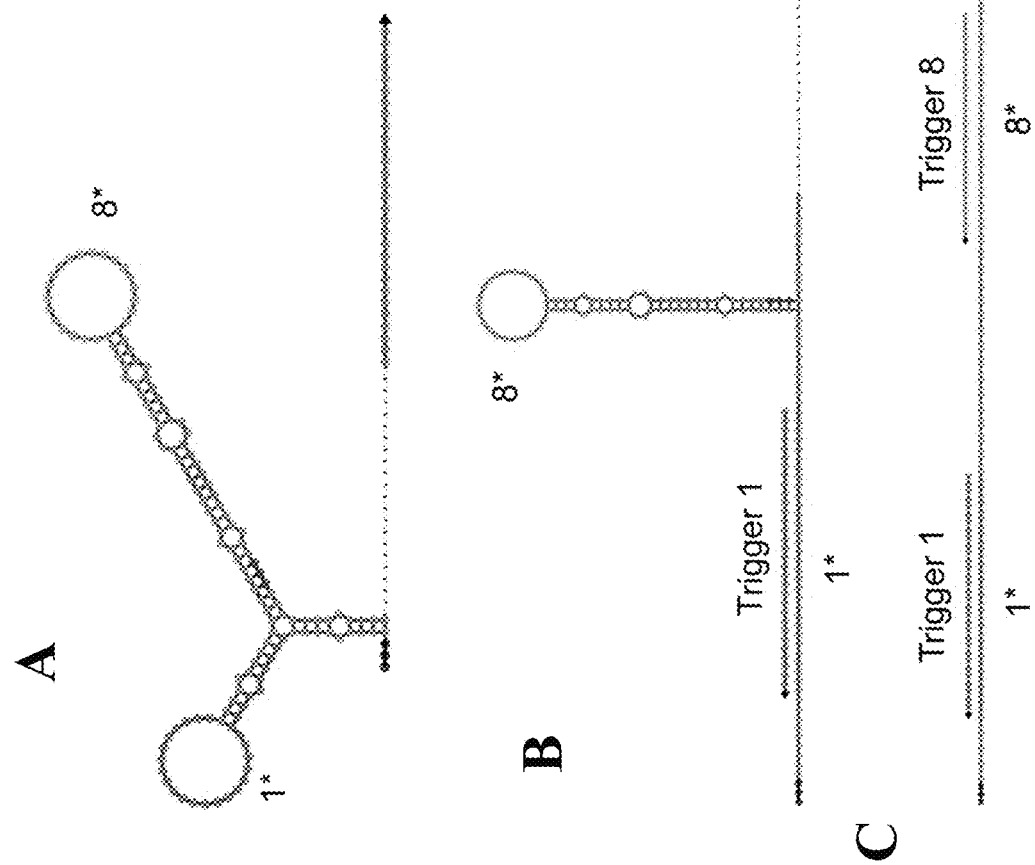

An exemplary 2-input AND logic circuit for use in vivo is shown in FIG. 16. This system has a design similar to that of the in vitro system, but with fewer bulge domains and a longer lower stem in the gate RNA (FIGS. 16A-16C). These modifications to the gate RNA increase the strength of its secondary structure and promote lower leakage for the logical FALSE states. The 2-input AND gate circuit was tested in E. coli using GFP as the output protein. The gate RNA was challenged with different combinations of cognate and non-cognate trigger RNAs. The OFF-state fluorescence was measured from the case in which the gate RNA was co-expressed with two non-cognate triggers. As with the in vitro circuit, we observed strong GFP expression only when both the input trigger RNAs 1 and 8 were expressed by the cells, as expected for 2-input AND logic (FIG. 16D). Activation of the gate yielded at least 10-fold increases in GFP expression within three hours of induction of transcription of the circuit RNAs.

| | RNA Sequence |
|---|---|
| AndH2_Lbul_Gate RNA | GGGCAUUCUAUCUACAUCUAUUUCAACUGAUUUCAGUAAUACACCGU UUCCGUAUUCUGUGAAGCCCUAGGGUCCGAUACAGAAACGGUGUAUU ACUGAAAUCAGUCUUACACCUGCCAUAUGAUAUCUCCUCUGUUUCAU CUUAAAGUCCUUGUAACAGUCGUCAAGACGAAACAGAGGAGAUAAGA UAUGGCAAAUGUAAGUGAAAUAGAUAGAGAUAGAAUGAACCUGGCGG CAGCGCAAAAG (SEQ ID NO: 75) |
| Trigger T1 (BR_6clamp_act_ N001_trig) | GGGCCAGUGACUUGUCACUGGGAACGGACCCUAGGGCUUCACAGAAU ACGGAAACGAC (SEQ ID NO: 76) |
| Trigger T8 (BR_6clamp_act_ N005_trig) | GGGCUCACCUGCCAAGGUGAGAGCGACGACUGUUACAAGGACUUUAA GAUGAAACGAC (SEQ ID NO: 77) |

Implementation of In Vitro OR Gates

Figures 17A, 17B, 17C, 17D:
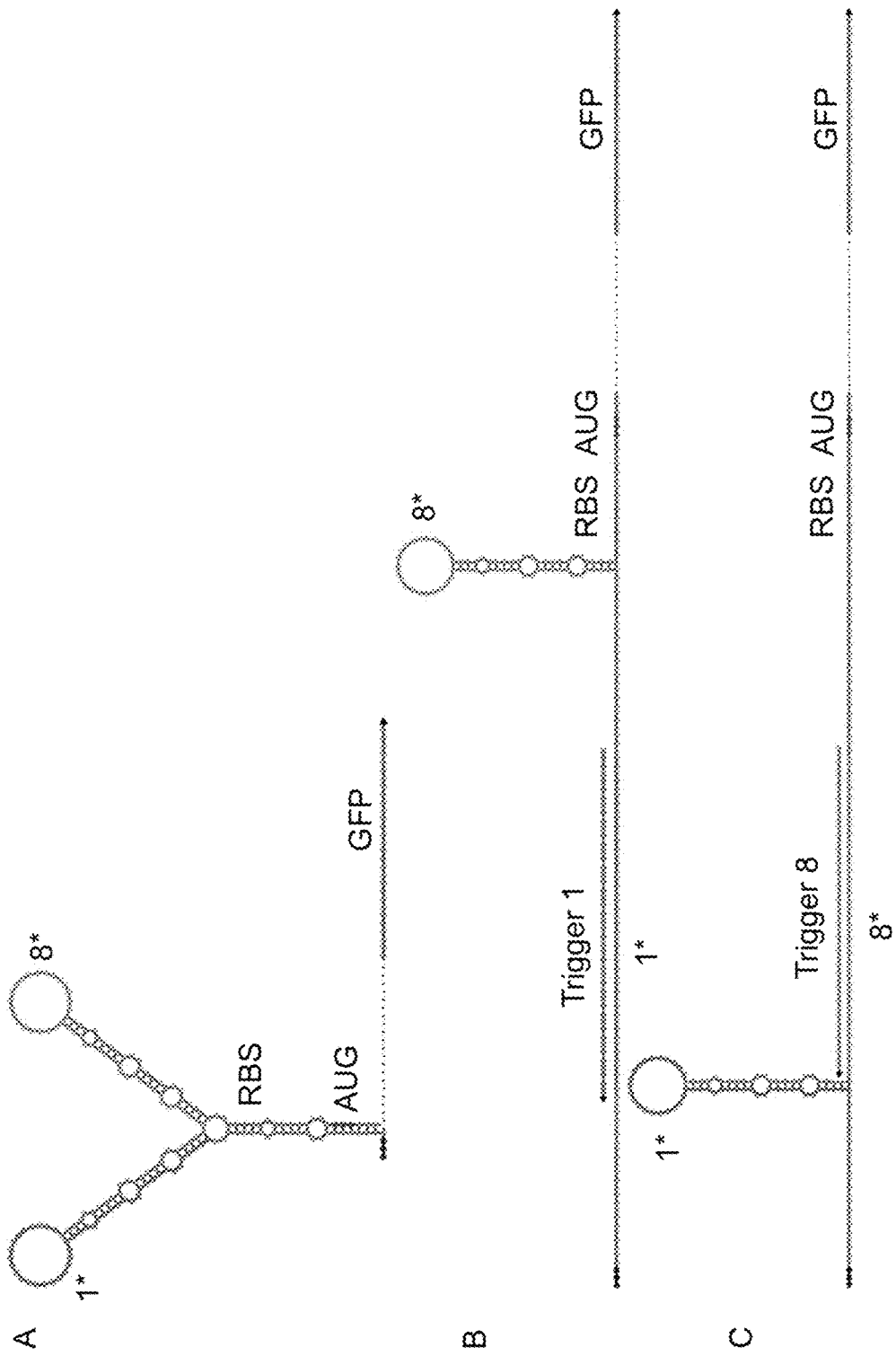
FIGS. 17A-17D illustrate exemplary in vitro 2-input 'OR' logic gate designs. (A) Detailed structures of the in vitro 2-input 'OR' gate RNA design. (B) Complex of the gate RNA and trigger 1 RNA. (C) Complex of the gate RNA and trigger 8 RNA. (D) ON/OFF ratio of the first in vitro 2-input 'OR' logic gate design in cell-free reactions. The gate RNA was used to regulate GFP expression. The OFF-state fluorescence was taken from a reaction in which only the gate RNA was expressed.

FIGS. 17A-17C shows the design schematic for an exemplary 2-input OR gate RNA implemented in vitro. The gate RNA features a Y-shaped secondary structure similar to that of the AND gate RNAs, except that the RBS and start codon are positioned within the lower stem of the gate RNA. When either of the input RNAs, named trigger 1 and trigger 8, are present, they are able to bind to the loop of the left or right branches of the gate RNA and disrupt much of its secondary structure. Importantly, trigger binding causes the lower stem of the gate RNA to unwind and thereby exposes the RBS and start codon so that translation of the output gene can occur. Since either trigger can activate translation, the gate carries out the equivalent of 2-input OR logic.

The 2-input OR gate RNA was tested in cell-free reactions with and without cognate trigger RNAs using GFP as the output protein. In the absence of cognate RNAs, low GFP expression was observed. Strong increases in GFP fluorescence, over 15-fold and 12-fold for trigger 1 and trigger 8, respectively, were observed as expected (FIG. 17D).

| | RNA Sequence |
|---|---|
| Or1 Gate RNA | GGGAUUCAUUUCACAUCUGCUCUAUAUCGUCCGCAAUCCUGUUUCCGUA UUCUGUGAAGCCCUAGGGUCCGAUACAGAAACUUGAUUGACGACGACC UACGCUCAUUUCGUUUCAUCUUAAAGUCCUUGUAACAGUCGUCAAGAC GAAACGAAAUGAAAGUAGGAAUAGAGGAGAUGACAAAUGAAUAACCUG GCGGCAGCGCAAAAGAUGCGUAAAGGAGAAGAACUUUUCACUGG (SEQ ID NO: 78) |

-continued

| | RNA Sequence |
|---|---|
| Trigger T1 | GGGCCAGUGACUUGUCACUGGGAACGGACCCUAGGGCUUCACAGAAUAC GGAAACAGGAUUGCGGACGAGAC (SEQ ID NO: 79) |
| Trigger T8 | GGGCCAGUGACUUGUCACUGGAGCGACGACUGUUACAAGGACUUUAAG AUGAAACGAAAUGAGCGUAGGGAC (SEQ ID NO: 80) |

Digital-to-Analog RNA Devices

The RNA-based logic devices described above carry out the equivalent of digital logic in that they can adopt one of two possible binary states: ON or OFF, low or high, or 0 or 1. Typical biological systems are fundamentally analog in nature, with signals that can take on a range of values or concentrations. Systems that convert between digital and analog signals are thus essential devices for future synthetic biological circuits. One such system is a digital-to-analog converter that takes multiple binary input signals, in this case the presence or absence of an input RNA, and converts it into an analog signal, in this case protein expression level. These RNA-based digital-to-analog (DTA) systems, thus, output different protein levels depending on the precise combination of input RNAs present.

Figures 18A, 18B, 18C, 18D:
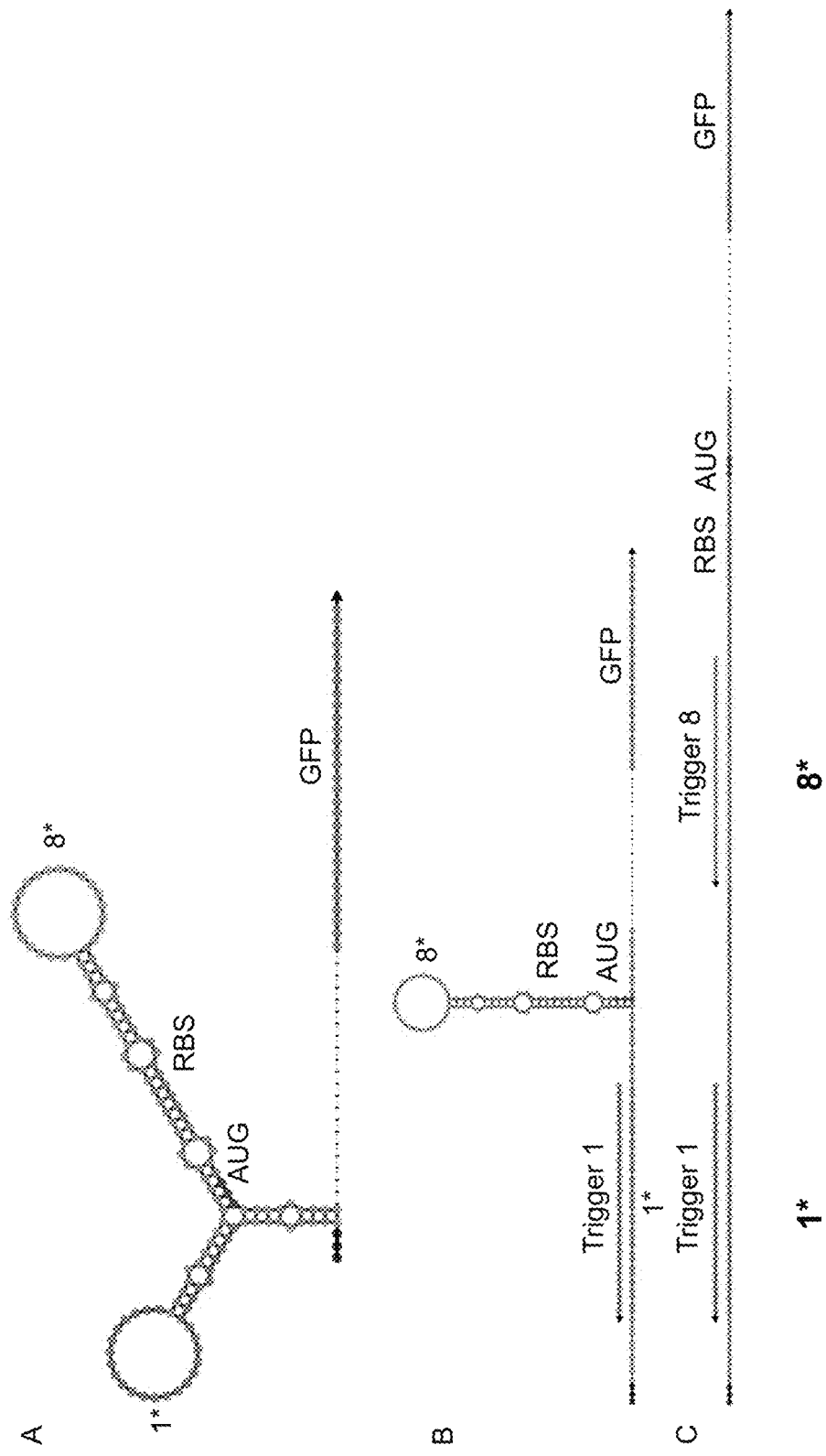
FIGS. 18A-18D illustrate exemplary in vitro 2-input 'Digital-to-analog' ('DTA') designs. (A) Detailed structures of in vitro 2-input 'DTA' gate RNA design. (B) Complex of the gate RNA and trigger 1 RNA. (C) Complex of the gate RNA with trigger 1 RNA and trigger 8 RNA. (D) ON/OFF ratio of the first in vitro 2-input 'DTA' design regulating GFP expression in a cell-free reaction. The OFF-state fluorescence was measured from a reaction in which only the gate RNA was expressed.

The schematic of an exemplary DTA device implemented in vitro is shown in FIGS. 18A-18C. The DTA gate RNAs adopt a secondary structure very similar to that of the AND gate RNAs with a Y-shaped geometry and the RBS and start codon sequestered within the right branch of the gate. The main design differences in the DTA gate RNA are that the two branches of the gate RNA are shortened and the RBS and start codon are shifted closer to the lower stem of the gate. These modifications lead to increased translation when the gate RNA interacts with the cognate trigger for the right branch (Trigger RNA 8), since the weakened right branch is easier to disrupt. Furthermore, it leads to low-level translation when the cognate trigger for the left branch (Trigger RNA 1) interacts with the gate RNA, since the RBS and start codon can be transiently exposed at the bottom of the stem (FIG. 18B). The highest translation levels are obtained when both input RNAs (Trigger RNA 1 and 8) are present, which leads to complete exposure of the RBS and start codon (FIG. 18C). The DTA gate RNA regulating GFP was tested in in vitro cell-free reactions using combinations of the two input RNAs. In the absence of any cognate inputs, GFP expression was low but increased by 2- to 3-fold in response to trigger RNA 1. Upon interaction with trigger RNA 8 alone, gate RNA GFP expression increased by roughly 8-fold compared to the non-cognate input case. Finally, the highest GFP expression level was obtained with both input RNAs present. Thus, four distinct output protein levels were obtained using the four different combinations of the RNAs, enabling conversion of the digital input RNA signal to an analog protein output signal. Experiments for DTA systems that operate in vivo and with higher numbers of input RNAs are underway.

| | RNA Sequence |
|---|---|
| And1 Gate RNA | GGGCUUGCUUAUGUUUCCGUAUUCUGUGAAGCCCUAGGGUCCGAUACCGAA ACCAUAUCUUAUCUCCUGAGUUUCAUCUUAAAGUCCUUGUAACAGUCGUCA AGACGAAACAGAGGAGGAUAACAUAUGAUAAGCAAGAACCUGGCGGCAGCGC AA (SEQ ID NO: 81) |
| Trigger T1 (BR_6clamp_act_ N001_trig) | GGGCCAGUGACUUGUCACUGGGAACGGACCCUAGGGCUUCACAGAAUACGG AAACGAC (SEQ ID NO: 82) |
| Trigger T8 (BR_6clamp_act_ N005_trig) | GGGCUCACCUGCCAAGGUGAGAGCGACGACUGUUACAAGGACUUUAAGAUG AAACGAC (SEQ ID NO: 83) |

Pathogen Detection

Figure 19:
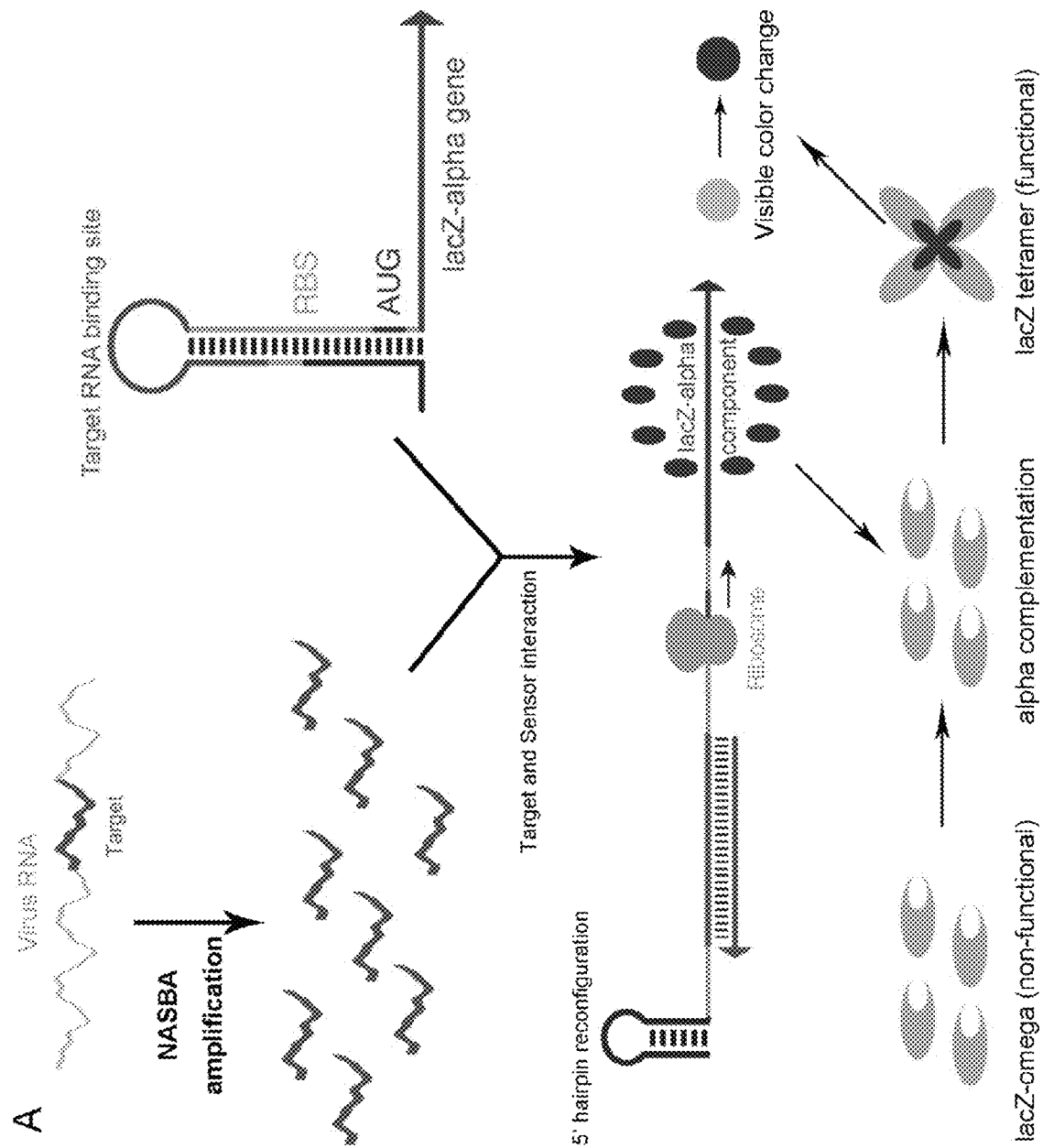
FIG. 19 is a schematic illustrating an exemplary pathogen detection method in which the virus or target nucleic acid is amplified using NASBA or another isothermal amplification technique and then detected using a loop-mediated riboregulator that initiates a colorimetric reaction. In this schematic, the output protein is the alpha subunit of the lacZ enzyme. The low molecular weight alpha subunit is complemented by the high molecular weight omega subunit of lacZ. Upon complementation, the functional lacZ tetramer forms and the colorimetric reaction can proceed to produce a visible color change. A 5' hairpin, shown in blue, forms in the loop-mediated riboregulator upon binding of target RNA. Use of alpha complementation for lacZ enables faster readout from the diagnostic by allowing the cell-free system to synthesize a much smaller protein (lacZ alpha subunit) than the full lacZ enzyme.

The design of the loop-mediated riboregulators enables them to detect target RNAs with arbitrary sequences. We have validated several loop-mediated riboregulators that can detect nucleic acids from multiple viruses and the malaria parasite *Plasmodium falciparum*. FIG. 19 depicts the process used for detecting low concentrations of viral or pathogen nucleic acids from a biological sample through to a paper-based or liquid-phase cell-free reaction that produce an optical reporter (either visible or fluorescent). Nucleic acids from the sample are first amplified using a reaction such as NASBA, RPA, HDA, LAMP, or even PCR to generate many copies of the pathogen-associated nucleic acid. These amplified products are then tested for their sequence using a loop-mediated riboregulator in a cell-free system.

We appended a stem refolding domain on the 5' end of the loop-mediated riboregulator switch RNAs to increase their sensitivity against natural RNAs with the potential for high secondary structure. The refolding region is shown as the blue domain in FIG. 19 and it forms as the target RNA binds and begins to disrupt the stem of the switch RNA. This refolding domain provides an additional free energy gain to supplement the branch migration interaction between switch and trigger and encourages activation of the riboregulator.

In order to speed up detection, the alpha subunit of lacZ can be regulated using the loop-mediated riboregulators while the omega subunit of lacZ can be freeze-dried directly onto the paper (FIG. 19). The alpha subunit is substantially smaller than the complete lacZ enzyme and is thus much faster to translate and fold using the cell-free reactions. The alpha subunit can then complement the omega subunit already present in the reaction to form a functional lacZ tetramer.

Figure 20:
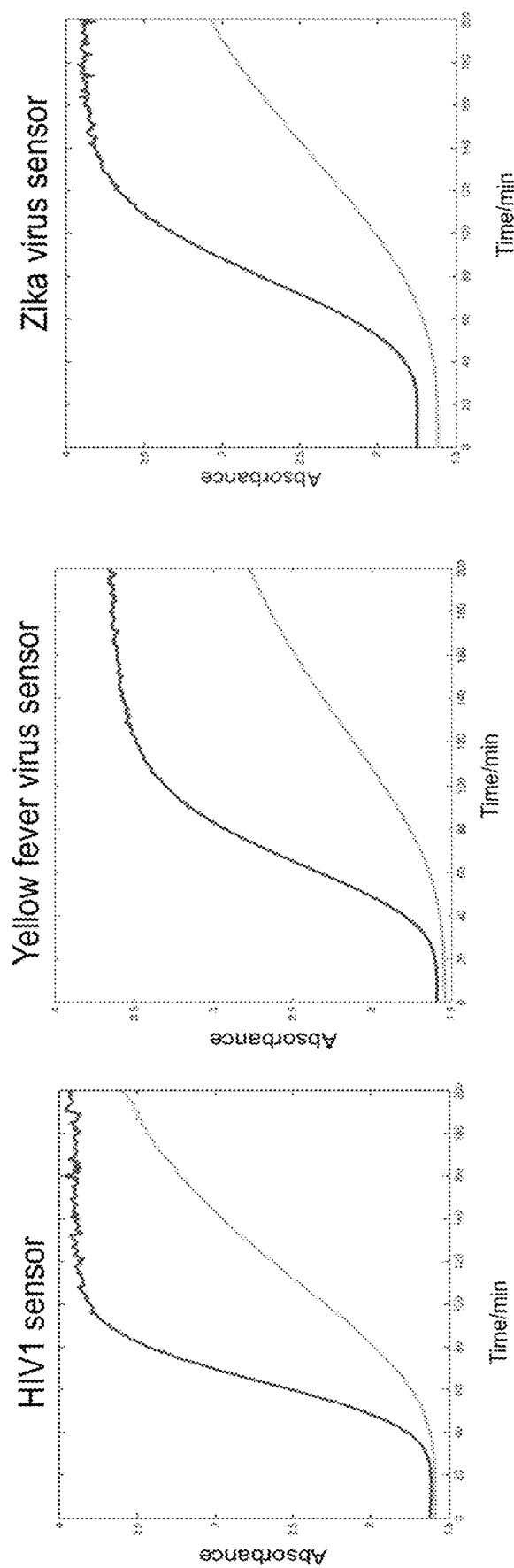
FIG. 20 demonstrates sensor response curves for loop-mediated riboregulators designed to detect a variety of different nucleic acids associated with viruses and parasites. Red: Absorbance at 570 nm obtained from the colorimetric paper-based cell-free reaction with target nucleic acid and the corresponding sensor present; Green: Absorbance at 570 nm obtained from the colorimetric paper-based cell-free reaction with the corresponding sensor expressed alone. Despite some leakage in absence of the trigger RNA (green curves), all sensors provide clear changes in absorbance in the presence of the target RNA within 40 to 100 minutes. Mitochondrial DNA and the Pfs25 gene from *Plasmodium falciparum*: were used as biomarkers for malaria.
Figure 20:
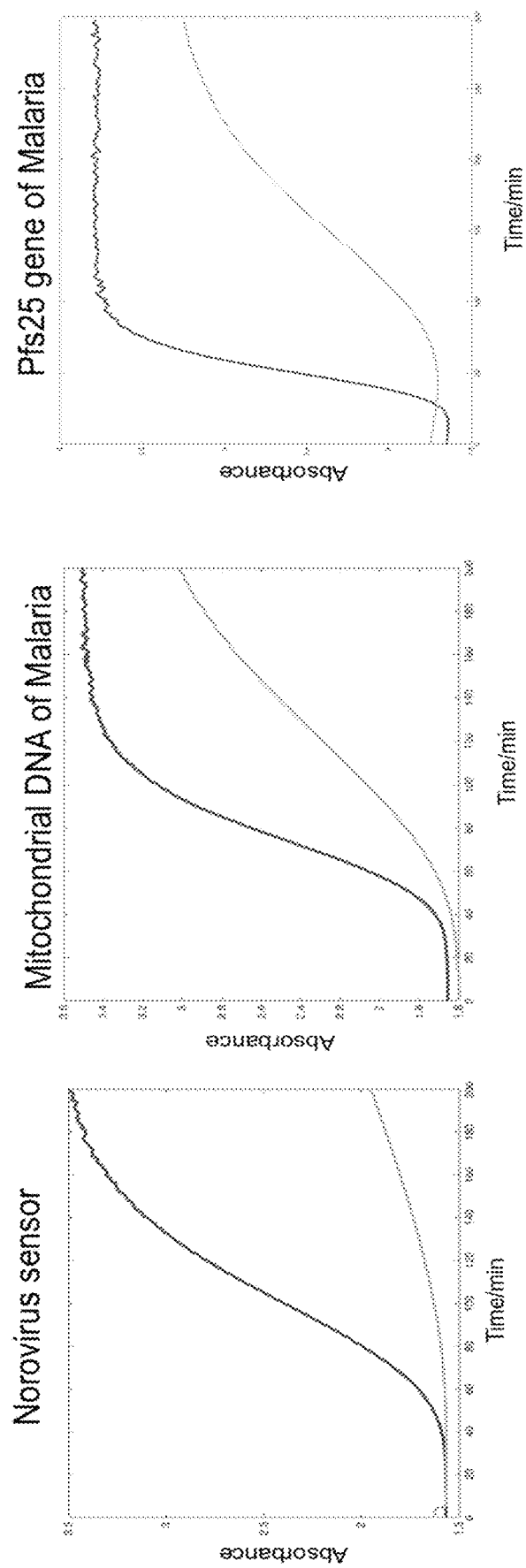

FIG. 20 provides data from a set of six different loop-mediated riboregulators employing a 5' reconfiguration hairpin and designed to sense natural nucleic acids from viruses and parasites. The four viruses detected were HIV1, yellow fever, Zika, and norovirus. The malaria parasite *Plasmodium falciparum*: was detected via mitochondrial DNA sequences and through the Pfs25 mRNA. Pfs25 is only expressed in the gametocyte stage of the life cycle of *P. falciparum*, where the parasite is capable of being transmitted from humans to mosquitoes. Pfs25 sensors thus are very useful tools for detecting patients who can transmit the infection and must be identified for successful malaria eradication efforts. The riboregulators were detected in paper-based cell-free reactions and used to regulate expression of the alpha subunit of lacZ. The optical absorbance at a wavelength 570 nm was measured through the paper over the course of the cell-free reactions as the colorimetric substrate was cleaved. Dark green curves in FIG. 20 generated from the riboregulators challenged with their cognate trigger RNAs all show strong increases in absorbance, corresponding to the production of a visible purple color, within 40 to 100 minutes. Light red curves in FIG. 20 generated from the riboregulators expressed on their own do show production of the purple cleavage product, but the onset of the color change is substantially later and weaker than that observed with the cognate triggers. This leakage is thus sufficiently low to permit accurate identification of the virus- or parasite-associated nucleic acids in low-cost point-of-care diagnostic test using the loop-mediated riboregulators.

| Target Pathogen | Sensor Name | Sensor Sequence | Target Name | Target Sequence |
|---|---|---|---|---|
| HIV | BRR_H16_L27_reconfigD9_noextra_HIV_4_star_c | GGGUAACGGAUGAUG UACAAUCCAUUAUCU CCUAAGUCCUCCUAC UCCCUGACAUGCUGU CAUCAUUUCUUCGUA GGAGGACAGAGGAGA UAACGGAUGAUACAU AACCUGGCGGCAGCG CAA (SEQ ID NO: 84) | HIV_4_star | GGGAGCAUUGGGACCAGC GGCUACACUAGAAGAAAU GAUGACAGCAUGUCAGGG AGUAGGAGGACCCGGCCA UAAGGCAAGAGUUUUGGC UGAAGCAAUGAGCCAAGU AACAAAUUCAGCUACCAU AAUGAUGCAGAGAGGCAA U (SEQ ID NO: 85) |
| Yellow fever virus | BRR_H16_L27_reconfigD9_noextra_YFV_antisens_B | GGGUAACGGAUGAUG UACAAUCCAUUAUCU CCUAAAAAAUAAAAC AAAAAACAAAACAAA UUGGAAACAGACGUU UUAUUUUAGAGGAGA UAACGGAUGAUACAU AACCUGGCGGCAGCG CAA (SEQ ID NO: 86) | YFV_antisens_B_amplicon | GAACAUGUCUGGUCGUAA AGCUCAGGGAAAAACCCU GGGCGUCAAUAUGGUACG ACGAGGAGUUCGCUCCUU GUCAAACAAAAUAAAACA AAAAACAAAACAAAUUGG AAACAGACC (SEQ ID NO: 87) |
| Zika virus | BRR_H16_L27_reconfigD9_noextra_ZIKV_targ27B_sens_F | GGGUAACGGAUGAUG UACAAUCCAUUAUCU CCUAAGGUGGCUUCG GCUCUUGGUGAAUUG GGCGUUAUCUCACGA AGCCACCAGAGGAGA UAACGGAUGAUACAU AACCUGGCGGCAGCG CAA (SEQ ID NO: 88) | ZIKV_targ27B_sens | AUGACACAGGACAUGAAA CUGAUGAGAAUAGAGCGA AAGUUGAGAUAACGCCCA AUUCACCAAGAGCCGAAGC CACCCUGGGGGGGUUUGG AAGCCUAGGAC (SEQ ID NO: 89) |
| Norovirus | BRR_H16_L27_reconfigD9_noextra_norovirus_GII_rev_D | GGGUAACGGAUGAUG UACAAUCCAUUAUCU CCUAAGCACGUGGGA GGGCGAUCGCAAUCU GGCUCCCAGUUUUCC CACGUGCAGAGGAGA UAACGGAUGAUACAU AACCUGGCGGCAGCG CAA (SEQ ID NO: 90) | norovirus_GII_rev_D_amplicon | GCACGUGGGAGGGCGAUC GCAAUCUGGCUCCCAGUUU UGUGAAUGAAGAUGGCGU CGAAUGACGCCAACCCAUC UGAUGGGUCCGCAGCCAAC CUCG (SEQ ID NO: 91) |
| Malaria (*P. falciparum* mitochondrial DNA) | BRR_H16_L27_reconfigD9_noextra_PfMt869_FL_B | GGGUAACGGAUGAUG UACAAUCCAUUAUCU CCUAAGAGCGGUGUG UACAAGGCAACAAUA CACGCUAGAUAUCAC ACCGCUCAGAGGAGA UAACGGAUGAUACAU AACCUGGCGGCAGCG CAA (SEQ ID NO: 92) | PfMt869_FL | AGCCUUGCAAUAAAUAAUA TCTAGCGTGTATTGTTGCCT TGTACACACCGCTC (SEQ ID NO: 93) |

| Target Pathogen | Sensor Name | Sensor Sequence | Target Name | Target Sequence |
|---|---|---|---|---|
| Malaria (*P. falciparum* gametocyte mRNA Pfs25) | BRR_H16_ L27_ rcfgD09_ NX_ Pfs25rev_A | GGGUAACGGAUGAUG UACAAUCCAUUAUCU CCUAAGCUUGUAAAU GUAAUCUUGGAUAUG AUAUGGUAAAUAAUU UACAAGCAGAGGAGA UAACGGAUGAUACAU AACCUGGCGGCAGCG CAAAAGAUG (SEQ ID NO: 94) | Pfs25_ amplicon | GACUGUAAAUAAACCAUG UGGAGAUUUUUCCAAAUG UAUUAAAAUAGAUGGAAA UCCCGUUUCAUACGCUUGU AAAUGUAAUCUUGGAUAU GAUAUGGUAAAUAAUGUU UGUAUACCAAAUGAAUGU AAGAAUGUAACUUGUGGU AACGGUAAAUGAUAUG (SEQ ID NO: 95) |

Summary

In summary, this Example describes and demonstrates a novel class of riboregulators called loop-mediated riboregulators that can activate or repress gene expression in response to trigger RNAs bearing completely arbitrary sequences. Loop-mediated riboregulators provide a high degree of orthogonality, with a library of 15 devices showing cross talk levels below 4%, and routinely increase gene expression by 100-fold or more. Loop-mediated repressor systems also provide wide dynamic range of up to 90-fold. Testing of the loop-mediated riboregulators in *E. coli* revealed that they provide ultralow signal leakage in the absence of the trigger RNA. For the best devices, OFF state fluorescence reporter expression levels are indistinguishable from cell autofluorescence. Further evaluation of the devices through qRT-PCR revealed that this ultralow leakage is due to a new riboregulator mechanism that combines regulation at both the transcriptional and post-transcriptional level when expressed via T7 RNA polymerase. Computer-based design and optimization of loop-mediated riboregulator device parameters afforded sensors capable of resolving single base mutations in trigger RNAs and improvements in performance are likely through continued refinement and the use of competitive RNA binding sites upstream of the switch RNA hairpin. We have conceived a number of elegant approaches to incorporate loop-mediated riboregulator modules into extended gate RNAs that enable computation of OR, AND, CNF, and NOT logic operations using arbitrary RNA sequences as input molecules. These capabilities mean that loop-mediated riboregulators, in principle, will be able to evaluate arbitrary Boolean logic expressions.

The loop-mediated riboregulators provide a generalizable set of new molecular tools for programming biological systems in vivo, in vitro, and on paper. For the purposes of in vivo synthetic biology, we envision that they can be used for the construction of complex genetic circuits for evaluating arbitrary logic expressions. Furthermore, their ability to detect and respond to arbitrary RNAs means that they can be used to monitor endogenous RNA molecules expressed by the cell or those expressed upon infection by a pathogen. Detection of endogenous RNAs can be used as a means of fine-tuning gene expression for metabolic engineering; for high-throughput screening of new antibiotics, as numerous characteristic small RNAs are expressed when bacteria are subjected to stress; or for generating whole-cell biosensors. Detection of pathogenic RNAs can be used to shut down cell growth upon infection by bacteriophage and protect companies from the high costs of decontaminating their equipment following phage contamination. SNP sensing loop-mediated riboregulators can also be used to monitor the emergence of resistance conferring mutations in real-time.

For in vitro and on paper diagnostic applications, loop-mediated riboregulator based logic systems could be deployed to reduce the likelihood of false positives or false negatives. For instance, AND logic would be used to make sure that at least two RNAs associated with a pathogen are present in a sample before returning a positive test result. Similarly, OR logic could be used to provide a positive result if one or more of a set of pathogen-associated nucleic acids is detected in a sample. The ability of the loop-mediated riboregulators to detect SNPs is also very promising for future applications. There are currently many SNPs that are strongly associated with antibiotic resistance[29-31], antimicrobial resistance in illnesses such as malaria[32,33] and tuberculosis[34], and cancer[35]. SNP-sensitive detectors could be used to monitor the spread and evolution of different MRSA strains[30], rapidly test for antibiotic susceptibility[36], slow the spread of artemisinin resistant[32] strains of malaria, or provide a readout in liquid biopsies for cancer[37]. Importantly, all these applications could be implemented in a very low-cost, point-of-care format to enable advanced molecular diagnostics to be deployed anywhere in the world.

We claim:

1. A loop-mediated riboregulator comprising a synthetic nucleic acid molecule, the synthetic nucleic acid molecule comprising:
   (a) a stem-loop structure, the stem-loop structure comprising:
      a first stem-forming domain;
      a loop-forming domain after the final 3' nucleotide of the first stem-forming domain; and
      a second stem-forming domain after the final 3' nucleotide of the loop domain;
   the second stem-forming domain comprising a ribosomal binding site (RBS), a translational start codon, and a 6 nucleotide clamp;
      wherein the loop domain and a portion of the first stem-forming domain form a trigger RNA docking site that is complementary to a trigger RNA; and
   (b) a coding sequence located downstream of the start codon,
   wherein the second stem-forming domain is substantially complementary to the first stem-forming domain,
   wherein the coding sequence consists of a gene,
   wherein the 6 nucleotide clamp in the second stem-forming domain corresponds to the first 6 nucleotides of the coding sequence, and
   wherein the coding sequence does not comprise a linker.

2. The riboregulator of claim 1, wherein the coding sequence encodes a reporter protein.

3. The riboregulator of claim 1, wherein the trigger RNA docking site has a length of 21 nucleotides.

4. The riboregulator of claim 1, wherein the stem-forming domains each have a length of 33 nucleotides.

5. The riboregulator of claim 1, wherein the trigger RNA docking site is fully or partially complementary to a target RNA molecule.

6. The riboregulator of claim 5, wherein the target RNA molecule is selected from the group consisting of a messenger RNA (mRNA) molecule, microRNA, small interfering RNA (siRNA), antisense RNA, non-coding RNA, and mRNA splice variant.

7. The riboregulator of claim 1, wherein the trigger RNA docking site is 14-20 nucleotides long.

8. The riboregulator of claim 1, wherein the first and second stem-forming domains comprise 5 non-complementary sites.

9. The riboregulator of claim 8, wherein the 5 non-complementarity sites are at 6, 12, 13, 22, and 23 nucleotides from the bottom base pair of the stem-loop structure.

10. The riboregulator of claim 1, wherein at least one set of additional hairpin forming sequences is present 5' of the first stem-forming domain, wherein the at least one additional set of hairpin forming sequences comprises a first hairpin-forming domain, a sequence that is identical to the sequence of the trigger RNA docking site except for one nucleotide, and a second hairpin-forming domain, wherein the first hairpin-forming domain and the second hairpin-forming domain are substantially complementary.

11. The riboregulator of claim 10, wherein the nucleotide that differs between the trigger RNA docking site and the sequence that is identical to the sequence of the trigger RNA docking site except for one nucleotide is the nucleotide positioned 5 nucleotides from the 3' end of the first stem-forming domain.

* * * * *

SEQUENCE LISTING

<160> NUMBER OF SEQ ID NOS: 95

<210> SEQ ID NO 1
<211> LENGTH: 114
<212> TYPE: RNA
<213> ORGANISM: Artificial Sequence
<220> FEATURE:
<223> OTHER INFORMATION: synthetic

<400> SEQUENCE: 1
gggucuaucu auuucacauc uccuaaguuu ccguauucug ugaagcccua ggguccgaua    60
cagaaacaga ggagaugaca aaugaauaga aaccuggcgg cagcgcaaaa gaug        114

<210> SEQ ID NO 2
<211> LENGTH: 114
<212> TYPE: RNA
<213> ORGANISM: Artificial Sequence
<220> FEATURE:
<223> OTHER INFORMATION: synthetic

<400> SEQUENCE: 2
ggguccauuc auauacuauc uccuaaguuc ucguuccaau ucgcucucgu ccuguccgaa    60
caagaacaga ggagauaaga uaugaaugga aaccuggcgg cagcgcaaaa gaug        114

<210> SEQ ID NO 3
<211> LENGTH: 114
<212> TYPE: RNA
<213> ORGANISM: Artificial Sequence
<220> FEATURE:
<223> OTHER INFORMATION: synthetic

<400> SEQUENCE: 3
gggcuuauca auaucacauc uccuacgucu uuagucgcuu cgggacagug ugcauccgac    60
uaaagacaga ggagaugaca uaugaauaag aaccuggcgg cagcgcaaaa gaug        114

<210> SEQ ID NO 4
<211> LENGTH: 114
<212> TYPE: RNA
<213> ORGANISM: Artificial Sequence
<220> FEATURE:
<223> OTHER INFORMATION: synthetic

<400> SEQUENCE: 4
gggcguugaa aucugcuauc uccuacguau uaguuuaugc uaccguaagc cugucucaaa    60
cgaauacaga ggagauacaa gaugacaacg aaccuggcgg cagcgcaaaa gaug        114

<210> SEQ ID NO 5
<211> LENGTH: 114
<212> TYPE: RNA
<213> ORGANISM: Artificial Sequence
<220> FEATURE:
<223> OTHER INFORMATION: synthetic

<400> SEQUENCE: 5
ggguagugcc auaucuuauc uccugaguuu caucuuaaag uccuuguaac agucgucaag    60
acgaaacaga ggagauaaca uaugacacua aaccuggcgg cagcgcaaaa gaug        114

<210> SEQ ID NO 6
<211> LENGTH: 114
<212> TYPE: RNA
<213> ORGANISM: Artificial Sequence
<220> FEATURE:
<223> OTHER INFORMATION: synthetic

<400> SEQUENCE: 6
gggaugucca auuaccuguc uccugagucu acucuaccuc gcucguucuc augacucuag    60
aauagacaga ggagacacau aaugggacau aaccuggcgg cagcgcaaaa gaug        114

<210> SEQ ID NO 7
<211> LENGTH: 114
<212> TYPE: RNA
<213> ORGANISM: Artificial Sequence
<220> FEATURE:
<223> OTHER INFORMATION: synthetic

<400> SEQUENCE: 7
gggcauugga aucgaguauc uccuacguuu aacuuaaccc uauacccuca uaacccuuaa    60
gauaaacaga ggagauauac gauggcaaug aaccuggcgg cagcgcaaaa gaug          114

<210> SEQ ID NO 8
<211> LENGTH: 114
<212> TYPE: RNA
<213> ORGANISM: Artificial Sequence
<220> FEATURE:
<223> OTHER INFORMATION: synthetic

<400> SEQUENCE: 8
gggauguaca auccauuauc uccuaagucu uauucuacug ccuuguucca cucccguaga    60
acaagacaga ggagauaacg gaugauacau aaccuggcgg cagcgcaaaa gaug          114

<210> SEQ ID NO 9
<211> LENGTH: 114
<212> TYPE: RNA
<213> ORGANISM: Artificial Sequence
<220> FEATURE:
<223> OTHER INFORMATION: synthetic

<400> SEQUENCE: 9
gggcauuaca auuaccuauc uccuacauuc uagugccacg aguuaguauc uucgccugca    60
caagaauaga ggagauagau aaugguaaug aaccuggcgg cagcgcaaaa gaug          114

<210> SEQ ID NO 10
<211> LENGTH: 114
<212> TYPE: RNA
<213> ORGANISM: Artificial Sequence
<220> FEATURE:
<223> OTHER INFORMATION: synthetic

<400> SEQUENCE: 10
gggcauauga aucggaaguc uccuacaguc auuucgucuu cgaggccguc ucaucugcga    60
acugacuaga ggagacuaac gaugaauaug aaccuggcgg cagcgcaaaa gaug          114

<210> SEQ ID NO 11
<211> LENGTH: 114
<212> TYPE: RNA
<213> ORGANISM: Artificial Sequence
<220> FEATURE:
<223> OTHER INFORMATION: synthetic

<400> SEQUENCE: 11
gggcaucaca auuacauauc uccugaaucu ucauccauu ccauugucuc cagaccggaa     60
ugaagauaga ggagauagau aaugaugaug aaccuggcgg cagcgcaaaa gaug          114

<210> SEQ ID NO 12
<211> LENGTH: 114
<212> TYPE: RNA
<213> ORGANISM: Artificial Sequence
<220> FEATURE:
<223> OTHER INFORMATION: synthetic

<400> SEQUENCE: 12
gggaucauag augcaguauc uccuaaacuu ccacuucgau cgcagguuuc acacuacaag    60
uagaaguaga ggagauaacg caugaaugau aaccuggcgg cagcgcaaaa gaug          114

<210> SEQ ID NO 13

<211> LENGTH: 114
<212> TYPE: RNA
<213> ORGANISM: Artificial Sequence
<220> FEATURE:
<223> OTHER INFORMATION: synthetic

<400> SEQUENCE: 13

```
ggucguuca auguaguauc uccuaagucg uuucuaguac gagaucgccu guucccauag    60
auacgacaga ggagauaaga caugaaacga aaccuggcgg cagcgcaaaa gaug         114
```

<210> SEQ ID NO 14
<211> LENGTH: 114
<212> TYPE: RNA
<213> ORGANISM: Artificial Sequence
<220> FEATURE:
<223> OTHER INFORMATION: synthetic

<400> SEQUENCE: 14

```
gggcauuugc auauaccauc uccuaagucu uauucgugac gcuuaagucc cgcagagcga    60
auaagacaga ggagaugaga uauggaaaug aaccuggcgg cagcgcaaaa gaug          114
```

<210> SEQ ID NO 15
<211> LENGTH: 114
<212> TYPE: RNA
<213> ORGANISM: Artificial Sequence
<220> FEATURE:
<223> OTHER INFORMATION: synthetic

<400> SEQUENCE: 15

```
gggccauaca aucaaccguc uccuaaguau uccaauaccg ugucaaucuc uauaagcauu    60
gaaauacaga ggagacggau gaugauaugg aaccuggcgg cagcgcaaaa gaug          114
```

<210> SEQ ID NO 16
<211> LENGTH: 114
<212> TYPE: RNA
<213> ORGANISM: Artificial Sequence
<220> FEATURE:
<223> OTHER INFORMATION: synthetic

<400> SEQUENCE: 16

```
gggcaauuac augcaacguc uccuacauuc uuaucuauca aaguucacgc acuacgcaga    60
uaagaauaga ggagacgaag caugaaauug aaccuggcgg cagcgcaaaa gaug          114
```

<210> SEQ ID NO 17
<211> LENGTH: 108
<212> TYPE: RNA
<213> ORGANISM: Artificial Sequence
<220> FEATURE:
<223> OTHER INFORMATION: synthetic

<400> SEQUENCE: 17

```
gggacucuac auguacuauc uccuacguuu aucuaugcuc cuauaucguc acgucugaua    60
gauaaacaga ggagauaaga caugcagagu aaccuggcgg cagcgcaa               108
```

<210> SEQ ID NO 18
<211> LENGTH: 108
<212> TYPE: RNA
<213> ORGANISM: Artificial Sequence
<220> FEATURE:
<223> OTHER INFORMATION: synthetic

<400> SEQUENCE: 18

```
gggaucuacc auucauuauc uccuagguuu caguucuauu agggcuacga agaccgugaa    60
```
cagaaacaga ggagauacgg aaugauagau aaccuggcgg cagcgcaa         108

<210> SEQ ID NO 19
<211> LENGTH: 108
<212> TYPE: RNA
<213> ORGANISM: Artificial Sequence
<220> FEATURE:
<223> OTHER INFORMATION: synthetic

<400> SEQUENCE: 19
gggcuuauac auuuaccguc uccuaagcuu agucgugaaa ccuauacaau ccugugcacg    60
aauaagcaga ggagacgaca aaugaauaag aaccuggcgg cagcgcaa         108

<210> SEQ ID NO 20
<211> LENGTH: 108
<212> TYPE: RNA
<213> ORGANISM: Artificial Sequence
<220> FEATURE:
<223> OTHER INFORMATION: synthetic

<400> SEQUENCE: 20
gggcuuagca auguagaauc uccugaguua guucccauug uuacuuucac aucucacggg    60
aacuaacaga ggagauugaa caugacuaag aaccuggcgg cagcgcaa         108

<210> SEQ ID NO 21
<211> LENGTH: 108
<212> TYPE: RNA
<213> ORGANISM: Artificial Sequence
<220> FEATURE:
<223> OTHER INFORMATION: synthetic

<400> SEQUENCE: 21
gggccuaaca auguaccguc uccuaagucu cgaucccggu aucuuauggc cuggucggga    60
uagagacaga ggagacgaaa caugauuagg aaccuggcgg cagcgcaa         108

<210> SEQ ID NO 22
<211> LENGTH: 108
<212> TYPE: RNA
<213> ORGANISM: Artificial Sequence
<220> FEATURE:
<223> OTHER INFORMATION: synthetic

<400> SEQUENCE: 22
gggcuuaucc auuucacguc uccuacgccu ucaucgucgu cuugcaccgu ccuacuccga    60
uaaaggcaga ggagacgaca aaugaauaag aaccuggcgg cagcgcaa         108

<210> SEQ ID NO 23
<211> LENGTH: 108
<212> TYPE: RNA
<213> ORGANISM: Artificial Sequence
<220> FEATURE:
<223> OTHER INFORMATION: synthetic

<400> SEQUENCE: 23
gggccuaaca auucuauauc uccuaagugu caguucuuag gcuacacaug ugagugugaa    60
cagacacaga ggagauaacg aaugauuagg aaccuggcgg cagcgcaa         108

<210> SEQ ID NO 24
<211> LENGTH: 108
<212> TYPE: RNA
<213> ORGANISM: Artificial Sequence
<220> FEATURE:

<223> OTHER INFORMATION: synthetic

<400> SEQUENCE: 24
gggcuuauca auugcacauc uccuagguca ucucguccaa aucgaucauc acguccacg      60 agaugacaga ggagaugaac aauggauaag aaccuggcgg cagcgcaa                 108

<210> SEQ ID NO 25
<211> LENGTH: 58
<212> TYPE: RNA
<213> ORGANISM: Artificial Sequence
<220> FEATURE:
<223> OTHER INFORMATION: synthetic

<400> SEQUENCE: 25
gggccaguga cuugucacug ggaacggacc cuagggcuuc acagaauacg gaaacgac       58

<210> SEQ ID NO 26
<211> LENGTH: 58
<212> TYPE: RNA
<213> ORGANISM: Artificial Sequence
<220> FEATURE:
<223> OTHER INFORMATION: synthetic

<400> SEQUENCE: 26
gggaguggca cgcgugccac uaauggacag gacgagagcg aauuggaacg agaacgac       58

<210> SEQ ID NO 27
<211> LENGTH: 58
<212> TYPE: RNA
<213> ORGANISM: Artificial Sequence
<220> FEATURE:
<223> OTHER INFORMATION: synthetic

<400> SEQUENCE: 27
gggucuccac ggaaguggag auaaggaugc acacgucccc gaagcgacua aagacaaa       58

<210> SEQ ID NO 28
<211> LENGTH: 58
<212> TYPE: RNA
<213> ORGANISM: Artificial Sequence
<220> FEATURE:
<223> OTHER INFORMATION: synthetic

<400> SEQUENCE: 28
gggcacggac uccuguccgu gggcgagaca ggcuuacggu agcauaaacu aauacaac       58

<210> SEQ ID NO 29
<211> LENGTH: 58
<212> TYPE: RNA
<213> ORGANISM: Artificial Sequence
<220> FEATURE:
<223> OTHER INFORMATION: synthetic

<400> SEQUENCE: 29
gggcucaccu gccaagguga gagcgacgac uguuacaagg acuuuaagau gaaacgac       58

<210> SEQ ID NO 30
<211> LENGTH: 58
<212> TYPE: RNA
<213> ORGANISM: Artificial Sequence
<220> FEATURE:
<223> OTHER INFORMATION: synthetic

<400> SEQUENCE: 30
gggcuggagc auacgcucca gaaugaguca ugagaacgag cgagguagag uagacgaa       58

<210> SEQ ID NO 31
<211> LENGTH: 58
<212> TYPE: RNA
<213> ORGANISM: Artificial Sequence
<220> FEATURE:
<223> OTHER INFORMATION: synthetic

<400> SEQUENCE: 31
gggacaaugu aagaacauug uacgaggguu augaggguau agggguuaagu uaaacagc    58

<210> SEQ ID NO 32
<211> LENGTH: 58
<212> TYPE: RNA
<213> ORGANISM: Artificial Sequence
<220> FEATURE:
<223> OTHER INFORMATION: synthetic

<400> SEQUENCE: 32
gggauccuga auacucagga ugaaacggga guggaacaag gcaguagaau aagacaac    58

<210> SEQ ID NO 33
<211> LENGTH: 58
<212> TYPE: RNA
<213> ORGANISM: Artificial Sequence
<220> FEATURE:
<223> OTHER INFORMATION: synthetic

<400> SEQUENCE: 33
ggguccgauc uagagaucgg auaaaggcga agauacuaac ucguggcacu agaauaca    58

<210> SEQ ID NO 34
<211> LENGTH: 58
<212> TYPE: RNA
<213> ORGANISM: Artificial Sequence
<220> FEATURE:
<223> OTHER INFORMATION: synthetic

<400> SEQUENCE: 34
gggauccagc cgaugcugga ugaacagaug agacggccuc gaagacgaaa ugacuaga    58

<210> SEQ ID NO 35
<211> LENGTH: 58
<212> TYPE: RNA
<213> ORGANISM: Artificial Sequence
<220> FEATURE:
<223> OTHER INFORMATION: synthetic

<400> SEQUENCE: 35
gggagccauc gcaugauggc uggacggucu ggagacaaug gaauggaaug aagauacu    58

<210> SEQ ID NO 36
<211> LENGTH: 58
<212> TYPE: RNA
<213> ORGANISM: Artificial Sequence
<220> FEATURE:
<223> OTHER INFORMATION: synthetic

<400> SEQUENCE: 36
gggcagcuac ucaaguagcu ggagguagug ugaaaccugc gaucgaagug gaaguacg    58

<210> SEQ ID NO 37
<211> LENGTH: 58
<212> TYPE: RNA
<220> FEATURE:
<213> ORGANISM: Artificial Sequence
<223> OTHER INFORMATION: synthetic

<400> SEQUENCE: 37
gggagucagc ugaugcugac uaaguggggaa caggcgaucu cguacuagaa acgacaau    58

<210> SEQ ID NO 38
<211> LENGTH: 58
<212> TYPE: RNA
<213> ORGANISM: Artificial Sequence
<220> FEATURE:
<223> OTHER INFORMATION: synthetic

<400> SEQUENCE: 38
gggcgucacc uuuaggugac ggaacucugc gggacuuaag cgucacgaau aagacaca    58

<210> SEQ ID NO 39
<211> LENGTH: 58
<212> TYPE: RNA
<213> ORGANISM: Artificial Sequence
<220> FEATURE:
<223> OTHER INFORMATION: synthetic

<400> SEQUENCE: 39
gggcagaccc ugcugggucu ggacgcuuau agagauugac acgguauugg aauacaaa    58

<210> SEQ ID NO 40
<211> LENGTH: 58
<212> TYPE: RNA
<213> ORGANISM: Artificial Sequence
<220> FEATURE:
<223> OTHER INFORMATION: synthetic

<400> SEQUENCE: 40
gggacguuac uuagguaacg uggagcguag ugcgugaacu uugauagaua agaaugaa    58

<210> SEQ ID NO 41
<211> LENGTH: 58
<212> TYPE: RNA
<213> ORGANISM: Artificial Sequence
<220> FEATURE:
<223> OTHER INFORMATION: synthetic

<400> SEQUENCE: 41
gggagcucgc aaccgcgagc uagacagacg ugacgauaua ggagcauaga uaaacuca    58

<210> SEQ ID NO 42
<211> LENGTH: 58
<212> TYPE: RNA
<213> ORGANISM: Artificial Sequence
<220> FEATURE:
<223> OTHER INFORMATION: synthetic

<400> SEQUENCE: 42
gggagcaugc cguggcaugc uaggacgguc uucguagccc uaauagaacu gaaacaug    58

<210> SEQ ID NO 43
<211> LENGTH: 58
<212> TYPE: RNA
<213> ORGANISM: Artificial Sequence
<220> FEATURE:
<223> OTHER INFORMATION: synthetic

<400> SEQUENCE: 43
gggcacagac guacgucugu ggaagcacag gauuguauag guuucacgac uaagcgaa    58

<210> SEQ ID NO 44
<211> LENGTH: 58
<212> TYPE: RNA
<213> ORGANISM: Artificial Sequence
<220> FEATURE:
<223> OTHER INFORMATION: synthetic

<400> SEQUENCE: 44
gggccuacgc acucgcguag gauugugaga ugugaaagua acaaugggaa cuaacgaa    58

<210> SEQ ID NO 45
<211> LENGTH: 58
<212> TYPE: RNA
<213> ORGANISM: Artificial Sequence
<220> FEATURE:
<223> OTHER INFORMATION: synthetic

<400> SEQUENCE: 45
gggccagacc aucgggucug gaggcgacca ggccauaaga uaccgggauc gagacaac    58

<210> SEQ ID NO 46
<211> LENGTH: 58
<212> TYPE: RNA
<213> ORGANISM: Artificial Sequence
<220> FEATURE:
<223> OTHER INFORMATION: synthetic

<400> SEQUENCE: 46
gggaccguac ucccguacgg ugaugaguag gacggugcaa gacgacgaug aaggcuac    58

<210> SEQ ID NO 47
<211> LENGTH: 58
<212> TYPE: RNA
<213> ORGANISM: Artificial Sequence
<220> FEATURE:
<223> OTHER INFORMATION: synthetic

<400> SEQUENCE: 47
gggaugaucg acaccgauca uagaacacuc acauguguag ccuaagaacu gacacagc    58

<210> SEQ ID NO 48
<211> LENGTH: 58
<212> TYPE: RNA
<213> ORGANISM: Artificial Sequence
<220> FEATURE:
<223> OTHER INFORMATION: synthetic

<400> SEQUENCE: 48
gggcugcucc cgugggagca ggacggacag ugaugaucga uuuggacgag augacaua    58

<210> SEQ ID NO 49
<211> LENGTH: 114
<212> TYPE: RNA
<213> ORGANISM: Artificial Sequence
<220> FEATURE:
<223> OTHER INFORMATION: synthetic

<400> SEQUENCE: 49
gggucgugcu auuucacauc uccuaaguuu ccguauucug ugaagcccua ggguccgaua    60
cagaaacaga ggagaugaca aaugacacga aaccuggcgg cagcgcaaaa gaug          114

<210> SEQ ID NO 50
<211> LENGTH: 114
<212> TYPE: RNA
<213> ORGANISM: Artificial Sequence
<220> FEATURE:

<223> OTHER INFORMATION: synthetic

<400> SEQUENCE: 50
gggcuuaugu auuucacauc uccuaaguuu ccguauucug ugaagcccua ggguccgaua    60
cagaaacaga ggagaugaca aaugaauaag aaccuggcgg cagcgcaaaa gaug    114

<210> SEQ ID NO 51
<211> LENGTH: 114
<212> TYPE: RNA
<213> ORGANISM: Artificial Sequence
<220> FEATURE:
<223> OTHER INFORMATION: synthetic

<400> SEQUENCE: 51
gggucguugu auuucacauc uccuaaguuu ccguauucug ugaagcccua ggguccgaua    60
cagaaacaga ggagaugaca aauggaacga aaccuggcgg cagcgcaaaa gaug    114

<210> SEQ ID NO 52
<211> LENGTH: 114
<212> TYPE: RNA
<213> ORGANISM: Artificial Sequence
<220> FEATURE:
<223> OTHER INFORMATION: synthetic

<400> SEQUENCE: 52
gggcuugucu auuucacauc uccuaaguuu ccguauucug ugaagcccua ggguccgaua    60
cagaaacaga ggagaugaca aaugaacaag aaccuggcgg cagcgcaaaa gaug    114

<210> SEQ ID NO 53
<211> LENGTH: 58
<212> TYPE: RNA
<213> ORGANISM: Artificial Sequence
<220> FEATURE:
<223> OTHER INFORMATION: synthetic

<400> SEQUENCE: 53
gggccaguga cuugucacug ggaacggacc cuagggcuuc acagaauacg gaaacgac    58

<210> SEQ ID NO 54
<211> LENGTH: 114
<212> TYPE: RNA
<213> ORGANISM: Artificial Sequence
<220> FEATURE:
<223> OTHER INFORMATION: synthetic

<400> SEQUENCE: 54
gggucuaucu auuucacauc uccuaaguuu ccguauucug ugaagcccua ggguccgaua    60
cggaaacaga ggagaugaca aaugaauaga aaccuggcgg cagcgcaaaa gaug    114

<210> SEQ ID NO 55
<211> LENGTH: 114
<212> TYPE: RNA
<213> ORGANISM: Artificial Sequence
<220> FEATURE:
<223> OTHER INFORMATION: synthetic

<400> SEQUENCE: 55
gggucuaucu auuucacauc uccuaaguuu cgguauucug ugaagcccua ggguccgaua    60
ccgaaacaga ggagaugaca aaugaauaga aaccuggcgg cagcgcaaaa gaug    114

<210> SEQ ID NO 56
<211> LENGTH: 22

```
<212> TYPE: RNA
<213> ORGANISM: Artificial Sequence
<220> FEATURE:
<223> OTHER INFORMATION: synthetic

<400> SEQUENCE: 56
gggcuucaca gaauacagaa ac                                              22

<210> SEQ ID NO 57
<211> LENGTH: 22
<212> TYPE: RNA
<213> ORGANISM: Artificial Sequence
<220> FEATURE:
<223> OTHER INFORMATION: synthetic

<400> SEQUENCE: 57
gggcuucaca gaauaccgaa ac                                              22

<210> SEQ ID NO 58
<211> LENGTH: 22
<212> TYPE: RNA
<213> ORGANISM: Artificial Sequence
<220> FEATURE:
<223> OTHER INFORMATION: synthetic

<400> SEQUENCE: 58
gggcuucaca gaauacugaa ac                                              22

<210> SEQ ID NO 59
<211> LENGTH: 58
<212> TYPE: RNA
<213> ORGANISM: Artificial Sequence
<220> FEATURE:
<223> OTHER INFORMATION: synthetic

<400> SEQUENCE: 59
gggccaguga cuugucacug ggaacggacc cuagggcuuc acagaauacg gaaacgac       58

<210> SEQ ID NO 60
<211> LENGTH: 146
<212> TYPE: RNA
<213> ORGANISM: Artificial Sequence
<220> FEATURE:
<223> OTHER INFORMATION: synthetic

<400> SEQUENCE: 60
gggugaauag uggagaccgg uuucuaucua uuguauucuu guuccgaaac cgaucuccac      60
uauucagcuu aagcacaauc agccucgauu guacuuaagc agaauagagg agauagacaa     120
ugaaccuggc ggcagcgcaa aagaug                                         146

<210> SEQ ID NO 61
<211> LENGTH: 55
<212> TYPE: RNA
<213> ORGANISM: Artificial Sequence
<220> FEATURE:
<223> OTHER INFORMATION: synthetic

<400> SEQUENCE: 61
gggaccagcc acugggcugg uauaggaaca agaauacaau agauagaaac cgaaa           55

<210> SEQ ID NO 62
<211> LENGTH: 158
<212> TYPE: RNA
<213> ORGANISM: Artificial Sequence
<220> FEATURE:
```

<223> OTHER INFORMATION: synthetic

<400> SEQUENCE: 62
gggauaaacu acaaagcgac aauggagacu cgcgcucuau uccauuaucu uauucuuagc    60
gcgagucucc acugucgcag acauguucca cuccugcuag uggaccaugu cuacgacaga   120
ggagacacgg aaugaaccug gcggcagcgc aaaagaug                           158

<210> SEQ ID NO 63
<211> LENGTH: 55
<212> TYPE: RNA
<213> ORGANISM: Artificial Sequence
<220> FEATURE:
<223> OTHER INFORMATION: synthetic

<400> SEQUENCE: 63
gggcagcggu auugaccgcu gaguaagaau aagauaaugg aauagagcgc gaaga         55

<210> SEQ ID NO 64
<211> LENGTH: 156
<212> TYPE: RNA
<213> ORGANISM: Artificial Sequence
<220> FEATURE:
<223> OTHER INFORMATION: synthetic

<400> SEQUENCE: 64
gggcagauau aggagaucgg uguaguuuau gugcuuuagg uuauacaccg aucuccugua    60
ucuggcguca cucgaacugu cuaaaguagg uuagacuguu cgaaugacgc aagauagagg   120
agacaacgaa ugaaccuggc ggcagcgcaa aagaug                             156

<210> SEQ ID NO 65
<211> LENGTH: 54
<212> TYPE: RNA
<213> ORGANISM: Artificial Sequence
<220> FEATURE:
<223> OTHER INFORMATION: synthetic

<400> SEQUENCE: 65
gggcaaggcc uauuggccuu gagaauaacc uaaagcacau aaacuacacc gaaa          54

<210> SEQ ID NO 66
<211> LENGTH: 168
<212> TYPE: RNA
<213> ORGANISM: Artificial Sequence
<220> FEATURE:
<223> OTHER INFORMATION: synthetic

<400> SEQUENCE: 66
gggaauaagu agacaugaac auaggagacc gguguagugu aguguaugua uguaagacac    60
cgaucuccua uguucacguu ccuggagucg aacauuacga cgaauguuag acuccuggaa   120
cgagaacaga ggagacacau aaugaaccug gcggcagcgc aaaagaug                168

<210> SEQ ID NO 67
<211> LENGTH: 54
<212> TYPE: RNA
<213> ORGANISM: Artificial Sequence
<220> FEATURE:
<223> OTHER INFORMATION: synthetic

<400> SEQUENCE: 67
gggccaugca caguugcaug ggaacuuaca uacauacacu acacuacacc gaau          54

<210> SEQ ID NO 68
<211> LENGTH: 231
<212> TYPE: RNA
<213> ORGANISM: Artificial Sequence
<220> FEATURE:
<223> OTHER INFORMATION: synthetic

<400> SEQUENCE: 68

```
gggauucauu ucacaucucc uaauccaguc guggaugggc ucuguuccg uauucuguga      60
agcccuaggg uccgauacag aaacagagcc cauccacgac uggaauggcu cuguuucauc    120
uuaaaguccu uguaacaguc gucaagacga aacuaagcca uagaggagau gacaaaugaa    180
uaaccuggcg gcagcgcaaa agaugcguaa aggagaagaa cuuuucacug g             231
```

<210> SEQ ID NO 69
<211> LENGTH: 78
<212> TYPE: RNA
<213> ORGANISM: Artificial Sequence
<220> FEATURE:
<223> OTHER INFORMATION: synthetic

<400> SEQUENCE: 69

```
gggccaguga cuugucacug ggaacggacc cuagggcuuc acagaauacg gaaacagagc      60
ccauccacga cuggagac                                                    78
```

<210> SEQ ID NO 70
<211> LENGTH: 58
<212> TYPE: RNA
<213> ORGANISM: Artificial Sequence
<220> FEATURE:
<223> OTHER INFORMATION: synthetic

<400> SEQUENCE: 70

```
gggccaguga cuugucacug gagcgacgac uguuacaagg acuuuaagau gaaacgac        58
```

<210> SEQ ID NO 71
<211> LENGTH: 71
<212> TYPE: RNA
<213> ORGANISM: Artificial Sequence
<220> FEATURE:
<223> OTHER INFORMATION: synthetic

<400> SEQUENCE: 71

```
gggccaguga cuugucacug ggaacggacc cuagggcuuc acagaauacg gaaacagagc      60
ccauccacga c                                                           71
```

<210> SEQ ID NO 72
<211> LENGTH: 251
<212> TYPE: RNA
<213> ORGANISM: Artificial Sequence
<220> FEATURE:
<223> OTHER INFORMATION: synthetic

<400> SEQUENCE: 72

```
gggacucaaa ucuucgcuac agcgacaucu acaguuccg uauucuguga agcccuaggg      60
uccgauacag aaacgguaga acucgcuaaa gcgaugucua ccugccauau cuuaucuccu    120
gaguuucauc uuaaaguccu uguaacaguc gucaagacga aacagaggag auacaauaug    180
gcaauuagac aagauacgag uaaccuggcg gcagcgcaaa agaugcguaa aggagaagaa    240
cuuuucacug g                                                         251
```

<210> SEQ ID NO 73

```
<211> LENGTH: 58
<212> TYPE: RNA
<213> ORGANISM: Artificial Sequence
<220> FEATURE:
<223> OTHER INFORMATION: synthetic

<400> SEQUENCE: 73
gggccaguga cuugucacug ggaacggacc cuagggcuuc acagaauacg gaaacgac      58

<210> SEQ ID NO 74
<211> LENGTH: 58
<212> TYPE: RNA
<213> ORGANISM: Artificial Sequence
<220> FEATURE:
<223> OTHER INFORMATION: synthetic

<400> SEQUENCE: 74
gggcucaccu gccaagguga gagcgacgac uguuacaagg acuuuaagau gaaacgac      58

<210> SEQ ID NO 75
<211> LENGTH: 246
<212> TYPE: RNA
<213> ORGANISM: Artificial Sequence
<220> FEATURE:
<223> OTHER INFORMATION: synthetic

<400> SEQUENCE: 75
gggcauucua ucuacaucua uuucaacuga uuucaguaau acaccguuuc cguauucugu      60
gaagcccuag gguccgauac agaaacggug uauuacugaa aucagucuua caccugccau     120
augauaucuc cucuguuuca ucuuaaaguc cuuguaacag cgucaagac gaaacagagg     180 agauaagaua uggcaaaugu aagugaaaua gauagagaua gaaugaaccu ggcggcagcg    240
caaaag                                                              246

<210> SEQ ID NO 76
<211> LENGTH: 58
<212> TYPE: RNA
<213> ORGANISM: Artificial Sequence
<220> FEATURE:
<223> OTHER INFORMATION: synthetic

<400> SEQUENCE: 76
gggccaguga cuugucacug ggaacggacc cuagggcuuc acagaauacg gaaacgac      58

<210> SEQ ID NO 77
<211> LENGTH: 58
<212> TYPE: RNA
<213> ORGANISM: Artificial Sequence
<220> FEATURE:
<223> OTHER INFORMATION: synthetic

<400> SEQUENCE: 77
gggcucaccu gccaagguga gagcgacgac uguuacaagg acuuuaagau gaaacgac      58

<210> SEQ ID NO 78
<211> LENGTH: 237
<212> TYPE: RNA
<213> ORGANISM: Artificial Sequence
<220> FEATURE:
<223> OTHER INFORMATION: synthetic

<400> SEQUENCE: 78
gggauucauu ucacaucugc ucuauaucgu ccgcaauccu guuccguau ucgugaagc       60 ccuaggqucc gauacagaaa cuugauugac gacgaccuac gcucauuucg uuucaucuua    120
```
aaguccuugu aacagucguc aagacgaaac gaaaugaaag uaggaauaga ggagaugaca    180
aaugaauaac cuggcggcag cgcaaaagau gcguaaagga gaagaacuuu ucacugg    237

<210> SEQ ID NO 79
<211> LENGTH: 72
<212> TYPE: RNA
<213> ORGANISM: Artificial Sequence
<220> FEATURE:
<223> OTHER INFORMATION: synthetic

<400> SEQUENCE: 79
gggccaguga cuugucacug gaacggacc cuagggcuuc acagaauacg gaaacaggau    60
ugcggacgag ac    72

<210> SEQ ID NO 80
<211> LENGTH: 72
<212> TYPE: RNA
<213> ORGANISM: Artificial Sequence
<220> FEATURE:
<223> OTHER INFORMATION: synthetic

<400> SEQUENCE: 80
gggccaguga cuugucacug gagcgacgac uguuacaagg acuuuaagau gaaacgaaau    60
gagcguaggg ac    72

<210> SEQ ID NO 81
<211> LENGTH: 155
<212> TYPE: RNA
<213> ORGANISM: Artificial Sequence
<220> FEATURE:
<223> OTHER INFORMATION: synthetic

<400> SEQUENCE: 81
gggcuugcuu auguuccgu auucugugaa gcccuagggu ccgauaccga aaccauaucu    60
uaucuccuga guuucaucuu aaaguccuug uaacagucgu caagacgaaa cagaggagau    120
aacauaugau aagcaagaac cuggcggcag cgcaa    155

<210> SEQ ID NO 82
<211> LENGTH: 58
<212> TYPE: RNA
<213> ORGANISM: Artificial Sequence
<220> FEATURE:
<223> OTHER INFORMATION: synthetic

<400> SEQUENCE: 82
gggccaguga cuugucacug gaacggacc cuagggcuuc acagaauacg gaaacgac    58

<210> SEQ ID NO 83
<211> LENGTH: 58
<212> TYPE: RNA
<213> ORGANISM: Artificial Sequence
<220> FEATURE:
<223> OTHER INFORMATION: synthetic

<400> SEQUENCE: 83
gggcucaccu gccaagguga gagcgacgac uguuacaagg acuuuaagau gaaacgac    58

<210> SEQ ID NO 84
<211> LENGTH: 123
<212> TYPE: RNA
<213> ORGANISM: Artificial Sequence
<220> FEATURE:

<223> OTHER INFORMATION: synthetic

<400> SEQUENCE: 84

```
ggguaacgga ugauguacaa uccauuaucu ccuaaguccu ccuacucccu gacaugcugu    60
caucauuucu ucguaggagg acagaggaga uaacggauga uacauaaccu ggcggcagcg   120
caa                                                                 123
```

<210> SEQ ID NO 85
<211> LENGTH: 145
<212> TYPE: RNA
<213> ORGANISM: Artificial Sequence
<220> FEATURE:
<223> OTHER INFORMATION: synthetic

<400> SEQUENCE: 85

```
gggagcauug ggaccagcgg cuacacuaga agaaaugaug acagcauguc agggaguagg    60
aggacccggc cauaaggcaa gaguuuuggc ugaagcaaug agccaaguaa caaauucagc   120
uaccauaaug augcagagag gcaau                                        145
```

<210> SEQ ID NO 86
<211> LENGTH: 123
<212> TYPE: RNA
<213> ORGANISM: Artificial Sequence
<220> FEATURE:
<223> OTHER INFORMATION: synthetic

<400> SEQUENCE: 86

```
ggguaacgga ugauguacaa uccauuaucu ccuaaaaaau aaaacaaaaa acaaaacaaa    60
uuggaaacag acguuuuauu uuagaggaga uaacggauga uacauaaccu ggcggcagcg   120
caa                                                                 123
```

<210> SEQ ID NO 87
<211> LENGTH: 117
<212> TYPE: RNA
<213> ORGANISM: Artificial Sequence
<220> FEATURE:
<223> OTHER INFORMATION: synthetic

<400> SEQUENCE: 87

```
gaacaugucu ggucguaaag cucagggaaa aacccugggc gucaauaugg uacgacgagg    60
aguucgcucc uugucaaaca aaauaaaaca aaaaacaaaa caaauuggaa acagacc     117
```

<210> SEQ ID NO 88
<211> LENGTH: 123
<212> TYPE: RNA
<213> ORGANISM: Artificial Sequence
<220> FEATURE:
<223> OTHER INFORMATION: synthetic

<400> SEQUENCE: 88

```
ggguaacgga ugauguacaa uccauuaucu ccuaaggugg cuucggcucu ggugaauug    60 ggcguuaucu cacgaagcca ccagaggaga uaacggauga uacauaaccu ggcggcagcg   120
caa                                                                 123
```

<210> SEQ ID NO 89
<211> LENGTH: 102
<212> TYPE: RNA
<213> ORGANISM: Artificial Sequence
<220> FEATURE:
<223> OTHER INFORMATION: synthetic

```
<400> SEQUENCE: 89
augacacagg acaugaaacu gaugagaaua gagcgaaagu ugagauaacg cccaauucac    60
caagagccga agccacccug gggggguuug gaagccuagg ac                      102

<210> SEQ ID NO 90
<211> LENGTH: 123
<212> TYPE: RNA
<213> ORGANISM: Artificial Sequence
<220> FEATURE:
<223> OTHER INFORMATION: synthetic

<400> SEQUENCE: 90
ggguaacgga ugauguacaa uccauuaucu ccuaagcacg ugggagggcg aucgcaaucu    60
ggcucccagu uucccacgu gcagaggaga uaacggauga uacauaaccu ggcggcagcg   120
caa                                                                 123

<210> SEQ ID NO 91
<211> LENGTH: 97
<212> TYPE: RNA
<213> ORGANISM: Artificial Sequence
<220> FEATURE:
<223> OTHER INFORMATION: synthetic

<400> SEQUENCE: 91
gcacguggga gggcgaucgc aaucuggcuc ccaguuuugu gaaugaagau ggcgucgaau    60
gacgccaacc caucugaugg guccgcagcc aaccucg                            97

<210> SEQ ID NO 92
<211> LENGTH: 123
<212> TYPE: RNA
<213> ORGANISM: Artificial Sequence
<220> FEATURE:
<223> OTHER INFORMATION: synthetic

<400> SEQUENCE: 92
ggguaacgga ugauguacaa uccauuaucu ccuaagagcg uguguacaa ggcaacaaua     60 cacgcuagau caucaccgc ucagaggaga uaacggauga uacauaaccu ggcggcagcg   120
caa                                                                 123

<210> SEQ ID NO 93
<211> LENGTH: 53
<212> TYPE: DNA
<213> ORGANISM: Artificial Sequence
<220> FEATURE:
<223> OTHER INFORMATION: synthetic

<400> SEQUENCE: 93
agccttgcaa taataatat ctagcgtgta ttgttgcctt gtacacaccg ctc            53

<210> SEQ ID NO 94
<211> LENGTH: 129
<212> TYPE: RNA
<213> ORGANISM: Artificial Sequence
<220> FEATURE:
<223> OTHER INFORMATION: synthetic

<400> SEQUENCE: 94
ggguaacgga ugauguacaa uccauuaucu ccuaagcuug uaaauguaau cuuggauaug    60 auauggtuaaa uaauuuacaa gcagaggaga uaacggauga uacauaaccu ggcggcagcg  120
```

-continued

```
caaaagaug                                                           129

<210> SEQ ID NO 95
<211> LENGTH: 161
<212> TYPE: RNA
<213> ORGANISM: Artificial Sequence
<220> FEATURE:
<223> OTHER INFORMATION: synthetic

<400> SEQUENCE: 95
gacuguaaau aaaccaugug gagauuuuuc caaauguauu aaaauagaug gaaaucccgu    60
uucauacgcu uguaaaugua aucuuggaua ugauauggua aauaauguuu guauaccaaa   120
ugaauguaag aauguaacuu gugguaacgg uaaaugauau g                       161
```